(12) United States Patent
Baehner et al.

(10) Patent No.: US 8,969,526 B2
(45) Date of Patent: Mar. 3, 2015

(54) ANTIBODY FC VARIANTS

(75) Inventors: Monika Baehner, Munich (DE); Stefan Jenewein, Neustadt/Weinstrasse (DE); Manfred Kubbies, Penzberg (DE); Ekkehard Moessner, Kreuzlingen (CH); Tilman Schlothauer, Penzberg (DE)

(73) Assignee: Roche Glycart AG, Schlieren (CH)

( * ) Notice: Subject to any disclaimer, the term of this patent is extended or adjusted under 35 U.S.C. 154(b) by 28 days.

(21) Appl. No.: 13/431,489

(22) Filed: Mar. 27, 2012

(65) Prior Publication Data

US 2012/0251531 A1    Oct. 4, 2012

(30) Foreign Application Priority Data

Mar. 29, 2011 (EP) .................................... 11160251

(51) Int. Cl.
| | | |
|---|---|---|
| C07K 16/00 | (2006.01) | |
| A61K 39/395 | (2006.01) | |
| A61K 39/40 | (2006.01) | |
| C07K 1/00 | (2006.01) | |

(52) U.S. Cl.
CPC ............. *C07K 16/00* (2013.01); *C07K 2317/52* (2013.01); *C07K 2317/71* (2013.01); *C07K 2317/732* (2013.01); *C07K 2317/734* (2013.01); *C07K 2317/92* (2013.01); *C07K 2319/30* (2013.01); *Y10S 435/81* (2013.01)
USPC ................... 530/387.1; 530/387.3; 530/388.1; 530/388.15; 530/388.22; 424/130.1; 424/132.1; 424/133.1; 424/141.1; 424/142.1; 424/143.1; 435/810

(58) Field of Classification Search
None
See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Boguslaski et al. | |
| 4,490,473 A | 12/1984 | Brunhouse | |
| 4,676,980 A | 6/1987 | Segal et al. | |
| 4,737,456 A | 4/1988 | Weng et al. | |
| 4,752,601 A | 6/1988 | Hahn | |
| 4,816,567 A | 3/1989 | Cabilly et al. | |
| 5,047,335 A | 9/1991 | Paulson et al. | |
| 5,091,178 A | 2/1992 | Hellstrom et al. | |
| 5,204,244 A | 4/1993 | Fell et al. | |
| 5,208,020 A | 5/1993 | Chari et al. | |
| 5,225,539 A | 7/1993 | Winter | |
| 5,278,299 A | 1/1994 | Wong et al. | |
| 5,348,876 A | 9/1994 | Michaelsen et al. | |
| 5,416,064 A | 5/1995 | Chari et al. | |
| 5,419,904 A | 5/1995 | Irie | |
| 5,500,362 A | 3/1996 | Robinson et al. | |
| 5,510,261 A | 4/1996 | Goochee et al. | |
| 5,571,894 A | 11/1996 | Wels et al. | |
| 5,576,184 A | 11/1996 | Better et al. | |
| 5,587,458 A | 12/1996 | King et al. | |
| 5,624,821 A | 4/1997 | Winter et al. | |
| 5,635,483 A | 6/1997 | Pettit et al. | |
| 5,648,237 A | 7/1997 | Carter | |
| 5,648,260 A | 7/1997 | Winter et al. | |
| 5,698,449 A | 12/1997 | Baumann et al. | |
| 5,712,374 A | 1/1998 | Kuntsmann et al. | |
| 5,714,586 A | 2/1998 | Kunstmann et al. | |
| 5,730,977 A | 3/1998 | Ooka et al. | |
| 5,731,168 A | 3/1998 | Carter et al. | |
| 5,736,137 A | 4/1998 | Anderson et al. | |
| 5,739,116 A | 4/1998 | Hamann et al. | |
| 5,747,035 A | 5/1998 | Presta et al. | |
| 5,750,373 A | 5/1998 | Garrard et al. | |
| 5,767,285 A | 6/1998 | Hamann et al. | |
| 5,770,429 A | 6/1998 | Lonberg et al. | |
| 5,770,701 A | 6/1998 | McGahren et al. | |
| 5,770,710 A | 6/1998 | McGahren et al. | |
| 5,773,001 A | 6/1998 | Hamann et al. | |
| 5,780,588 A | 7/1998 | Pettit et al. | |
| 5,789,199 A | 8/1998 | Joly et al. | |
| 5,821,337 A | 10/1998 | Carter et al. | |
| 5,834,597 A | 11/1998 | Tso et al. | |
| 5,840,523 A | 11/1998 | Simmons et al. | |
| 5,843,398 A | 12/1998 | Kaminski et al. | |
| 5,869,046 A | 2/1999 | Presta et al. | |
| 5,877,296 A | 3/1999 | Hamann et al. | |
| 5,885,573 A | 3/1999 | Bluestone et al. | |
| 5,959,177 A | 9/1999 | Hein et al. | |
| 5,985,599 A | 11/1999 | Mckenzie et al. | |
| 6,040,498 A | 3/2000 | Stomp et al. | |
| 6,054,297 A | 4/2000 | Carter et al. | |
| 6,075,181 A | 6/2000 | Kucherlaopati et al. | |
| 6,136,310 A | 10/2000 | Hanna et al. | |

(Continued)

FOREIGN PATENT DOCUMENTS

| | | |
|---|---|---|
| CA | 2369292 A | 10/2000 |
| EP | 0 404 097 B1 | 6/1990 |

(Continued)

OTHER PUBLICATIONS

Carroll et al., Thromb Res, 1990; 59:831-39.*
Abes et al., "Activating and inhibitory Fcγ receptors in immunotherapy: being the actor or being the target" Expert Rev Clin Immunol 5(6):735-747 (2009).
Almagro et al., "Humanization of antibodies" Frontiers in Bioscience 13:1619-1633 (Jan. 2008).
Armour et al., "Recombinant human IgG Molecules lacking Fcγ receptor I binding and monocyte triggering activities" Eur J Immunol 29:2613-2624 (1999).
Baca et al., "Antibody humanization using monovalent phage display" J Biol Chem 272(16):10678-10684 (1997).

(Continued)

*Primary Examiner* — Chun Dahle
(74) *Attorney, Agent, or Firm* — Morrison & Foerster LLP

(57) ABSTRACT

The invention relates to engineered polypeptides comprising Fc variants and their uses. More specifically, Fc variants are described exhibiting reduced effector function. These variants cause a benefit for a patient suffering from a disease which could be treated with an antibody for which it is desirable to reduce the effector function elicited by antibodies.

8 Claims, 16 Drawing Sheets

(56) References Cited

U.S. PATENT DOCUMENTS

| | | | |
|---|---|---|---|
| 6,150,584 A | 11/2000 | Kucherlapati et al. | |
| 6,165,464 A | 12/2000 | Hudziak et al. | |
| 6,165,745 A | 12/2000 | Ward et al. | |
| 6,171,586 B1 | 1/2001 | Lam et al. | |
| 6,172,213 B1 | 1/2001 | Lowman et al. | |
| 6,180,377 B1 | 1/2001 | Morgan et al. | |
| 6,194,551 B1 | 2/2001 | Idusogie et al. | |
| 6,242,195 B1 | 6/2001 | Idusogie et al. | |
| 6,248,516 B1 | 6/2001 | Winter et al. | |
| 6,267,958 B1 | 7/2001 | Andya et al. | |
| 6,277,375 B1 | 8/2001 | Ward | |
| 6,417,429 B1 | 7/2002 | Hein et al. | |
| 6,420,548 B1 | 7/2002 | Vezina et al. | |
| 6,491,916 B1 | 12/2002 | Bluestone et al. | |
| 6,528,624 B1 | 3/2003 | Idusogie et al. | |
| 6,538,124 B1 | 3/2003 | Idusogie et al. | |
| 6,582,959 B2 | 6/2003 | Kim | |
| 6,586,207 B2 | 7/2003 | Tirrell et al. | |
| 6,630,579 B2 | 10/2003 | Chari et al. | |
| 6,676,927 B1 | 1/2004 | Ravetch | |
| 6,703,020 B1 | 3/2004 | Thorpe et al. | |
| 6,706,265 B1 | 3/2004 | Bolt et al. | |
| 6,737,056 B1 | 5/2004 | Presta | |
| 6,821,505 B2 | 11/2004 | Ward | |
| 6,946,292 B2 | 9/2005 | Kanda et al. | |
| 6,982,321 B2 | 1/2006 | Winter | |
| 7,041,870 B2 | 5/2006 | Tomizuka et al. | |
| 7,060,269 B1 | 6/2006 | Baca et al. | |
| 7,083,784 B2 | 8/2006 | Dall'Acqua et al. | |
| 7,087,409 B2 | 8/2006 | Barbas et al. | |
| 7,122,637 B2 | 10/2006 | Presta | |
| 7,125,978 B1 | 10/2006 | Vezina et al. | |
| 7,183,387 B1 | 2/2007 | Presta | |
| 7,189,826 B2 | 3/2007 | Rodman | |
| 7,214,775 B2 | 5/2007 | Hanai et al. | |
| 7,297,775 B2 | 11/2007 | Idusogie et al. | |
| 7,332,581 B2 | 2/2008 | Presta | |
| 7,335,742 B2 | 2/2008 | Presta | |
| 7,364,731 B2 | 4/2008 | Idusogie et al. | |
| 7,371,826 B2 | 5/2008 | Presta | |
| 7,416,727 B2 | 8/2008 | Presta | |
| 7,498,298 B2 | 3/2009 | Doronina et al. | |
| 7,521,541 B2 | 4/2009 | Eigenbrot et al. | |
| 7,527,791 B2 | 5/2009 | Adams et al. | |
| 7,563,441 B2 * | 7/2009 | Graus et al. | 424/153.1 |
| 7,598,055 B2 | 10/2009 | Bobrowicz et al. | |
| 7,632,497 B2 | 12/2009 | Stavenhagen | |
| 7,691,977 B2 | 4/2010 | Fuh et al. | |
| 7,741,072 B2 | 6/2010 | Idusogie et al. | |
| 7,785,791 B2 | 8/2010 | Presta | |
| 7,790,858 B2 | 9/2010 | Presta | |
| 7,960,512 B2 | 6/2011 | Stavenhagen et al. | |
| 8,088,376 B2 | 1/2012 | Chamberlain et al. | |
| 2001/0036459 A1 | 11/2001 | Ravetch | |
| 2002/0098193 A1 | 7/2002 | Ward | |
| 2002/0197256 A1 | 12/2002 | Grewal | |
| 2003/0115614 A1 | 6/2003 | Kanda et al. | |
| 2003/0118592 A1 | 6/2003 | Ledbetter et al. | |
| 2003/0158389 A1 | 8/2003 | Idusogie et al. | |
| 2003/0161826 A1 | 8/2003 | Arnason et al. | |
| 2003/0166868 A1 | 9/2003 | Presta et al. | |
| 2003/0190311 A1 | 10/2003 | Dall'Acqua et al. | |
| 2003/0190317 A1 | 10/2003 | Baca et al. | |
| 2003/0203409 A1 | 10/2003 | Kim | |
| 2003/0206899 A1 | 11/2003 | Ferrara et al. | |
| 2004/0002587 A1 | 1/2004 | Watkins et al. | |
| 2004/0093621 A1 | 5/2004 | Shitara et al. | |
| 2004/0132101 A1 | 7/2004 | Lazar et al. | |
| 2004/0191244 A1 | 9/2004 | Presta | |
| 2004/0191256 A1 | 9/2004 | Raju | |
| 2004/0191265 A1 | 9/2004 | Schenerman et al. | |
| 2004/0214988 A1 | 10/2004 | Tirrell et al. | |
| 2004/0228856 A1 | 11/2004 | Presta | |
| 2005/0014934 A1 | 1/2005 | Hinton et al. | |
| 2005/0031613 A1 | 2/2005 | Nakamura et al. | |
| 2005/0031626 A1 | 2/2005 | Stevenson | |
| 2005/0032114 A1 | 2/2005 | Hinton et al. | |
| 2005/0037000 A1 | 2/2005 | Stavenhagen et al. | |
| 2005/0054832 A1 | 3/2005 | Lazar et al. | |
| 2005/0079574 A1 | 4/2005 | Bond | |
| 2005/0079605 A1 | 4/2005 | Umana et al. | |
| 2005/0112126 A1 | 5/2005 | Baca et al. | |
| 2005/0118174 A1 | 6/2005 | Presta | |
| 2005/0119455 A1 | 6/2005 | Fuh et al. | |
| 2005/0136051 A1 | 6/2005 | Scallon | |
| 2005/0142133 A1 | 6/2005 | Lazar et al. | |
| 2005/0152894 A1 | 7/2005 | Krummen et al. | |
| 2005/0186208 A1 | 8/2005 | Fyfe et al. | |
| 2005/0227324 A1 | 10/2005 | Huang et al. | |
| 2005/0233382 A1 | 10/2005 | Presta | |
| 2005/0249723 A1 | 11/2005 | Lazar | |
| 2005/0260186 A1 | 11/2005 | Bookbinder et al. | |
| 2005/0266000 A1 | 12/2005 | Bond | |
| 2005/0272916 A1 | 12/2005 | Hanai et al. | |
| 2005/0276799 A1 | 12/2005 | Hinton et al. | |
| 2005/0276805 A1 | 12/2005 | Hanai et al. | |
| 2006/0009360 A1 | 1/2006 | Pifer et al. | |
| 2006/0018911 A1 | 1/2006 | Ault-Riche et al. | |
| 2006/0024292 A1 | 2/2006 | Gerngross et al. | |
| 2006/0024298 A1 | 2/2006 | Lazar et al. | |
| 2006/0024300 A1 | 2/2006 | Adams et al. | |
| 2006/0024304 A1 | 2/2006 | Gerngross et al. | |
| 2006/0025576 A1 | 2/2006 | Miller et al. | |
| 2006/0029604 A1 | 2/2006 | Gerngross et al. | |
| 2006/0034828 A1 | 2/2006 | Gerngross et al. | |
| 2006/0034829 A1 | 2/2006 | Gerngross et al. | |
| 2006/0034830 A1 | 2/2006 | Gerngross et al. | |
| 2006/0067930 A1 | 3/2006 | Adams et al. | |
| 2006/0074225 A1 | 4/2006 | Chamberlain et al. | |
| 2006/0104968 A1 | 5/2006 | Bookbinder et al. | |
| 2006/0121032 A1 | 6/2006 | Dahiyat et al. | |
| 2006/0134709 A1 | 6/2006 | Stavenhagen et al. | |
| 2006/0140934 A1 | 6/2006 | Gegg et al. | |
| 2006/0153838 A1 | 7/2006 | Watkins et al. | |
| 2006/0160996 A9 | 7/2006 | Lazar et al. | |
| 2006/0173170 A1 | 8/2006 | Chamberlain et al. | |
| 2006/0194290 A1 | 8/2006 | Presta | |
| 2006/0194291 A1 | 8/2006 | Presta | |
| 2006/0194954 A1 | 8/2006 | Idusogie et al. | |
| 2006/0194957 A1 | 8/2006 | Presta | |
| 2006/0198840 A1 | 9/2006 | Dall'Acqua et al. | |
| 2006/0235208 A1 | 10/2006 | Lazar et al. | |
| 2006/0246004 A1 | 11/2006 | Adams et al. | |
| 2006/0275282 A1 | 12/2006 | Moore et al. | |
| 2006/0275283 A1 | 12/2006 | Van Vlijmen et al. | |
| 2006/0280747 A1 | 12/2006 | Fuh et al. | |
| 2007/0003546 A1 | 1/2007 | Lazar et al. | |
| 2007/0009523 A1 | 1/2007 | Presta | |
| 2007/0020260 A1 | 1/2007 | Presta | |
| 2007/0020267 A1 | 1/2007 | Fuh et al. | |
| 2007/0036806 A1 | 2/2007 | Glaesner et al. | |
| 2007/0041966 A1 | 2/2007 | Armour et al. | |
| 2007/0048300 A1 | 3/2007 | Taylor et al. | |
| 2007/0053901 A1 | 3/2007 | Lazar et al. | |
| 2007/0061900 A1 | 3/2007 | Murphy et al. | |
| 2007/0117126 A1 | 5/2007 | Sidhu et al. | |
| 2007/0122406 A1 | 5/2007 | Chamberlain et al. | |
| 2007/0135620 A1 | 6/2007 | Chamberlain et al. | |
| 2007/0141065 A1 | 6/2007 | Fuh et al. | |
| 2007/0148171 A1 | 6/2007 | Lazar et al. | |
| 2007/0160597 A1 | 7/2007 | Lazar et al. | |
| 2007/0160598 A1 | 7/2007 | Dennis et al. | |
| 2007/0161783 A1 | 7/2007 | Barbosa et al. | |
| 2007/0166309 A1 | 7/2007 | Lazar et al. | |
| 2007/0202098 A1 | 8/2007 | Lazar et al. | |
| 2007/0219133 A1 | 9/2007 | Lazar et al. | |
| 2007/0224189 A1 | 9/2007 | Lazar et al. | |
| 2007/0224192 A1 | 9/2007 | Lazar et al. | |
| 2007/0231329 A1 | 10/2007 | Lazar et al. | |
| 2007/0237764 A1 | 10/2007 | Birtalan et al. | |
| 2007/0237765 A1 | 10/2007 | Lazar et al. | |
| 2007/0237766 A1 | 10/2007 | Lazar et al. | |
| 2007/0237767 A1 | 10/2007 | Lazar et al. | |
| 2007/0238665 A1 | 10/2007 | Lazar et al. | |

(56) References Cited

U.S. PATENT DOCUMENTS

| | | |
|---|---|---|
| 2007/0243188 A1 | 10/2007 | Lazar et al. |
| 2007/0248602 A1 | 10/2007 | Lazar et al. |
| 2007/0248603 A1 | 10/2007 | Lazar et al. |
| 2007/0286859 A1 | 12/2007 | Lazar et al. |
| 2007/0292936 A1 | 12/2007 | Barthelemy et al. |
| 2008/0051563 A1 | 2/2008 | Lazar et al. |
| 2008/0057056 A1 | 3/2008 | Lazar et al. |
| 2008/0069820 A1 | 3/2008 | Fuh et al. |
| 2008/0095762 A1 | 4/2008 | Presta |
| 2008/0138338 A1 | 6/2008 | Idusogie et al. |
| 2008/0152649 A1 | 6/2008 | Chamberlain et al. |
| 2008/0154025 A1 | 6/2008 | Lazar et al. |
| 2008/0161541 A1 | 7/2008 | Lazar et al. |
| 2008/0181890 A1 | 7/2008 | Lazar et al. |
| 2008/0206242 A1 | 8/2008 | Lawrence et al. |
| 2008/0274105 A1 | 11/2008 | Presta |
| 2008/0274108 A1 | 11/2008 | Presta |
| 2009/0041770 A1 | 2/2009 | Chamberlain et al. |
| 2009/0060911 A1 | 3/2009 | Ravetch |
| 2009/0068182 A1* | 3/2009 | Young et al. ............... 424/133.1 |
| 2009/0148441 A1 | 6/2009 | Gillies |
| 2009/0163699 A1 | 6/2009 | Chamberlain et al. |
| 2010/0166740 A1 | 7/2010 | Endl et al. |
| 2010/0166749 A1 | 7/2010 | Presta |
| 2010/0255013 A1 | 10/2010 | Presta |
| 2011/0052584 A1 | 3/2011 | Ravetch |
| 2011/0086050 A1 | 4/2011 | Presta |
| 2011/0293632 A1 | 12/2011 | Presta |

FOREIGN PATENT DOCUMENTS

| | | |
|---|---|---|
| EP | 0 425 235 B1 | 9/1996 |
| EP | 0 811 691 B1 | 12/1997 |
| EP | 1176195 A1 | 1/2002 |
| EP | 0 666 868 B1 | 4/2002 |
| EP | 1 270 595 B1 | 1/2003 |
| EP | 1331266 A1 | 7/2003 |
| EP | 1331266 A4 | 7/2003 |
| EP | 1 498 491 A1 | 1/2005 |
| EP | 1 498 491 A4 | 1/2005 |
| EP | 1 068 241 B1 | 10/2007 |
| EP | 1 692 182 B1 | 4/2010 |
| WO | 88/07089 A1 | 9/1988 |
| WO | 93/01161 A1 | 1/1993 |
| WO | 93/16185 A2 | 8/1993 |
| WO | 93/16185 A3 | 8/1993 |
| WO | 93/22332 A2 | 11/1993 |
| WO | 93/22332 A3 | 11/1993 |
| WO | 94/08027 A1 | 4/1994 |
| WO | 94/10202 | 5/1994 |
| WO | 94/11026 A2 | 5/1994 |
| WO | 94/11026 A3 | 5/1994 |
| WO | 94/29351 A2 | 12/1994 |
| WO | 94/29351 A3 | 12/1994 |
| WO | 93/30046 | 10/1996 |
| WO | 96/32478 A1 | 10/1996 |
| WO | 97/28267 A1 | 8/1997 |
| WO | 97/30087 A1 | 8/1997 |
| WO | 97/34631 A1 | 9/1997 |
| WO | 97/43316 A1 | 11/1997 |
| WO | 97/44362 A1 | 11/1997 |
| WO | 98/23289 A1 | 6/1998 |
| WO | 98/45332 | 10/1998 |
| WO | 98/48032 A2 | 10/1998 |
| WO | 98/48032 A3 | 10/1998 |
| WO | 98/52975 A1 | 11/1998 |
| WO | 98/58964 A1 | 12/1998 |
| WO | 99/22764 A1 | 5/1999 |
| WO | 99/43713 A1 | 9/1999 |
| WO | 95/51642 A1 | 10/1999 |
| WO | 99/54342 A1 | 10/1999 |
| WO | 99/58572 A1 | 11/1999 |
| WO | 00/09560 A2 | 2/2000 |
| WO | 00/09560 A3 | 2/2000 |
| WO | 00/42072 A2 | 7/2000 |
| WO | 00/42072 A3 | 7/2000 |
| WO | 01/64754 A1 | 7/2001 |
| WO | 01/58957 A2 | 8/2001 |
| WO | 01/58957 A3 | 8/2001 |
| WO | 02/060919 | 8/2002 |
| WO | 02/060919 A2 | 8/2002 |
| WO | 03/035835 A2 | 5/2003 |
| WO | 03/073238 A2 | 9/2003 |
| WO | 03/073238 A3 | 9/2003 |
| WO | 2004/004662 A2 | 1/2004 |
| WO | 2004/004662 A3 | 1/2004 |
| WO | 2004/029207 A2 | 4/2004 |
| WO | 2004/029207 A3 | 4/2004 |
| WO | 2004/035752 A2 | 4/2004 |
| WO | 2004/035752 A3 | 4/2004 |
| WO | 2004/063351 A2 | 7/2004 |
| WO | 2004/092219 A2 | 10/2004 |
| WO | 2004/092219 A3 | 10/2004 |
| WO | 2004/099249 A2 | 11/2004 |
| WO | 2005/012359 A2 | 2/2005 |
| WO | 2005/018572 A2 | 3/2005 |
| WO | 2005/018572 A3 | 3/2005 |
| WO | 2005/035727 A2 | 4/2005 |
| WO | 2005/035727 A3 | 4/2005 |
| WO | 2005/037867 A1 | 4/2005 |
| WO | 2005/040217 A2 | 5/2005 |
| WO | 2005/040217 A8 | 5/2005 |
| WO | 2005/044853 A2 | 5/2005 |
| WO | 2005/047327 A2 | 5/2005 |
| WO | 2005/047327 A8 | 5/2005 |
| WO | 2005/074524 A2 | 8/2005 |
| WO | 2005/074524 A3 | 8/2005 |
| WO | 2005/100402 A1 | 10/2005 |
| WO | 2005/123780 A2 | 12/2005 |
| WO | 2005/123780 A3 | 12/2005 |
| WO | 2006/020114 A2 | 2/2006 |
| WO | 2006/020114 A3 | 2/2006 |
| WO | 2006/029879 A2 | 3/2006 |
| WO | 2006/029879 A3 | 3/2006 |
| WO | 2006/031370 A2 | 3/2006 |
| WO | 2006/044908 A2 | 4/2006 |
| WO | 2006/044908 A3 | 4/2006 |
| WO | 2006/047350 A2 | 5/2006 |
| WO | 2006/047350 A3 | 5/2006 |
| WO | 2006/053301 A2 | 5/2006 |
| WO | 2006/053301 A3 | 5/2006 |
| WO | 2006/053301 A9 | 5/2006 |
| WO | 2006/076594 A2 | 7/2006 |
| WO | 2006/076594 A3 | 7/2006 |
| WO | 2009/006520 A1 | 1/2009 |
| WO | 2009/058492 A2 | 5/2009 |
| WO | 2009/058492 A3 | 5/2009 |
| WO | 2009/073160 A1 | 6/2009 |
| WO | 2009/086320 A1 | 7/2009 |
| WO | 2009/089004 A1 | 7/2009 |
| WO | 2009/100309 A2 | 8/2009 |
| WO | 2009/100309 A3 | 8/2009 |
| WO | 2010/045193 A1 | 4/2010 |
| WS | 98/33924 A1 | 8/1998 |

OTHER PUBLICATIONS

Boerner et al., "Production of antigen-specific human monoclonal antibodies from in vitro-primed human splenocytes" J Immunol. 147 (1):86-95 (Jul. 1, 1991).

Brennan et al., "Preparation of bispecific antibodies by chemical recombination of monoclonal immunoglobulin $G_1$ fragments" Science 229:81-83 (1985).

Bruggemann et al., "Comparison of the effector functions of human immunoglobulins using a matched set of chimeric antibodies" J Exp Med 166(5):1351-61 (Nov. 1987).

Burton, D., "Immunoglobulin G: Functional sites" Mol Immunol 22(3):161-206 (1985).

Capel et al., "Heterogeneity of human IgG receptors" Immunomethods 4: 25-34 (1994).

Carter et al., "Humanization of an anti-p185 HER2 antibody for human cancer therapy" P Natl Acad Sci USA 89:4285-4289 (May 1992).

(56) References Cited

OTHER PUBLICATIONS

Carter et al., "Improved oligonucleotide site-directed mutagenesis Using M13 vectors" Nucl Acids Res 13(12):4431-4443 (1985).
Chari et al., "Immunoconjugates containing novel maytansinoids: Promising anticancer drugs" Cancer Res 52:127-131 (Jan. 1992).
Charlton, K.A., "Expression and isolation of recombinant antibody fragments in E. coli" Method Molec Biol 248:245-254 (2003).
Chen et al., "Selection and analysis of an optimzed anti-VEGF antibody: crystal structure of an affinity-matured Fab in conmplex with antigen" J Mol Biol 293(4):865-881 (1999).
Chin and Schultz, "In vivo photocrosslinking with unnatural amino acid mutagenesis" Chembiochem 11: 1135-1137 (2002).
Chin et al., "Addition of a photocrosslinking amino acid to the genetic code of Escherichia coli" P Natl Acad Sci USA 99(17):11020-11024 (Aug. 2002).
Chin et al., "Addition of p-Azido-L-phenylalanine to the genetic code of Escherichia coli" J Am Chem Soc 124:9026-9027 (2002).
Chothia et al., "Canonical structures for the hypervariable regions of immunoglobulins" J Mol Biol 196:901-917 (1987).
Chowdhury, "Engineering hot spots for affinity enhancement of antibodies" Methods Molec Biol 207:179-196 (2008).
Clackson et al., "Making antibody fragments using phage display libraries" Nature 352:624-628 (Aug. 1991).
Clynes et al., "Fc receptors are required in passive and active immunity to melanoma" P Natl Acad Sci USA 95:652-656 (Jan. 1998).
Extended European Search Report in EP Appln. No. 11 160251, Sep. 14, 2011.
International Search Report and Written Opinion of the International Searching Authority on patentability for International Patent Application No. PCT/EP2012/055393, May 15, 2012.
Cragg et al., "Antibody specificity controls in vivo effector mechanisms of anti-CD20 reagents" Blood 103(7):2738-2743 (2004).
Cragg et al., "Complement-mediated lysis by anti-CD20 mAb correlates with segregation into lipid rafts" Blood 101(3):1045-1052 (2003).
Cunningham et al., "High-resolution epitope mapping of hGH-receptor interactions by alanine-scanning mutagenesis" Science 244:1081-1085 (Jun. 2, 1989).
Daeron, M., "Fc receptor biology" Annu Rev Immunol 15:203-234 (1997).
Dall'Acqua et al., "Antibody humanization by framework shuffling" Methods 36:43-60 (2005).
Davis et al., "Fc receptor homologs: news members of a remarkably diverse Fc receptor gene family" Immunological Reviews 190:123-136 (2002).
De Haas et al., "Fcγ receptors of phagocytes" J Lab Clin Med 126:330-341 (Oct. 1995).
De Reys et al., "Human platelet aggregation by murine monoclonal antiplatelet antibodies is subtype-dependent" Blood 81:1792-1800 (1993).
Dubowchik et al., "Doxorubicin immunoconfugates containing bivalent, lysosmally-cleavable dipeptide linkages" Bioorg Med Chem Lett 12: 1529-1532 (2002).
Edelman et al., "The Covalent structure of an entire γG immunoglobulin molecule" P Natl Acad Sci USA 63:78-85 (1969).
Ellman et al., "Biosynthetic method for introducing unnatural amino acids site-specifically into proteins" Meth Enzym 202:301-336 (1991).
Fellouse et al., "Synthetic antibodies from a four-amino-acid code: A dominant role for tyrosine in antigen recognition" P Natl Acad Sci USA 101(34):12467-12472 (Aug. 24, 2004).
Flatman et al., "Process analytics for purification of monoclonal antibodies" J Chromatogr 848:79-87 (2007).
Gazzano-Santoro et al., "A non-radioactive complement-dependent cytotoxicity assay for anti-CD20 monoclonal antibody" J Immunol Methods 20:163-171 (1997).
Gerngros, "Advances in the production of human therapeutic proteins in yeast and filamentous fungi" Nature Biotechnology 22(11):1409-1414 (Nov. 2004).
Goding Monoclonal Antibodies: Principles and Practice "Production and Application of Monoclonal Antibodies in Cell Biology, Biochemistry and Immunology" Academic Press,:56-103 (1986)
Griffiths et al., "Human anti-self antibodies with high specificity from phage display libraries" EMBO J 12(2):725-734 (Feb. 1993).
Gruber et al., "Efficient tumor cell lusis mediated by a bispecific single chain antibody expressed in Escherichia coli" J Immunol 152:5368-5374 (1994).
Guyer et al., "Immunoglobulin binding by mouse intestinal epithelial cell receptors" J Immunol 117(2)587-593 (Aug. 1976).
Hellstrom et al., "Antitumor Effects of L6, an IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Hinman et al., "Preparation and characterization of monoclonal antibody conjugates of the cakicheamicins: A novel and potent family of antitumor antibiotics"Cancer Res 53:3336-3342 (Jul. 15, 1993).
Holliger et al., "'Diabodies': Small bivalent and bispecific antibody fragment" P Natl Acad Sci USA 90:6444-6448 (Jul. 1993).
Hooogenboom and Winter, "By-passing immunisation. Human antibodies from synthetic repertoires and germline $V_H$ gene segments rearranged in vitro" J Mol Biol 227(2):381-388 (Sep. 20, 1992).
Hoogenboom, H., "Overview of antibody phage-display technology and its applications" Methods Mol Biol 178:1-37 (2002).
Hudson et al., "Engineered antibodies" Nature Medicine 9(1):129-134 (Jan. 2003).
Hutchins et al., "Improved biodistribution, tumor targeting, and reduced immunogenicity in mice with a immunogenicity in mice with a γ4 variant of Campath-1H4 variant of Campath-1H" P Natl Acad Sci USA 92:11980-11984 (Dec. 1995).
Idusogie et al., "Engineered antibodies with increased activity to recruit complement" J Immunol 166:2571-2575 (2001).
Jefferis and Lund, "Interaction sites on human IgG-Fc for FcγR: current models" Immunol Lett 82(1-2):57-65 ( 2002).
Jeffrey et al., "Dipeptide-based highly potent doxorubicin antibody conjugates" Bioorganic Med Chem Letters 16:358-362 ( 2006).
Kam et al., "Carbon nanotubes as multifunctional biological transporters and near-infrared agents for selective cancer cell destruction" P Natl Acad Sci USA 102(33):11600-11605 (Aug. 2005).
Kaneko et al., "Anti-inflammatory activity of immunoglobulin G resulting from Fc sialylation" Science 313:670-673 (Aug. 2006).
Kaneko et al., "Optimizing therapeutic antibody function progress with Fc domain engineering" Biodrugs 25(1):1-11 (2011) (Abstract only).
Kashmiri et al., "SDR grafting—a new approach to antibody humanization" Methods 36:25-34 (2005).
King et al., "Monoclonal antibody conjugates of doxorubicin prepared with branched peptide linkers: Inhibition of aggregation by methoxytriethleneglycol chain" J Med Chem 45:4336-4343 (2002).
Klimka et al., "Human anti-CD30 recombinant antibodies by guided phage antibody selection using cell panning" Brit J Cancer 83(2):252-260 (2000).
Kohler et al., "Continuous cultures of fused cells secreting antibody of predefined specificity" Nature 256:495-497 (Aug. 7, 1975).
Kostelny et al., "Formation of a bispecific antibody by the use of leucine zippers" J Immunol 148(5):1547-1553 (Mar. 1, 1992).
Kozbor et al., "A human hybrid myeloma for production of human monoclonal antibodies" J Immunol 133(6):3001-3005 (Dec. 1984).
Lee et al., "Bivalent antibody phage display mimics natural immunoglobulin" J Immunol Methods 284:119-132 (2004).
Lee et al., "High-affinity human antibodies from phage-displayed synthetic Fab libraries with a single framework scaffold" J Mol Biol 340:1073-1093 (2004).
Li et al., "Human antibodies for immunotherapy development generated via a human B cell hybridoma technology" P Natl Acad Sci USA 103(10):3557-62 (Mar. 2006).
Li et al., "Optimization of humanized IgGs in glycoengineered Pichia pastoris" Nat Biotechnol 24(2):210-215 (Feb. 2006).
Lode et al., "Targeted therapy with a novel enediyene antibiotic calicheamicin $\theta^I_1$ effectively suppresses growth and dissemination

(56) References Cited

OTHER PUBLICATIONS of liver metastases in a syngeneic model murine neuroblastoma" Cancer Res 58:2925-2928 (Jul. 15, 1998).
Lonberg, "Fully human antibodies from transgenic mouse and phage display platforms" Current Opin Immunol 20:450-459 (2008).
Lonberg, N., "Human antibodies from transgenic animals" Nat Biotechnol 23(9):1117-1125 (Sep. 2005).
Marks and Bradbury Methods Mol Biol, Antibody Engineering "Selection of human antibodies from phage display libraries" Benny K. C. Lo,Humana Press, vol. 248:161-176 (2004).
Marks et al., "By-passing immunization. Human antibodies from V-gene libraries displayed on phage" J Mol Biol 222:581-597 (1991).
Marks et al., "By-passing immunization: Building high affinity human antibodies by chain shuffling" Bio/Technology 10:779-783 (Jul. 1992).
Mather et al., "Culture of testicular cells in hormone-supplemented serum-free medium" Ann NY Acad Sci 383:44-68 (1982).
Mather, "Establishment and characterization of two distinct mouse testicular epithelial cell lines" Biol Reprod 23:243-252 (1980).
McCafferty et al., "Phage antibodies: filamentous phage displaying antibody variable domains" Nature 348:552-554 (Dec. 6, 1990).
Milstein et al., "Hybrid hybridomas and their use in immunohistochemistry" Nature 305:537-540 (Oct. 6, 1983).
Morrison et al., "Chimeric human antibody molecules: Mouse antigen-binding domains with human constant region domains" P Natl Acad Sci USA 81:6851-6855 (Nov. 1984).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies" P Natl Acad Sci USA 97(2):829-34 (Jan. 18, 2000).
Ni, Xiandai Mianyixue ((Abstract only)), 26(4):265-168 (2006).
Noren et al., "A general method for site-specific incorporation of unnatural amino acids into proteins" Science 244(4901):182-188 (Apr. 14, 1989).
Oganesyan et al., "Structural characterization of a human Fc fragment engineered for lack of effector functions" Acta Cryst D64:700-704 (2008).
Osbourn et al., "From rodent reagent to human therapeutics using antibody guided selection" Methods 36:61-68 (2005).
O'Sullivan et al., "Methods for the preparation of enzyme-antibody conjugates for use in enzyme immunoassay" Method Enzymol 73:147-166 (1981).
Padlan, "A possible procedure for reducing the immunogenicity of antibody variable domains while preserving their ligand-binding properties" Mol Immunol 28(4/4):489-498 (1991).
Petkova et al., "Enhanced half-life of genetically engineered human IgG1 antibodies in a humanized FcRn mouse model: potential application in humorally mediated autoimmune disease" Int Immunol 18(12):1759-69 (Dec. 2006).
Pluckthun, A. The Pharmacology of Monoconal Antibodies: Handbook of Pharmacology "Antibodies from *Escherichia coli*" (Chapter 11), Resenberg and Moore, eds., Berlin:Springer-Verlag, vol. 113:269-315 (1994).
Portolano et al., "Lack of promiscuity in autoantigen-specific H and L chain combinations as revealed by human H and L chain 'Roulette'" J Immunol 150(3):880-887 (Feb. 1993).
Presta et al., "Humanization of an antibody directed against IgE" J Immunol 151(5):2623-2632 (Sep. 1993).
Presta et al., "Humanization an anti-vascular endothelial growth factor monoclonal antibody for the therapy of solid tumors and other disorders" Cancer Res 54:4593-4599 (Oct. 1997).
Queen et al., "A humanized antibody that binds to the interleukin 2 receptor" P Natl Acad Sci USA 86(24):10029-10033 (Dec. 1989).
Raghavan and Bjorkman, "Fc receptors and their interactions with immunoglobulins" Annu Rev Cell Dev Biol 12:181-200 (1996).
Ravetch and Bolland, "IgG Fc receptors" Ann Rev Immunol 19:275-290 (2001).
Ravetch and Kinet, "Fc receptors" Annu Rev Immunol 9:457-492 (1991).
Riechmann et al., "Reshaping human antibodies for aherapy" Nature 332:323-327 (Mar. 1988).
Rosok et al., "A combinatorial library strategy for the rapid humanization of anticarcinoma BR96 fab" J Biol Chem 271(37):22611-22618 (Sep. 13, 1996).
Shields et al., "High resolution mapping of the binding site on human IgG1 for FcγRI, FcγRII, FcγRIII, and FcRn and design IgG1 variants with improved binding to the FcγR" J Biol Chem 276(9):6591-6604 (Mar. 2, 2001).
Sidhu et al., "Phage-displayed Antibody Libraries of Synthetic Heavy Chain Complementarity Determining Regions" J Mol Biol 338(2):299-310 (2004).
Sims et al., "A humanized CD18 antibody can block function without cell destruction" J Immunol 151(4):2296-2308 (Aug. 15, 1993).
Taylor et al., "Thrombosis and shock induced by activating antiplatelet antibodies in human FcγRIIA transgenic mice: the interplay among antibody, spleen, and Fc receptor" Blood 96(13):4254-4260 (Dec. 2000).
Tomiyama et al., "Response of human platelets to activating monoclonal antibodies: Important of FcγRII (CD32) phenotype and level of expression" Blood 80(9):2261-2268 (1992).
Torgov et al., "Generation of an intensely potent anthracycline by a monoclonal antibody—β-galactosidase conjugate" Bioconjugate Chem 16:717-21 (2005).
Traunecker et al., "Bispecific single chain molecules (Janusins) target cytotoxic lymphocytes on HIV infected cells" EMBO J 10(12):3655-3659 (1991).
Tutt et al., "Trispecific F(ab')$_3$ derivatives that use cooperative signaling via the TCR/CD3 complex and CD2 to activate and redirect resting cytotoxic T cells" J Immunol 147 (1):60-69 (Jul. 1991).
Urlaub et al., "Isolation of chinese hamster cell mutants deficient in dihydrofolate reductase activity" P Natl Acad Sci USA 77(7):4216-4220 (Jul. 1980).
Vallette et al., "Construction of mutant and chimeric genes using the polymerase chain reaction" Nucl Acids Res 17(2):723-733 (1989).
van Dijk and van de Winkel, "Human antibodies as next generation therapeutics" Curr Opin Chem Biol 5(4):368-74 (Aug. 2001).
Vitetta et al., "Redesigning Natures's Poisons to Create anti-Tumor Reagents" Science 238:1098-1104 (1987).
Vollmers and Brandlein, "Death by stress: natural IgM-induced apoptosis" Methods Find Exp Clin Pharmacol 27(3):185-191 (2005).
Vollmers and Brandlein, "The 'early birds': Natural IgM antibodies and immune surveillance" Histol Histopathol 20:927-937 (2005).
Wang and Schultz, "Expading the genetic code" Chem Commun:1-10 (2002).
Waterhouse et al., "Combinatorial infection and in vivo recombination: a strategy for making large phage antibody repertoires" Nucl Acids Res 21(9):2265-2266 (1993).
Wells et al., "Casette mutagenesis: An efficient method for generation of multiple mutations at defined sites" Gene 34:315-323 (1985).
White et al., "Antibody-targeted immunotherapy for treatment of malignancy" Ann Rev Med 52:125-145 (2001).
Winter et al., "Making antibodies by phage display technology" Annu Rev Immunol 12:433-455 (1994).
Wright and Morrison, "Effect of glycosylation on antibody function: Implications for genetic engineering" Trends Biotechnol 15:26-32 (1997).
Xu et al., "In vitro characterization of five humanized OKT3 effector function variant antibodies" Cell Immunol 200:16-26 (2000).
Yazaki et al., "Expression of recombinant antibodies in mammalian cell lines" Methods Molec Biol 248:255-268 (2004).
Zola, H. Monoclonal Antibodies: A Manual of Techniques "6"CRC Press,:147-158 (1987).
"International Search Report and Written Opinion for PCT/US2009/060443", Feb. 23, 2010.
Adamis, A. P. et al., "Inhibition of Vascular Endothelial Growth Factor Prevents Retinal Ischemia-Associated Iris Neovascularization in a Nonhuman Premate" Arch Ophthalmol-Chic 114(1):66-71 (1996).

(56) References Cited

OTHER PUBLICATIONS

Allan and Isliker, "Studies on the complement-binding site of rabbit immunoglobulin G-I. Modification of tryptophan residues and their role in anticomplementary activity of rabbit IgG" Immunochemistry 11(4):175-180 (Apr. 1974).

Angal et al., "A single amino acid substitution abolishes the heterogeneity of chimeric mouse/human (IgG4) antibody" Molecular Immunology 30(1):105-108 (Jan. 1993).

Armour et al., "Recombinant Human IgG Molecules Lacking Fcγ Receptor I Binding and Monocyte Triggering Activities" European Journal of Immunology. 29(8):2613-2624 (1999).

Artandi et al., "Monoclonal IgM rheumatoid factors bind IgG at a discontinuous epitope comprised of amino acid loops from heavy-chain constant-region domains 2 and 3" P Natl Acad Sci USA 89(1):94-98 (Jan. 1, 1992).

Bloom et al., "Interchain disulfide bond in the core hinge region of human IgG4" Protein Sci 6:407-415 (1997).

Bolland et al., "SHIP modulates immune receptor responses by regulating membrane association Btk" Immunity 8(4):509-516 (Apr. 1998).

Borgstrom, P. et al., "Complete inhibition of angiogenesis and growt of microtumors by anti-vascular endthelial growth factor neutralizing antibody: novel concepts of angiostatic therapy from intravital videomicroscopy" Cancer Res 56(17):4032-4039 (Sep. 1, 1996).

Brambell, "The Transmission of Immunity from Mother to Young and the Catabolism of Immunoglobulins" Lancet 2:1087-1093 (Nov. 19, 1966).

Bredius et al., "Role of Neutrophil FcγRIIa (CD32) and FcγRIIIb (CD16) polymorphic forms in phagocytosis of human IgG1- and IgG3-opsonized bacteria and erythrocytes" Immunology 83(4):624-630 (Dec. 1994).

Brekke et al., "Human IgG Isotype-Specific Amino Acid Residues Affecting Complement-Mediated Cell Lysis and Phagocytosis." European Journal of Immunology 24(10):2542-2547 (Oct. 1994).

Brekke et al., "Structure-Function Relationships of Human IgG" The Immunologist 2:125-130 (1994).

Burmeister et al., "Crystal Structure of the Complex of Rat Neonatal Fc Receptor with Fc." Nature 372(6504):379-383 (Nov. 24, 1994).

Burton and Woof, "Human Antibody Effector Function" Advances in Immunology 51:1-84 (1992).

Burton et al., "Molecular recognition of antibody (IgG) by cellular Fc receptor (FcRI)" Molecular Immunology 25(11):1175-1181 (1988).

Burton et al., "The C1q Receptor Site on Immunoglobulin G." Nature 288(5789):338-344 (Nov. 27, 1980).

Canfield and Morrison, "The Binding Affinity of Human IgG for its High Affinity Fc Receptor is Determined by Multiple Amino Acids in the $C_H2$ Domain and is Modulated by the Hinge Region." J. Experimental Medicine 173(6):1483-1491 (Jun. 1, 1991).

Capon et al., "Designing CD4 Immunoadhesins for AIDS Therapy" Nature 337:525-531 (Feb. 9, 1989).

Carter et al., "Humanization of Anti-p185$^{HER2}$ Antibody for Human Cancer Therapy" P Natl Aad Sci USA 89(10):4285-4289 (May 1992).

Chappel et al., "Identification of Secondary FcγRI Binding Site within a Genetically Engineered Human IgG Antibody" Journal of Biological Chemistry 268:25124-25131 (1993).

Chappel et al., "Identification of the Fcγ Receptor Class I Binding site in Human IgG Through the use of Recombinant IgG1/IgG2 Hybrid and Point Mutated Antibodies." Proc. Natl. Acad. Sci. USA 88(20):9036-9040 (Oct. 15, 1991).

Clark, "IgG effector mechanisms" Chem Immunol. 65:88-110 (1997).

Clynes and Ravetch, "Cytotoxic antibodies trigger inflammation through Fc receptors" Immunity 3(1):21-26 (Jul. 1995).

Clynes et al., "Modulation of immune complex-induced Inflammation in vivo by the coordinate expression of activation and inhibitory Fc receptors" Journal of Experimental Medicine 189(1):179-185 (Jan. 4, 1999).

Clynes et al., "Uncoupling of immune complex formation and kidney damage in autoimmune glomerulonephritis" Science 279(5353):1052-1054 (Feb. 13, 1998).

Clynes et al., "Fc receptors are required in passive and active immunity to melanoma" P Natl Acad Sci USA 95(2):652-656 (Jan. 1998).

Cosimi, "Clinical Development of Orthoclone OKT3" Transplantation Proceedings 19(2 Suppl 1):7-16 (Apr. 1987).

Dall'Acqua et al., "Modulation of the effector functions of a human IgG1 through engineering of its hinge region" J Immunol 177:1129-38 (2006).

Dall'Acqua et al., "Increasing the affinity of a human IgG1 for the neonatal Fc receptor: biological consequences" J Immunol 169(9):5171-5180 (Nov. 1, 2002), Dall'Acqua et al., "Properties of human IgG1s engineered for enhanced binding to the neonatal Fc receptor (FcRn)" J Biol Chem 281(33):23514-24 (Aug. 2006).

Datta-Mannan et al., "Humanized IgG1 variants with differential binding properties to the neonatal Fc receptor: relationship to pharmacokinetics in mice and primates" Drug Metab Dispos 35(1):86-94 (Jan. 2007).

Datta-Mannan et al., "Monoclonal antibody clearance. Impact of modulating the interaction of IgG with the neonatal Fc receptor" J Biol Chem 282(3):1709-17 (Jan. 19, 2007).

Deisenhofer, J, "Crystallographic Refinement and Atomic Models of a Human Fc Fragment and Its Complex with Fragment B of Protein A from *Straphylococcus aureus* at 2.9- and 2.8-A Resolution" Biochemistry 20(9):2361-2370 (1981).

Duncan and Winter, "The Binding Site for Clq on IgG" Nature 332:738-740 (Apr. 21, 1988).

Duncan et al., "Localization of the Binding Site for the Human High-Affinity Fc Receptor on IgG." Nature 332:563-564 (Apr. 7, 1988).

Eccles et al., "Monoclonal antibodies targeting cancer: 'magic bullets' or just the trigger?" Breast Cancer Research 3(2):86-90 (2001).

El-Amine et al., "In vivo induction of tolerance by an Ig peptide is not affected by the deletion of FcR or a mutated IgG Fc fragment" Int Immunol. 14(7):761-6 (Jul. 2002).

Ferrara et al., "Clinical applications of angiogenic growth factors and their inhibitors" Nat Med 5(12):1359-1364 (Dec. 1999).

Fridman, W., "Fc receptors and immunoglobulin binding factors" FASEB Journal 5(12):2684-2690 (Sep. 1991).

Fundamental Immunology, Paul, W. E., 2nd edition, New York:Raven Press pp. 60 and 61 (1989).

Gergely et al., "Fc Receptors on Lymphocytes and K Cells." Biochemical Society Transactions 12(5):739-743 (Oct. 1984).

Ghebrehiwet et al., "Isolation, cDNA cloning, and overexpression of a 33-kD cell surface glycoprotein that binds to the globular "heads" of C1q" Journal of Experimental Medicine 179(6):1809-1821 (Jun. 1, 1994).

Ghetie and Ward, "FcRn: the MHC Class I-related receptor that is more than IgG transporter" Immunol Today 18(12):592-598 (Dec. 1997).

Ghetie et al., "Abnormally short serum half-lives of IgG in β2-microglobulin-deficient mice" European Journal of Immunology 26(3):690-696 (Mar. 1996).

Ghetie et al., "Increasing the serum persistence of an IgG fragment by random mutagenesis" Nat Biotechnol 15(7):637-640 (Jul. 1997).

Gillies et al., "MRI of the tumor microenvironment" J Magn Reson Imaging 16(4):430-50 (Oct. 2002).

Gorman et al., "Transient Production of Proteins Using an Adenovirus Transformed Cell Line" DNA Prot. Eng. Tech. 2(1):3-10 (1990).

Graham et al., "Characteristics of a Human Cell Line Transformed by DNA from Human Adenovirus Type 5" J. Gen. Virol. 36:59-72 (1977).

Greenwood et al., "Structural motifs involved in human IgG antibody effector functions" European Journal of Immunology 23(5):1098-1104 (May 1993).

Greenwood et al., "Engineering multiple-domain forms of the therapeutic antibody CAMPATH-1H: effects on complement lysis" Therapeutic Immunology 1(5):247-255 (Oct. 1994).

(56) References Cited

OTHER PUBLICATIONS

Guddat et al., "Three-dimensional structure of a human immunoglobulin with a hinge deletion" PNAS (USA) 90:4271-4275 (1993).
Gurbaxni and Morrison, "Development of new models for the analysis of Fc-FcRn interactions" Mol Immunol 43:1379-89 (2006).
Haagen et al., "Interaction of Human Monocyte Fcγ Receptors with Rat IgG2b: A New Indicator for the FcγRIIa (R-H131) Polymorphism" J. Immunol. 154:1852-1860 (1995).
Hadley et al., "The functional activity of FcγRII and FcγRIII on subsets of human lymphocytes" Immunology 76(3):446-451 (Jul. 1992).
Harlow and Lande Antibodies. A Laboratory Manual, New York:Cold Spring Harbor Laboratory pp. 321-358 (1988).
Harris et al., "Crystallographic Structure of an Intact IgG1 Monoclonal Antibody" Journal of Molecular Biology 275:861-872 (1998).
Harris et al., "Refined Structure of an Intact IgG2a Monoclonal Antibody" Biochemistry 36:1581-1597 (1997).
Hatta et al., "Association of Fcγ Receptor IIIB, But Not of Fcγ Receptor IIA and IIIA, Polymorphisms with Systemic Lupus Erythematosus in Japanese." Genes and Immunity 1:53-60 (1999).
Heiken et al., "T lymphocyte development in the absence of Fcε receptor Iγ subunit: analysis of thymic-dependent and independent αβ and γδ pathways" European Journal of Immunology 26(8):1935-1943 (Aug. 1996).
Henry et al., "Participation of the N-terminal region of Cε3 in the binding of human IgE to its high-affinity receptor FεRI" Biochemistry 36:15568-15578 (1997).
Hessell et al., "Fc receptor but not complement binding is important in antibody protection against HIV" Nature 449:101-105 (Sep. 6, 2007).
Hezareh et al., "Effector function activities of a panel of mutants of a broadly neutralizing antibody against human immunodeficiency virus type 1" J Virol. 75(24):12161-8 (Dec. 2001).
Hinton et al., "An engineered human IgG1 antibody with longer serum half-life" J Immunol 176(1):346-56 (2006).
Hinton et al., "Engineered human IgG antibodies with longer serum half-lives in primates" J Biol Chem 279(8):6213-6216 (Feb. 20, 2004).
Hogarth et al., "Characterization of FcR Ig-binding sites and epitope mapping" Immunomethods 4(1)17-24 (Feb. 1994).
Houck et al., "The Vascular Endothelial Growth Factor Family: Identification of a Fourth Molecular Species and Characterization of Alternative Splicing of RNA" Mol Endocrinol 5(12):1806-14 (1991).
Huizinga et al, "Binding Characteristics of Dimeric IgG Subclass Complexes to Human Neutrophils" Journal of Immunology 142:2359-2364 (1989).
Hulett et al., "Chimeric Fc Reveptors Identify Functional Domains of the Murine High Affinity Receptors for IgG" J. Immunol. 147:1863-1868 (1991).
Idusogie et al., "Engineered Antibodies with Increased Activity to Recruit Complement" Journal of Immunology 166(4):2571-2575 (Feb. 15, 2001).
Idusogie et al., "Mapping of the C1q Binding Site on Rituxan, A Chimeric Antibody with a Human IgG1 Fc" J Immunol 164(8):4178-4184 (2000).
Israel et al., "Increased clearance of IgG in mice that lack beta 2-microglobulin: possible protective role of FcRn" Immunology 89(4):573-8 (Dec. 1996).
Jaakkola et al., "In vivo detection of vascular adhesion protein-1 in experimental inflammation" American Journal of Pathology 157(2):463-471 (Aug. 2000).
Janeway et al. Immunobiology, The Immune System in health and Disease, CB Ltd and Garland Publishing Inc., NY & London pp. 3:29-3:30 (1994).
Jefferis et al., "Molecular Definition of Interaction Sites on Human IgG for Fc Receptors (huFcγR)"Molecular Immunology 27(12):1237-1240 (1990).

Jensen et al., "Rapid tumor lysis in a patient with B-cell chronic lymphocytic leukemia and lymphocytosis treated with an anti-CD20 monoclonal antibody (IDEC-C2B8, rituximab)" Annals of Hematology 77(1-2):89-91 (Jul.-Aug. 1998).
Jones et al., "The mechanism of intestinal uptake and transcellular transport of IgG in the neonatal rat" J Clin Invest. 51(11):2916-27 (Nov. 1972).
Kabat et al. Sequences of Proteins of Immunological Interest (Table of Contents, Introduction and Constant Region Sequences sections), 5th edition. Bethesda, MD:NIH, vol. 1:647-723 (1991).
Kamei et al., "Quantitative methods for developing Fc mutants with entended half-lives" Biotechnol Bioeng. 92(6):748-60 (Dec. 2005).
Kim et al., "The Vascular Endothelial Growth Factor Proteins: Identification of Biologically Relevant Regions by Neutralizing Monoclonal Antibodies" Growth Factors 7:53-64 (1992).
Kim et al., "Catabolism of the Murine IgG1 Molecule: Evidence That Both CH2-CH3 Domain Interfaces are Required for Persistence of IgG1 in the Circulation of Mice" Scandinavian Journal of Immunology 40(4):457-465 (1994).
Kim et al., "Identifying Amino Acid Residues that Influence Plasma Clearance of Murine IgG1 Fragments by Site-Directed Mutagenesis." European Journal of Immunology 24:542-548 (1994).
Kim et al., "Inhibition of Vascular Endothelial Growth Factor-Induced Angiogenesis Supresses Tumor Growth in vivo" Nature 362:841-844 (Apr. 29, 1993).
Kim et al., "Localization of the site of the murine IgG1 molecule that is involved in binding to the murine intestinal Fc receptor" Eur J Immunol 24:2429-2434 (1994).
Kim et al., "Mapping the site on human IgG for binding of the MHC class I-related receptor, FcRn" Eur J Immunol 29(9):2819-2825 (Sep. 1999).
Klagsbrun and D'Amore, "Regulators of angiogenesis" Ann Rev Physiol 53:217-239 (1991).
Koene et al., "FcγRIIIa-158V/F Polymorphism Influences the Binding of the IgG by Natural Killer Cell FcγRIIa, Independently of the FcγRIIIa-48L/R/H Phenotype" Blood 90(3):1109-1114 (1997).
Kratz et al., "Prodrugs of anthracyclines in cancer chemotherapy" Curr Med Chem 13:477-523 (2006).
Kunkel, T., "Rapid and efficient site-specific mutagenesis without phenotypic selection" P Natl Acad Sci USA 82:488-492 (Jan. 1985).
Lauvrak et al., "Identification and characterisation of C1q-binding phage displayed peptides" Biological Chemistry 378(12):1509-1519 (Dec. 1997).
Lazar et al., "Engineered antibody Fc variants with enhanced effector function" Proc Natl Acad Sci U S A. 103(11):4005-10 (Mar. 2006).
Lehrnbecher et al., "Variant genotypes of FcγRIIIA influence the development of Kaposi's sarcoma in HIV-infected men" Blood 95(7):2386-2390 (2000).
Lehrnbecher et al., "Variant Genotypes of the Low-Afinity Fcγ Receptors in Two Control Populations and a Review of Low-Affinity Fcγ Receptor Polymorphisms in Control and Disease Populations." Blood 94(12):4220-4232 (Dec. 15, 1999).
Leung et al., "Vascular Endothelial Growth Factor is Secreted Angiogenic Mitogen" Science 246:1306-1309 (Dec. 8, 1989).
Li et al., "Reconstitution of human FcγRIII cell type specificity in transgenic mice" Journal of Experimental Medicine 183(3):1259-1263 (Mar. 1, 1996).
Liang et al., "Cross-species vascular endothelial growth factor (VEGF)-blocking antibodies completely inhibit the growth of human tumor xenografts and measure the contribution of stromal VEGF" J Biol Chem 281(2):951-61 (Jan. 2006).
Lifely et al., "Glycosylation and Biological Activity of CAMPATH-1H Expressed in Different Cell Lines and Grown Under Different Culture Conditions." Glycobiology 5(8):813-822 (Dec. 1995).
Lorenz et al., "Strong Association Between the Responder Status of the FCγII Receptor and Recurrent Spontaneous Abortion." European Journal of Immunogenetics 22(5):397-401 (Oct. 1995).
Lucas, et al., "High-Level Production of Rcombinant Proteins in CHO Cells Using a Dicistronic DHFR Intron Expression Vector" Nucleic Acids Research 24(9):1774-1779 (1996).
Lund et al., "Human FcγRI and Fcγ RII interact with distinct but overlapping sites on human IgG" Journal of Immunology 147(8):2657-2662 (Oct. 15, 1991).

(56) References Cited

OTHER PUBLICATIONS

Lund et al., "Oligosaccharide-protein interactions in IGG can modulate recognition by Fcγ receptors" FASEB Journal 9:115-119 (1995).
Lund et al., "Multiple binding sites on the $C_H2$ domain of IgG for mourse FcγRII"Mol Immunol 29(1)53-59 (Jan. 1992).
Lund et al., "Multiple Interactions of the IgG with Its Core Oligosaccharide Can Modulate Recognition by Complement and Human Fcγ Receptor I and Influence the Synthesis of Its Oligosaccharide Chains" J Immunol 157:4963-4969 ( 1996).
Male, D. Immunology, An Illustrated Outline London:Gower Medical Publishing Ltd.,:21-24 ( 1986).
Martin et al., "Crystal structure at 2.8 A of an FcRn/heterodimeric Fc complex mechanism of PH-dependent binding" Molecular Cell 7(4):867-877 (Apr. 2001).
Maxwell et al., "Crystal structure of the human leukocyte Fc receptor, FcγRIIa" Nature Structural Biology 6(5):437-442 (May 1999).
McCarthy et al., "Bidirectional transcytosis of IgG by the rat neonatal Fc receptor expressed in a rat kidney cell line: a system to study protein transport across epithelia" J Cell Sci. 113:127-85 (Apr. 2000).
Medesan et al., "Comparative studies of rat IgG to further delineate the Fc:FcRN interacation site" European Journal of Immunology 28:2092-2100 (1998).
Medesan et al., "Delineation of the amino acid residues involved in transcytosis and catabolism of mouse IgG1" Journal of Immunology 158(5):2211-2217 (Mar. 1, 1997)
Medesan et al., "Localization of the site of the IgG molecule that regulates maternofetal transmission in mice" European Journal of Immunology 26(10):2533-2536 (Oct. 1996).
Melnyk et al., "Vascular endothelial growth factor promotes tumor dissemination by a mechanism distinct from its effect on primary tumor growth" Cancer Res 56(4):921-924 (Feb. 15, 1996).
Meng et al., "Green fluorescent protein as a second selectable markerfor selection of high producing clones from transfected CHO cells" Gene 242:201-207 (2000).
Mikayama et al., "Molecular cloning and functional expression of a cDNA encoding glycosylation-inhibiting factor" Proc. Natl. acad. Sci. USA 90(21):10056-10060 (Nov. 1, 1993).
Miller et al., "A Novel Role for the Fc Receptor γ Subunit: Enhancement of the FcγR Ligand Affinity" Journal of Experimental Medicine 183:2227-2233 (1996).
Morgan et al., "The N-terminal end of the $C_H2$ domain of chimeric human IgG1 anti-HLA-DR is necessary or C1q, FcγRI and FcγRIII binding" Immunology 86(2):319-324 (Oct. 1995).
Morris, "2 The receptor hypothesis of protein ingestion" Antigen Absorption by the Gut, W. A. Hemminggs, Baltimore: University park Press pp. 3-22 (1978).
Morrison et al., "Structural Determinants of Human IgG Function" Immunologist 2:119-124 (1994).
Nagarajan et al., "Ligand binding and phagocytosis by CD16 (Fc γ receptor III) isoforms. Phagocytic signaling by associated ζ and γ subunits in Chinese hamster ovary cells" Journal of Biological Chemistry 270(43):25762-25770 (Oct. 27, 1995).
Newkirk et al., "Rheumatoid factor avidity in patients with rheumatoid arthitis: identification of pathogenic RFs whcih correlate with disease parameters and with the gal(0) glycoform of IgG" Journal of Clinical Immunology 15(5):250-257 (Sep. 1995).
Newman et al., "Modification of the Fc region of a primatized IgG antibody to human CD4 retains its ability to modulate CD4 rceptors but does not deplete CD(+) T cells in chimpanzees" Clin Immunol 98(2):164-74 (Feb. 2001).
Ngo et al., "Computational Complexity and the Levinthal Pasradox" The Protein Folding Problem and Teritiary Structure Prediction, Merz & Le Grand, Boston:Birkhauser pp. 491-506 (1994).
Nieto et al., "Involvement of the Fcγ receptor IIIA genotypes in susceptibility to rheumatoid arthritis" Arthritis and Rheumatism 43(4):735-739 (2000).
Niu and Chiu, "FDA perspective on peptide formulation and stability issues" J Pharm Sci 87(11):1331-1334 (Nov. 1998).

Ober et al., "Exocytosis of IgG as mediated by the receptor, FcRn: an analysis at the single-molecule level" Proc Natl Acad Sci U S A. 101(30):11076-81 (Jul. 2004).
Ober et al., "Visualizing the site and dynamics of IgG salvage by the MHC class I-related receptor, FcRn" J Immunol. 172(4):2021-9 (Feb. 2004).
Okada et al., "Cutting Edge: Role of the inositol phosphatase SHIP in B cell reeptor-induced $Ca^{2+}$ oscillatory response" Journal of Immunology 161(10):5129-5132 (Nov. 15, 1998).
Okazaki et al., "Fucose depletion from human IgG1 oligosacharide enhances binding enthalpy and association rate between IgG1 and FcgammaRIIIa" J Mol Biol. 336(5):1239-1249 (Mar. 5, 2004).
Olafsen et al., "Tunable pharmacokinetics: modifying the in vivo half-life of antibodies by directed mutagenesis of the Fc fragment" Nat Protoc. 1(4):2048-60 (2006).
Ono et al., "Deletion of SHIP or SHP-1 reveals two distinct pathways for inhibitory signaling" Cell 90(2):293-301 (Jul. 25, 1997).
Ono et al., "Role of the inositol phosphatase SHIP in negative regulation of the immune system by the receptor FcγRIIB" Nature 383(6597):263-266 (Sep. 19, 1996).
Papac et al., "A high-throughput microscale method to release N-linked oligosaccharide from glycoproteins for matrix-assisted laser desorption/ionization time-of-flight mass spectrometric analysis" Glycobiology 8(5):463-472 (1998).
Papac et al., "Analysis of Acidic Oligosaccharides and Glycopeptides by Matrix-Assisted Laser Desorption/Ionization Time-of-Flight Mass Spectrometry" Anal. Chem. 68:3215-3223 (1996).
Popkov et al., "Human/mouse cross-reactive anti-VEGF receptor 2 recombinant antibodies selected from an immune b9 allotype rabbit antibody library" J Immunol Methods 288:149-164 (May 2004).
Popov et al., "The stoichiometry and affinity of the interaction of murine Fc fragments with the MHC class I-related receptor, FcRn" Molecular Immunology 33(6):521-530 (Apr. 1996).
Porges et al., "Novel Fcγ Receptor I Family Gene Products in Human Mononuclear Cells" J Clin. Invest. 90:2102-2109 (1992).
Prabhat et al., "Elucidation of intracellular recycling pathways leading to excytosis of the Fc receptor, FcRn, by using multifocal plane microscopy" Proc Natl Acad Sci U S A. 104(14):5889-94 (Apr. 2007).
Praetor et al., "Intracellular traffic of the MHC class I-like IgG Fc receptor, FcRn, expressed in epithelial MDCK cells" J Cell Sci. 112:2291-9 (Jul. 1999).
Presta et al., "Humanizaiton of an Anti-Vascular Endothelial Growth Factor Monoclonal Antibody for the Therapy of Solid Tumors and Other Disorders" Cancer Res 57(20):4593-4599 (Oct. 15, 1997).
Raghavan et al., "Analysis of the pH dependence of the neonatal Fc receptor/immunoglobulin G interaction using antibody and receptor variants" Biochemistry—US 34(45):14649-14657 (Nov. 14, 1995).
Ravetch and Clynes, "Divergent roles for Fc receptors and complement in vivo" Annual Review of Immunology 16:421-432 (1998).
Ravetch, J., "Fc receptor" Current Opinion in Immunology 9(1):121-125 (Feb. 1997).
Ravetch, J., "Fc receptor: rubor redux" Cell 78(4):553-560 (Aug. 26, 1994).
Reff et al., "Depletion of B Cells In vivo by a Chimeric Mouse Human Monoclonal Antibody to CD20" Blood 83(2):435-445 (1994).
Rodewald, "pH-dependent binding of immunoglobulins to intestinal cells of the neonatal rat" J Cell Biol 71(2):666-9 (Nov. 1976).
Roopenian and Akilesh, "FcRn: the neonatal Fc receptor comes of age" Nat Rev Immunol 7:715-725 (2007).
Roopenian et al., "The MHC class I-like IgG receptor controls perinatal IG transpport, IgG homeostasis, and fate of IgG-Fc-coupled drugs" J Immunol 170(7):3528-33 (Apr. 2003).
Sarmay et al., "Ligand Inhibiton Studies on the Role of Fc Receptors in Antibody-Dependent Cell-Mediated Cytotoxicity." Molecular Immunology 21(2):43-51 (Jan. 1984).
Sarmay et al., "Mapping and comparison of the interaction sites on the Fc region of IgG responsible for triggering antibody dependent cellular cytotoxicity (ADCC) through different types of human Fcγ receptor" Molecular Immunology 29(5):633-639 (May 1992).
Sato, "Molecular diagonsis of tumor angiogenesis and anti-angiogenic cancer therapy" Int J Clin Oncol 8(4):200-206 (Aug. 2003).

(56) References Cited

OTHER PUBLICATIONS

Sensel et al., "Amino acid differenves in the N-terminus of $C_H2$ influence the relative abilities of IgG2 and IgG3 to activate complement" Molecular Immunology 34(14):1019-1029 (Oct. 1997).
Shields et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-604 (Mar. 2, 2001).
Shores et al., "T cell development in mice lacking all T cell receptor ζ family members (ζ,η, and FcεRIγ)" Journal of Experimental Medicine 187(7):1093-1101 (Apr. 6, 1998).
Simon et al., "Consolidation treatment with chimeric anti-GD2-antibody ch14.18 in children older than 1 year with metastatic neuroblastoma" J Clin Oncol. 22(17):3549-57 (Sep. 2004).
Sondermann et al., "Crystal structure of the soluble form of the human Fcγ—receptor IIb: a new member of the immunoglobulin superfamily at 1.7 A resolution"EMBO Journal 18(5):1095-1103 (1999).
Sondermann et al., "The 3.2-A crystal structure of the human IgG1 Fc fragment-Fc gammaRIII complex" Nature 406(6793):267-273 (2000).
Song et al., "Influence of Tumor pH on Therapeutic Response" Cancer Drug Discovery and Development: Cancer Drug Resistance (2007).
Steplewski et al., "Biological activity of human-mouse IgG1, IgG2, IgG3, and IgG4 chimeric monoclonal antibodies with antitumor specificity" Proc. Natl. Acad. Sci. USA 85(13):4852-4856 (Jul. 1988).
Streit et al., "Angiogenesis, lymphangiogenesis, and melanoma metastasis" Oncogene 22(20):3172-3179 (May 19, 2003).
Strohmeier et al., "Neutrophil functional responses depend on immune complex valency" Journal of Leukocyte Biology 58(4):403-414 (Oct. 1995).
Strohmeier et al., "Role of the FcγR subclasses FcγRII and FcγRIII in the activation of human neutrophils by low and high valency immune complexes" Journal of Leukocyte Biology 58(4):415-422 (Oct. 1995).
Suzuki et al., "Distinct contribution of Fc receptors and angiotensin II-dependent pathways in anti-GBM glomerulonephritis" Kidney International 54(4):1166-1174 (Oct. 1998).
Sylvestre and Ravetch, "Fc receptors initiate the Arthus reaction: redefining the inflammatory cascade" Science 265(5175):1095-1098 (Aug. 19, 1994).
Sylvestre and Ravetch, "A dominant role for mast cell Fc receptors in the Arthus reaction" Immunity 5(4):387-390 (Oct. 1996).
Sylvestre et al., "Immunoglobulin G-mediated inflammatory responses develop normally in complement-deficient mice" Journal of Experimental Medicine 184(6):2385-2392 (Dec. 1, 1996).
Takai et al., "Augmented humoral and anaphylactic responses in FcγRII-deficient mice" Nature 379(6563):346-349 (Jan. 25, 1996).
Takai et al., "FcR γ chain deletion results in effector pleiotrophic cell defects" Cell 76(3):519-529 (Feb. 11, 1994).
Tamm et al., "The IgG binding site of human FcγRIIIB receptor involves CC' and FG loops of the membrane-proximal domain" Journal of Biological Chemistry 271(7):3659-3666 (Feb. 16, 1996).
Tao and Morrison, "Studies of Aglycosylated Chimeric Mouse-Human IgG: Role of Carbohydrate in the Structure and Effector Functions Mediated by the Human IgG Constant Region." J. of Immunology 143(8):2595-2601 (Oct. 15, 1989).
Tao et al., "Structural Features of Human Immunoglobulin G That Determine Isotype-Specific Differences in Complement Activation." J. Experimental Medicine 178(2):661-667 (Aug. 1, 1993).
Tao et al., "The differential ability of human IgG1 and IgG4 to activate complement is determined by COOH-terminal sequence of the $C_H2$ domain" Journal of Experimental Medicine 173(4):1025-1028 (Apr. 1991).
Tax et al., "Fc receptors for mouse IgG1 on human monocytes: polymorphism and role in antibody-induced T cell proliferation" Journal of Immunology 133(3):1185-1189 (Sep. 1984).

Taylor et al., "In vitro and in vivo acativites of OX40 (CD134)-IgG fusion protein isoforms with different levels of immune-effector functions" J Leukoc Biol. 72(3):522-9 (Sep. 2002).
Tejada et al., "Tumor-driven paracrine platelet-derived growth factor receptor alpha signaling is a key determinant of stromal cell recruitment in a model of human lung carcinoma" Clin Cancer Res 12(9):2676-88 (May 2006).
Tesar et al., "Ligand Valency affects transcytosis, recycling and intracellular trafficking mediated by the neonatal Fc receptor" Traffic 7(9):1127-42 (Sep. 2006).
Thommesen et al., "Lysine 322 in the human IgG3 C(H)2 domain is crucial for antibody dependent complement activation" Mol Immunol 37(16):995-1004 (Nov. 2000).
Ting et al., "Fcγ receptor acativation induces the tyrosine phosphorylation of both phospholipase C (PLC)-γ1 and PLC-γ2 in natural killer cells" Journal of Experimental Medicine 176(6):1751-1755 (Dec. 1, 1992).
Tonini et al., "Molecular basis of angiogenesis and cancer" Oncogene 22(42):6549-6556 (Sep. 29, 2003).
Tutt et al., "Monoclonal antibody therapy of B cell lymphoma: signaling activity on tumor cells appears more important than recruitment of effectors" Journal of Immunology 161(6):3176-3185 (Sep. 15, 1998).
Umana et al., "Engineerted Glycoforms of an Antineuroblastoma IgG1 with Optimized Antibody-Dependent Cellular Cytotoxic Acativity" Nature Biotechnology 17(2):176-180 (Feb. 1999).
Urfer et al., "High resolution mapping of the binding site TrkA for nerve growth factor and TrkC for neurotrophin-3 on the second immunoglobulin-like domain of the Trk reeptors" Journal of Biological Chemistry 273(10):5829-5840 (Mar. 6, 1998).
Van de Winkel and Anderson, "Biology of human immunoglobulin G Fc receptors" Journal of Leukocyte Biology 49(5):511-524 (May 1991).
Vance et al., "Binding of monomeric human IgG defines an expression polymorphism of RcγRIII on large granular lymphocyte/natural killer cells" Journal of Immunology 151(11):6429-6439 (Dec. 1, 1993).
Ward and Ghetie, "The Effector Functions of Immunoglobulins: Implications for Therapy." Therapeutic Immunology 2(2):77-94 (1995).
Warmerdam et al., "A Single Amino Acid in the Second Ig-Like Domain of the Human Fcγ Receptor II is Critical for Human IgG2 Binding" Journal of Immunology 147(4):1338-1343 (Aug. 15, 1991).
Warren et al., "Regulation by vascular endothelial growth factor of human colon cancer tumorigenesis in a mouse model of experimental liver metastasis" J. Clin. Invest. 95(4):1789-1797 (Apr. 1995).
Watt et al., "Site-specific glycosylation of an aglycosylated human IgG1-Fc antibody protein generates neoglycoproteins with enhanced function" Chem Biol. 10(9):807-14 (Sep. 2003).
Wawrzynczak et al., "Recombinant Mouse Monoclonal Antibodies with single Amino Acid Substitutions Affecting C1q and High Affinity Fc Receptor Binding Have Identical Serum Half-lives in the BALB/c Mouse" Molecular Immunology 29(2):221-227 (1992).
Weng et al., "Computational determination of the structure of rat Fc bound to the neonatal Fc receptor" Journal of Molecular Biology 282(2):217-225 (Sep. 18, 1998).
Werther et al., "Humanization of an Anti-Lymphocyte Function-Associated Antigen (LFA)-1 Monoclonal Antibody and Reengineering of the Humanized Antibody for Binding to Rhesus LFA-1" J. of Immunology 157:4986-4995 (1996).
Williams et al., "Heteroclitic polyclonal and monoclonal anti-Gm(a) and anti-Gm(g) human rheumatoid factors react with epitopes induced in Gm(a–), Gm(g–) IgG by interaction with antigen or by nonspecific aggregation" Journal of Immunology 149(5):1817-1824 (Sep. 1, 1992).
Woof et al., "Localisation of the Monocyte-Binding Region on Human Immunoglobulin G." Molecular Immunology 23(3):319-330 (Mar. 1986).
Wright and Morrison, "Effect of altered $C_H2$-associated carbohydrate structure on the functional properties and in vivo fate of chimeric mouse-human immunoglobulin G1" Journal of Experimental Medicine 180(3):1087-1096 (Sep. 1, 1994).

(56) References Cited

OTHER PUBLICATIONS

Wu et al., "A Novel Polymorphism of FcγRIIIa (CD16) Alters Receptor Function and Predisposes to Autoimmune Disease." Journal of Clinical Investigation 100(5):1059-1070 (Sep. 1, 1997).

Xu et al., "In vitro characterization of five humanized OKT3 effector function variant antibodies" Cellular Immunology 200(1):16-26 (2000).

Xu et al., "Residue at position 331 in the IgG1 and IgG4 CH2 domains contributes to their differential ability to bind and activate complement" Journal of Biological Chemistry 269(5):3469-3474 (Feb. 4, 1994).

Xu et al., "The N-Terminal Sequence of the $C_H2$ Domain Controls the Differential Ability of Human IgG1 and IgG2 to Activate Complement." Journal of Immunology (abstract No. 862) 150(8):152A (Apr. 15, 1993.

Yap et al., "Human Fc Gamma Receptor IIa (FcγRIIA) Genotyping and Association with Systemic Lupus Erythematosus (SLE) in Chinese and Malays in Malaysia." Lupus 8(4):305-310 (1999).

Yeung et al., "Engineering Human IgG1 Affinity to Human Neonatal Fc Receptor: Impact of Affinity Improvement on Pharmacokinetics in Primates" Journal of Immunology 182:7663-7671 (2009).

Yuan et al., "Antibody-mediated modulation of *Cryptococcus neoformans* infection is dependent on distinct Fc receptor functions and IgG subclases" Journal of Experimental Medicine 187(4):641-648 (Feb. 16, 1998).

Zheng et al., "Administration of noncytolytic IL-10/Fc in murine models of lipoppolysaccharide-induced septic shock and allogeneic islet transplantation" J Immunol 154(10):5590-600 (May 1995).

\* cited by examiner

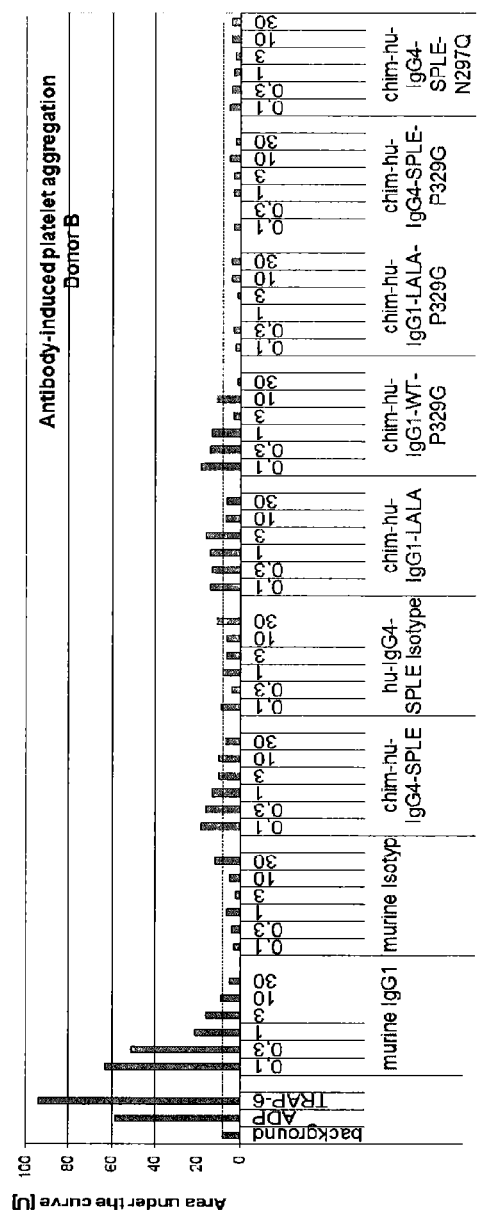

US 8,969,526 B2

ANTIBODY FC VARIANTS

CROSS-REFERENCE TO RELATED APPLICATIONS

This application claims the benefit of priority under 35 USC §119 of European patent application number 11160251.2, filed on Mar. 29, 2011, which is hereby incorporated by reference in its entirety.

FIELD OF THE INVENTION

The present invention concerns polypeptides comprising variants of an Fc region. More particularly, the present invention concerns Fc region-containing polypeptides that have altered effector function as a consequence of one or more amino acid substitutions in the Fc region of the polypeptide.

SUMMARY

The present invention relates to the field of antibody variants and provides polypeptides comprising Fc variants with a decreased effector function, like decreased ADCC and/or C1q binding.

In particular the invention provides a polypeptide comprising an Fc variant of a wild-type human IgG Fc region, said Fc variant comprising an amino acid substitution at position Pro329 and at least one further amino acid substitution, wherein the residues are numbered according to the EU index of Kabat, and wherein said polypeptide exhibits a reduced affinity to the human FcγRIIIA and/or FcγRIIA and/or FcγRI compared to a polypeptide comprising the wildtype IgG Fc region, and wherein the ADCC induced by said polypeptide is reduced to at least 20% of the ADCC induced by the polypeptide comprising a wild-type human IgG Fc region.

In a specific embodiment Pro329 of a wild-type human Fc region in the polypeptide described above is substituted with glycine or arginine or an amino acid residue large enough to destroy the proline sandwich within the Fc/Fcγ receptor interface, that is formed between the proline329 of the Fc and tryptophane residues Trp 87 and Trp 110 of FcgRIII (Sondermann et al. Nature 406, 267-273 (20 Jul. 2000)). In a further aspect of the invention the at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region.

In another aspect of the invention the polypeptide provided exhibits a reduced affinity to at least one further receptor of the group comprising the human receptors FcγI, FcγIIA and C1q compared to the polypeptide comprising a wild-type human IgG Fc region. In still another aspect of the invention the polypeptide comprises a human IgG1 or IgG4 Fc region. In still another aspect of the invention the polypeptide is an antibody or an Fc fusion protein.

In a further embodiment the thrombocyte aggregation induced by the polypeptide comprising the Fc variant is reduced compared to the thrombocyte aggregation induced by a polypeptide comprising a wild-type human IgG Fc region. In still a further embodiment, the polypeptide according to the invention exhibits a strongly reduced CDC compared to the CDC induced by a polypeptide comprising a wild-type human IgG Fc region.

In another embodiment of the invention polypeptides comprising an Fc variant, as described above, are provided for use as a medicament. In a specific embodiment the polypeptide is an anti-CD9 antibody, which is characterized in that the polypeptide comprising the wildtype Fc region comprises as heavy chain variable region SEQ ID NO:9 and as variable light chain region SEQ ID NO:8.

In another aspect of the invention the polypeptides as described above are provided for use in treating a disease wherein it is favorable that an effector function of the polypeptide comprising the Fc variant is strongly reduced compared to the effector function induced by a polypeptide comprising a wild-type human IgG Fc region.

In another embodiment the use of the polypeptides as described above is provided for the manufacture of a medicament for the treatment of a disease, wherein it is favorable that the effector function of the polypeptide comprising an Fc variant of a wild-type human IgG Fc region is strongly reduced compared to the effector function induced by a polypeptide comprising a wild-type human IgG Fc region.

In still another aspect of the invention a method of treating an individual having a disease is provided, wherein it is favorable that the effector function of the polypeptide comprising an Fc variant of a wild-type human IgG Fc region is strongly reduced compared to the effector function induced by a polypeptide comprising a wildtype human Fc polypeptide, comprising administering to an individual an effective amount of the polypeptide described above.

A further aspect of the invention is a use of a polypeptide comprising an Fc variant of a wild-type human IgG Fc region, said polypeptide having Pro329 of the human IgG Fc region substituted with glycine, wherein the residues are numbered according to the EU index of Kabat, wherein said polypeptide exhibits a reduced affinity to the human FcγRIIIA and FcγRIIA for down-modulation of ADCC to at least 20% of the ADCC induced by the polypeptide comprising the wildtype human IgG Fc region, and/or for down-modulation of ADCP.

Another aspect of the invention is use of a polypeptide comprising an Fc variant of a wild-type human IgG Fc region, said polypeptide having Pro329 of the human IgG Fc region substituted with glycine and wherein the Fc variant comprises at least two further amino acid substitutions at L234A and L235A of the human IgG1 Fc region or S228P and L235E of the human IgG4 Fc region, wherein the residues are numbered according to the EU index of Kabat, wherein said polypeptide exhibits a reduced affinity to the human FcγRIIIA and FcγRIIA, for down-modulation of ADCC to at least 20% of the ADCC induced by the polypeptide comprising the wildtype human IgG Fc region, and/or for down-modulation of ADCP.

Another aspect of the invention is use of the polypeptide described above, wherein the thrombocyte aggregation induced by the polypeptide described above is reduced compared to the thrombocyte aggregation induced by a polypeptide comprising a wildtype human Fc region, wherein the polypeptide is a platelet activating antibody.

In another aspect of the invention a method of treating an individual having a disease is provided, wherein said individual is treated with a polypeptide, said polypeptide having Pro329 of the human IgG Fc region substituted with glycine, wherein the residues are numbered according to the EU index of Kabat, wherein said polypeptide is characterized by a strongly reduced binding FcγRIIIA and/or FcγRIIA compared to a polypeptide comprising a wildtype human IgG Fc region, comprising administering to the individual an effective amount of said polypeptide.

In still another aspect of the invention the polypeptide used in said method comprises at least two further amino acid substitutions at L234A and L235A of the human IgG1 Fc region or S228P and L235E of the human IgG4 Fc region.

BACKGROUND

Monoclonal antibodies have great therapeutic potential and play an important role in today's medical portfolio. During the last decade, a significant trend in the pharmaceutical industry has been the development of monoclonal antibodies (mAbs) as therapeutic agents for the treatment of a number of diseases, such as cancers, asthma, arthritis, multiple sclerosis etc. Monoclonal antibodies are predominantly manufactured as recombinant proteins in genetically engineered mammalian cell culture.

The Fc region of an antibody, i.e., the terminal ends of the heavy chains of antibody spanning domains CH2, CH3 and a portion of the hinge region, is limited in variability and is involved in effecting the physiological roles played by the antibody. The effector functions attributable to the Fc region of an antibody vary with the class and subclass of antibody and include binding of the antibody via the Fc region to a specific Fc receptor ("FcR") on a cell which triggers various biological responses.

These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Ravetch, et al., Annu Rev Immunol 19 (2001) 275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). In addition, an overlapping site on the Fc region of the molecule also controls the activation of a cell independent cytotoxic function mediated by complement, otherwise known as complement dependent cytotoxicity (CDC).

For the IgG class of Abs, ADCC and ADCP are governed by engagement of the Fc region with a family of receptors referred to as Fcγ receptors (FcγRs). In humans, this protein family comprises FcγRI (CD64); FcγRII (CD32), including isoforms FcγRIIA, FcγRIIB, and FcγRIIC; and FcγRIII (CD16), including isoforms FcγRIIIA and FcγRIIIB (Raghavan, and Bjorkman, Annu. Rev. Cell Dev. Biol. 12 (1996) 181-220; Abes, et al., Expert Reviews VOL 5(6), (2009) 735-747). FcγRs are expressed on a variety of immune cells, and formation of the Fc/FcγR complex recruits these cells to sites of bound antigen, typically resulting in signaling and subsequent immune responses such as release of inflammation mediators, B cell activation, endocytosis, phagocytosis, and cytotoxic attack. Furthermore, whereas FcγRI, FcγRIIA/c, and FcγRIIIA are activating receptors characterized by an intracellular immunoreceptor tyrosine-based activation motif (ITAM), FcγRIM has an inhibition motif (ITIM) and is therefore inhibitory. Moreover, de Reys, et al., Blood, 81, (1993) 1792-1800 concluded that platelet activation and aggregation induced by monoclonal antibodies, like for example CD9, is initiated by antigen recognition followed by an Fc domain dependent step, which involves the FcγRII-receptor (see also: Taylor, et al., Blood 96 (2000) 4254-4260). While FcγRI binds monomeric IgG with high affinity, FcγRIII and FcγRII are low-affinity receptors, interacting with complexed or aggregated IgG.

The complement inflammatory cascade is a part of the innate immune response and is crucial to the ability for an individual to ward off infection. Another important Fc ligand is the complement protein C1q. Fc binding to C1q mediates a process called complement dependent cytotoxicity (CDC). C1q is capable of binding six antibodies, although binding to two IgGs is sufficient to activate the complement cascade. C1q forms a complex with the C1r and C1s serine proteases to form the C1 complex of the complement pathway.

In many circumstances, the binding and stimulation of effector functions mediated by the Fc region of immunoglobulins is highly beneficial, e.g. for a CD20 antibody, however, in certain instances it may be more advantageous to decrease or even to eliminate the effector function. This is particularly true for those antibodies designed to deliver a drug (e.g., toxins and isotopes) to the target cell where the Fc/FcγR mediated effector functions bring healthy immune cells into the proximity of the deadly payload, resulting in depletion of normal lymphoid tissue along with the target cells (Hutchins, et al., PNAS USA 92 (1995) 11980-11984; White, et al., Annu Rev Med 52 (2001) 125-145). In these cases the use of antibodies that poorly recruit complement or effector cells would be of a tremendous benefit (see also, Wu, et al., Cell Immunol 200 (2000) 16-26; Shields, et al., J. Biol Chem 276(9) (2001) 6591-6604; U.S. Pat. No. 6,194,551; U.S. Pat. No. 5,885,573 and PCT publication WO 04/029207).

In other instances, for example, where blocking the interaction of a widely expressed receptor with its cognate ligand is the objective, it would be advantageous to decrease or eliminate all antibody effector function to reduce unwanted toxicity. Also, in the instance where a therapeutic antibody exhibited promiscuous binding across a number of human tissues it would be prudent to limit the targeting of effector function to a diverse set of tissues to limit toxicity. Last but not least, reduced affinity of antibodies to the FcγRII receptor in particular would be advantageous for antibodies inducing platelet activation and aggregation via FcγRII receptor binding, which would be a serious side-effect of such antibodies.

Although there are certain subclasses of human immunoglobulins that lack specific effector functions, there are no known naturally occurring immunoglobulins that lack all effector functions. An alternate approach would be to engineer or mutate the critical residues in the Fc region that are responsible for effector function. For examples see PCT publications WO 2009/100309 (Medimmune), WO 2006/076594 (Xencor), WO 1999/58572 (Univ. Cambridge), US 2006/0134709 (Macrogenics), WO 2006/047350 (Xencor), WO 2006/053301 (Xencor), U.S. Pat. No. 6,737,056 (Genentech), U.S. Pat. No. 5,624,821 (Scotgen Pharmaceuticals), and US 2010/0166740 (Roche).

The binding of IgG to activating and inhibitory Fcγ receptors or the first component of complement (C1q) depends on residues located in the hinge region and the CH2 domain. Two regions of the CH2 domain are critical for FcγRs and complement C1q binding, and have unique sequences. Substitution of human IgG1 and IgG2 residues at positions 233-236 and IgG4 residues at positions 327, 330 and 331 greatly reduced ADCC and CDC (Armour, et al., Eur. J. Immunol. 29(8) (1999) 2613-2624; Shields, et al., J. Biol. Chem. 276(9) (2001) 6591-6604). Idusogie, et al., J. Immunol. 166 (2000)

2571-2575) mapped the C1q binding site for rituxan and showed that Pro329Ala reduced the ability of Rituximab to bind C1q and activate complement. Substitution of Pro329 with Ala has been reported to lead to a reduced binding to the FcγRI, FcγRII and FcγRIIIA receptors (Shields, et al., J. Biol. Chem. 276(9) (2001) 6591-6604) but this mutation has also been described as exhibiting a wildtype-like binding to the FcγRI and FcγRII and only a very small decrease in binding to the FcγRIIIA receptor (Table 1 and Table 2 in EP 1 068 241, Genentech).

Oganesyan, et al., Acta Cristallographica D64 (2008) 700-704 introduced the triple mutation L234F/L235E/P331S into the lower hinge and C2H domain and showed a decrease in binding activity to human IgG1 molecules to human C1q receptor, FcγRI, FcγRII and FcγRIIIA.

Still, there is an unmet need for antibodies with a strongly decreased ADCC and/or ADCP and/or CDC. Therefore, the aim of the current invention was to identify such antibodies. Surprisingly, it has been found that mutating the proline residue at Pro329 to glycine resulted in an unexpected strong inhibition of the FcγRIIIA and FcγRIIA receptor and in a strong inhibition of ADCC and CDC. Moreover, the combined mutation of Pro329 and for example L234A and L235A (LALA) lead to an unexpected strong inhibition of C1q, FcγRI, FcγRII and FcγRIIIA. Thus, a glycine residue appears to be unexpectedly superior over other amino acid substitutions, like alanine, for example, at position 329 in destroying the proline sandwich in the Fc/Fcγ receptor interface.

Figure 1A:
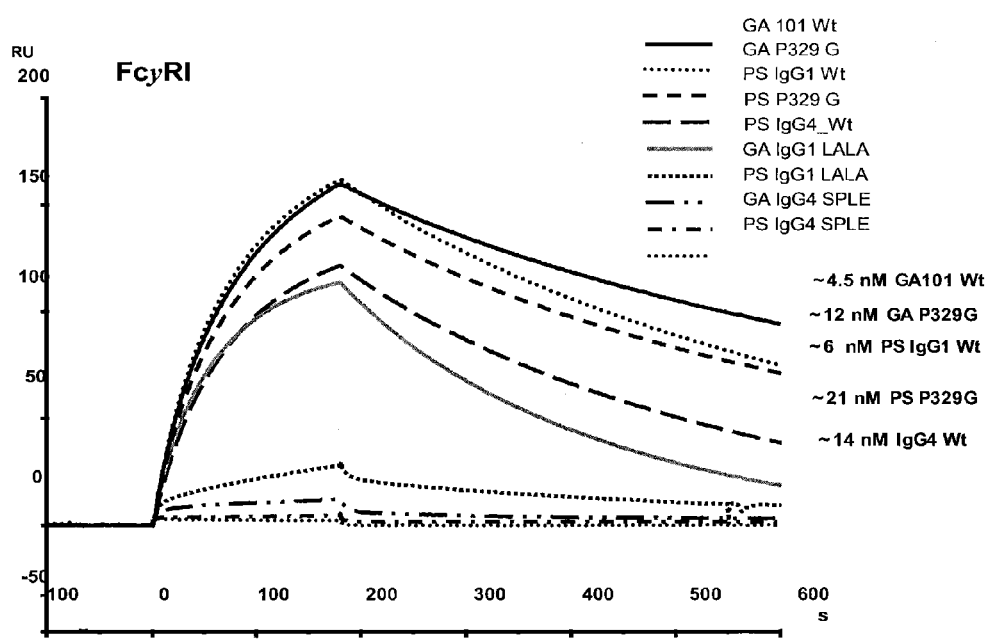
FIG. 1

Binding affinities of different FcγRs towards immunoglobulins were measured by Surface Plasmon Resonance (SPR) using a Biacore T100 instrument (GE Healthcare) at 25° C.
a) FcγRI binding affinity was tested for GA101 (GA) antibody variants (IgG1-P329G, IgG4-SPLE and IgG1-LALA mutation) and for P-selectin (PS) antibody variants (IgG1-P329G, IgG1-LALA and IgG4-SPLE) as well as for the wildtype antibodies.
b) FcγRI binding affinity was tested for CD9 antibody variants (IgG1-wildtype, IgG1-P329G, IgG1-LALA, IgG4-SPLE, IgG1-P329G/LALA, IgG4-SPLE/P329G) as well as for the wildtype antibodies.
c) FcγRIIA(R131) binding affinity was tested for CD9 antibody variants (IgG1-wildtype, IgG1-P329G, IgG1-LALA, IgG4-SPLE, IgG1-P329G/LALA, IgG4-SPLE/P329G) as well as for the wildtype antibodies. A normalized response is shown as a function of the concentration of the receptor.
d) FcγRIIB binding affinity was tested for CD9 (named here: "TA") antibody variants (IgG1-wildtype, IgG4-SPLE/ P329G, IgG1-LALA, IgG1-LALA/P329G) and P-selectin (pSel) antibody variants (IgG4-wildtype, IgG4-SPLE) as well as for the wildtype antibodies.
e) FcγRIIIA-V158 binding affinity was tested for CD9 antibody variants (IgG1-wildtype, IgG4-SPLE, IgG1-LALA, IgG4-SPLE/P329G, IgG1-P329G, IgG1-LALA/P329G) as well as for the wildtype antibodies. a normalized response is shown as a function of the concentration of the receptor.

FIG. 2

C1q binding was tested for P-selectin (PS) antibody variants (IgG1 wildtype, P329G, IgG4-SPLE) and CD20 (GA) antibody variants (IgG1-wildtype, P329G and IgG4-SPLE).

FIG. 3

Potency to recruit immune-effector cells depends on type of Fc variant. Fc variants were coated on an ELISA plate and human NK92 effector cells transfected with human FcγRIIIA were added. Induction of cytolytic activity of activated NK cells was measured using an esterase assay.
a) CD20 (GA101) antibody variants (wildtype, LALA, P329G, P329G/LALA) were analyzed.
b) CD20 (GA101) antibody variants (P329R or P329G mutations introduced) were analyzed. All variants were produced in the glycoengineered version in order to have a stronger signal for any effector cell recruitment function.

FIG. 4

Potency to recruit immune-effector cells depends on type of Fc variant, as measured by classical ADCC assay. Human NK92 cell-line transfected with human FγcRIIIA was used as effector and CD20 positive Raji cells were used as target cells. Different glycengineered CD20 antibody (GA101 G(2) and non-glycoengineered CD20 antibody (GA101) variants (P329G, P329A or LALA mutations introduced) were tested.
a) non-glycoengineered CD20 antibody: P329G, LALA and P329G/LALA mutations, respectively, have been introduced into the antibody, respectively.
b) glycoengineered CD20 antibody: P329G, P329A and LALA mutations, respectively, have been introduced into the antibody, respectively.

FIG. 5

Complement dependent cytotoxicity (CDC) assay. The different Fc variants of a non-glycoengineered and glycoengineered CD20 (GA101) antibody were analyzed for their efficacy to mediate CDC on SUDH-L4 target cells.
a) non-glycoengineered CD20: P329G, LALA and P329G/ LALA mutations, respectively, have been introduced into the antibody, respectively.
b) glycoengineered CD20: P329G, P329A and LALA mutations, respectively, have been introduced into the antibody, respectively.

FIG. 6 a) Carbohydrate profile of Fc-associated glycans of human IgG1 variants. The percentage of galactosylation on Fc-associated oligosacchrides of hIgG1 containing the LALA, P329G, P329A or P329G/LALA mutations only differs minimally from that of wild type antibody.
b) Relative galactosylation: Four different IgGs with introduced IgG1 P329G/LALA mutations. Four different V-domains were compared for their amount of galactosylation when expressed in Hek293 EBNA cells.

FIG. 7

Antibody-induced platelet aggregation in whole blood assay. Murine IgG1 induced platelet aggregation as determined for two donors differing in their response in dependence of the antibody concentration.
a) Donor A, b) Donor B.

DETAILED DESCRIPTION OF THE INVENTION

Definitions

In the present specification and claims, the numbering of the residues in an immunoglobulin heavy chain is that of the EU index as in Kabat, et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

"Affinity" refers to the strength of the sum total of noncovalent interactions between a single binding site of a molecule (e.g., an antibody) and its binding partner (e.g., an antigen or an Fc receptor). Unless indicated otherwise, as used herein, "binding affinity" refers to intrinsic binding affinity which reflects a 1:1 interaction between members of a binding pair (e.g., antibody/Fc receptor or antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "amino acid modification" refers to a change in the amino acid sequence of a predetermined amino acid sequence. Exemplary modifications include an amino acid substitution, insertion and/or deletion. The preferred amino acid modification herein is a substitution. An "amino acid modification at" a specified position, e.g. of the Fc region, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Preferably, the replacement residue is not cysteine. Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman, et al., Meth. Enzym. 202 (1991) 301-336. To generate such non-naturally occurring amino acid residues, the procedures of Noren, et al., Science 244 (1989) 182 and Ellman, et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody variant" as used herein refers to a variant of a wildtype antibody, characterized in that an alteration in the amino acid sequence relative to the wildtype antibody occurs in the antibody variant, e.g. introduced by mutations a specific amino acid residues in the wildtype antibody.

The term "antibody effector function(s)," or "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typical effector functions are ADCC, ADCP and CDC.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, and Kinet, Annu. Rev. Immunol 9 (1991) 457-492.

The term "Antibody-dependent cellular phagocytosis" and "ADCP" refer to a process by which antibody-coated cells are internalized, either in whole or in part, by phagocytic immune cells (e.g., macrophages, neutrophils and dendritic cells) that bind to an immunoglobulin Fc region.

The term "binding domain" refers to the region of a polypeptide that binds to another molecule. In the case of an FcR, the binding domain can comprise a portion of a polypeptide chain thereof (e.g. the a chain thereof) which is responsible for binding an Fc region. One useful binding domain is the extracellular domain of an FcR α chain.

The term "binding" to an Fc receptor used herein means the binding of the antibody to a Fc receptor in a BIAcore® assay for example (Pharmacia Biosensor AB, Uppsala, Sweden).

In the BIAcore® assay the Fc receptor is bound to a surface and binding of the variant, e.g. the antibody variant to which mutations have been introduced, is measured by Surface Plasmon Resonance (SPR). The affinity of the binding is defined by the terms ka (rate constant for the association of the antibody from the antibody/Fc receptor complex), kd (dissociation constant), and KD (kd/ka). Alternatively, the binding signal of a SPR sensogram can be compared directly to the response signal of a reference, with respect to the resonance signal height and the dissociation behaviors.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, Molec. Immunol. 22 (1985) 161-206).

The "CH3 domain" comprises the stretch of residues C-terminal to a CH2 domain in an Fc region (i.e. from about amino acid residue 341 to about amino acid residue 447 of an IgG).

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, the expressions "cell," "cell line," and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "disorder" is any condition that would benefit from treatment with a polypeptide, like antibodies comprising an Fc variant. This includes chronic and acute disorders or diseases including those pathological conditions which predispose the mammal to the disorder in question. In one embodiment, the disorder is cancer.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis (ADCP); down regulation of cell surface receptors (e.g. B cell receptor); and B cell activation.

A "reduced effector function" as used herein refers to a reduction of a specific effector function, like for example ADCC or CDC, in comparison to a control (for example a polypeptide with a wildtype Fc region), by at least 20% and a "strongly reduced effector function" as used herein refers to a reduction of a specific effector function, like for example ADCC or CDC, in comparison to a control, by at least 50%.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Rabat, et al., Sequences of Proteins of Immunological Interest, 5th Ed. Public Health Service, National Institutes of Health, Bethesda, Md. (1991).

A "variant Fc region" comprises an amino acid sequence which differs from that of a "native" or "wildtype" sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "Fc-variant" as used herein refers to a polypeptide comprising a modification in an Fc domain. The Fc variants of the present invention are defined according to the amino acid modifications that compose them. Thus, for example, P329G is an Fc variant with the substitution of proline with glycine at position 329 relative to the parent Fc polypeptide, wherein the numbering is according to the EU index. The identity of the wildtype amino acid may be unspecified, in which case the aforementioned variant is referred to as P329G. For all positions discussed in the present invention, numbering is according to the EU index. The EU index or EU index as in Kabat or EU numbering scheme refers to the numbering of the EU antibody (Edelman, et al., Proc Natl Acad Sci USA 63 (1969) 78-85, hereby entirely incorporated by reference.) The modification can be an addition, deletion, or substitution. Substitutions can include naturally occurring amino acids and non-naturally occurring amino acids. Variants may comprise non-natural amino acids. Examples include U.S. Pat. No. 6,586,207; WO 98/48032; WO 03/073238; US 2004/0214988 A1; WO 05/35727 A2; WO 05/74524 A2; Chin, J. W., et al., Journal of the American Chemical Society 124 (2002) 9026-9027; Chin, J. W., and Schultz, P. G., ChemBioChem 11 (2002) 1135-1137; Chin, J. W., et al., PICAS United States of America 99 (2002) 11020-11024; and, Wang, L., and Schultz, P. G., Chem. (2002) 1-10, all entirely incorporated by reference.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review in Daeron, M., Annu. Rev. Immunol. 15 (1997) 203-234). FcRs are reviewed in Ravetch, and Kinet, Annu. Rev. Immunol 9 (1991) 457-492; Capel, et al., Immunomethods 4 (1994) 25-34; and de Haas, et al., J. Lab. Clin. Med. 126 (1995) 330-41. Other FcRs, including those to be identified in the future, are encompassed by the term "FcR" herein. The term also includes the neonatal receptor, FcRn, which is responsible for the transfer of maternal IgGs to the fetus (Guyer, et al., J. Immunol. 117 (1976) 587 and Kim, et al., J. Immunol. 24 (1994) 249).

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis, et al., Immunological Reviews 190 (2002) 123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIA, FcγRIB, and FcγRIC; FcγRII (CD32), including isoforms FcγRIIA (including allotypes H131 and R131), FcγRIIB (including FcγRIIB-1 and FcγRIIB-2), and FcγRIIc; and FcγRIII (CD16), including isoforms FcγRIIIA (including allotypes V158 and F158) and FcγRIIIb (including allotypes FcγRIIB-NA1 and FcγRIIB-NA2) (Jefferis, et al., Immunol Lett 82 (2002) 57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

By "wildtype or parent polypeptide" as used herein is meant an unmodified polypeptide that is subsequently modified to generate a variant. The wildtype polypeptide may be a naturally occurring polypeptide, or a variant or engineered version of a naturally occurring polypeptide. Wildtype polypeptide may refer to the polypeptide itself, compositions that comprise the parent polypeptide, or the amino acid sequence that encodes it. Accordingly, by "wildtype immunoglobulin" as used herein is meant an unmodified immunoglobulin polypeptide that is modified to generate a variant, and by "wildtype antibody" as used herein is meant an unmodified antibody that is modified to generate a variant antibody. It should be noted that "wildtype antibody" includes known commercial, recombinantly produced antibodies as outlined below.

The term "fragment crystallizable (Fc) polypeptide" is the portion of an antibody molecule that interacts with effector molecules and cells. It comprises the C-terminal portions of the immunoglobulin heavy chains.

The term "Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

"Hinge region" is generally defined as stretching from Glu216 to Pro230 of human IgG1 (Burton, Molec. Immunol. 22 (1985) 161-206). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived there from without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia, and Lesk, J. Mol. Biol. 196 (1987) 901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat, et al., Sequences of Proteins of Immunological Interest, 5th Ed. Public Health Service, National Institutes of Health, Bethesda, Md. (1991)). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (See Almagro, and Fransson, Front. Biosci. 13 (2008) 1619-1633). Unless otherwise indicated, HVR residues and other residues in the variable domain (e.g., FR residues) are numbered herein according to Kabat et al., supra.

"Immune complex" refers to the relatively stable structure which forms when at least one target molecule and at least one heterologous Fc region-containing polypeptide bind to one another forming a larger molecular weight complex. Examples of immune complexes are antigen-antibody aggregates and target molecule-immunoadhesin aggregates. The term "immune complex" as used herein, unless indicated otherwise, refers to an ex vivo complex (i.e. other than the form or setting in which it may be found in nature). However, the immune complex may be administered to a mammal, e.g. to evaluate clearance of the immune complex in the mammal.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, et al., J. Chromatogr. B 848 (2007) 79-87.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant and variable domain.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "package insert" is used to refer to instructions customarily included in commercial packages of therapeutic products, that contain information about the indications, usage, dosage, administration, combination therapy, contraindications and/or warnings concerning the use of such therapeutic products.

By "position" as used herein is meant a location in the sequence of a protein. Positions may be numbered sequentially, or according to an established format, for example the EU index for antibody numbering.

The terms "polypeptide" and "protein" are used interchangeably to refer to a polymer of amino acid residues, comprising natural or non-natural amino acid residues, and are not limited to a minimum length.

Thus, peptides, oligopeptides, dimers, multimers, and the like are included within the definition. Both full-length proteins and fragments thereof are encompassed by the definition. The terms also include post-translational modifications of the polypeptide, including, for example, glycosylation, sialylation, acetylation, and phosphorylation.

Furthermore, a "polypeptide" herein also refers to a modified protein such as single or multiple amino acid residue deletions, additions, and substitutions to the native sequence, as long as the protein maintains a desired activity. For example, a serine residue may be substituted to eliminate a single reactive cysteine or to remove disulfide bonding or a conservative amino acid substitution may be made to eliminate a cleavage site. These modifications may be deliberate, as through site-directed mutagenesis, or may be accidental, such as through mutations of hosts which produce the proteins or errors due to polymerase chain reaction (PCR) amplification.

The term "wildtype polypeptide" and "wildtype (human) Fc region" as used herein refers to a polypeptide and Fc region, respectively, comprising an amino acid sequence which lacks one or more of the Fc region modifications disclosed herein, because they have not been introduced, and serve for example as controls. The wildtype polypeptide may comprise a native sequence Fc region or an Fc region with pre-existing amino acid sequence modifications (such as additions, deletions and/or substitutions).

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A polypeptide with "altered" FcR binding affinity or ADCC activity is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The polypeptide variant which "displays decreased binding" to an FcR, binds at least one FcR with worse affinity than a parent polypeptide. Such variants which display decreased binding to an FcR may possess little or no appreciable binding to an FcR, e.g., 0-20% binding to the FcR compared to a native sequence IgG Fc region, e.g. as determined in the Examples herein.

The polypeptide which binds an FcR with "reduced affinity" than a parent polypeptide, is one which binds any one or more of the above identified FcRs with substantially reduced binding affinity than the parent antibody, when the amounts of polypeptide variant and parent polypeptide in the binding assay are essentially the same. For example, the polypeptide variant with reduced FcR binding affinity may display from about 1.15 fold to about 100 fold, e.g. from about 1.2 fold to about 50 fold reduction in FcR binding affinity compared to the parent polypeptide, where FcR binding affinity is determined, for example, as disclosed in the Examples herein.

The polypeptide comprising an Fc variant which "mediates antibody-dependent cell-mediated cytotoxicity (ADCC) in the presence of human effector cells less effectively" than a parent or wildtype polypeptide is one which in vitro or in vivo is substantially less effective at mediating ADCC, when the amounts of polypeptide variant and parent antibody used in the assay are essentially the same. Generally, such variants will be identified using the in vitro ADCC assay as herein disclosed, but other assays or methods for determining ADCC activity, e.g. in an animal model etc, are contemplated. The preferred variant is from about 1.5 fold to about 100 fold, e.g. from about two fold to about fifty fold, less effective at mediating ADCC than the parent, e.g. in the in vitro assay disclosed herein.

A "receptor" is a polypeptide capable of binding at least one ligand. The preferred receptor is a cell-surface receptor having an extracellular ligand-binding domain and, optionally, other domains (e.g. transmembrane domain, intracellular domain and/or membrane anchor). The receptor to be evaluated in the assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. The protein variant sequence herein will preferably possess at least about 80% homology with a parent protein sequence, and most preferably at least about 90% homology, more preferably at least about 95% homology. Variant protein can refer to the variant protein itself, compositions comprising the protein variant, or the DNA sequence that encodes it. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs)

and three hypervariable regions (HVRs). (See, e.g., Kindt, et al., Kuby Immunology, 6th ed., W.H. Freeman and Co. (2007) page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, et al., J. Immunol. 150 (1993) 880-887; Clackson, et al., Nature 352 (1991) 624-628.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The present application is directed to polypeptides that include amino acid modifications that modulate binding to Fc receptors, in particularly to Fcγ receptors.

DETAILED DESCRIPTION

The invention herein relates to a method for making a polypeptide comprising a Fc variant. The "parent", "starting", "nonvariant" or wildtype polypeptide is prepared using techniques available in the art for generating polypeptides or antibodies comprising an Fc region. In the preferred embodiment of the invention, the parent polypeptide is an antibody and exemplary methods for generating antibodies are described in more detail in the following sections. The parent polypeptide may, however, be any other polypeptide comprising an Fc region, e.g. an immunoadhesin. Methods for making immunoadhesins are elaborated in more detail herein below.

In an alternative embodiment, a variant Fc region (Fc variant) may be generated according to the methods herein disclosed and this Fc variant can be fused to a heterologous polypeptide of choice, such as an antibody variable domain or binding domain of a receptor or ligand.

The wildtype polypeptide comprises an Fc region. Generally the Fc region of the wildtype polypeptide will comprise a native or wildtype sequence Fc region, and preferably a human native sequence Fc region (human Fc region). However, the Fc region of the wildtype polypeptide may have one or more pre-existing amino acid sequence alterations or modifications from a native sequence Fc region. For example, the C1q or Fcγ binding activity of the Fc region may have been previously altered (other types of Fc region modifications are described in more detail below). In a further embodiment the parent polypeptide Fc region is "conceptual" and, while it does not physically exist, the antibody engineer may decide upon a desired variant Fc region amino acid sequence and generate a polypeptide comprising that sequence or a DNA encoding the desired variant Fc region amino acid sequence.

In the preferred embodiment of the invention, however, a nucleic acid encoding an Fc region of a wildtype polypeptide is available and this nucleic acid sequence is altered to generate a variant nucleic acid sequence encoding the Fc region variant.

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide Site-directed mutagenesis is a preferred method for preparing substitution variants. This technique is well known in the art (see, e.g., Carter, et al., Nucleic Acids Res. 13 (1985) 4431-4443 and Kunkel, et al., Proc. Natl. Acad. Sci. USA 82 (1985) 488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide. See Higuchi, in PCR Protocols, Academic Press (1990) pp. 177-183; and Vallette, et al., Nuc. Acids Res. 17 (1989) 723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells, et al., Gene 34 (1985) 315-323.

One embodiment of the invention encompasses polypeptides comprising an Fc region of an antibody, comprising the addition, substitution, or deletion of at least one amino acid residue to the Fc region resulting in reduced or ablated affinity for at least one Fc receptor. The Fc region interacts with a number of receptors or ligands including but not limited to Fc Receptors (e.g., FcγRI, FcγRIIA, FcγRIIIA), the complement protein C1q, and other molecules such as proteins A and G. These interactions are essential for a variety of effector functions and downstream signaling events including, but not limited to, antibody dependent cell-mediated cytotoxicity (ADCC), Antibody-dependent cellular phagocytosis (ADCP) and complement dependent cytotoxicity (CDC). Accordingly, in certain embodiments the variants of the invention have reduced or ablated affinity for an Fc receptor responsible for an effector function compared to a polypeptide having the same amino acid sequence as the polypeptide comprising a Fc variant of the invention but not comprising the addition, substitution, or deletion of at least one amino acid residue to the Fc region (also referred to herein as an "wildtype polypeptide"). In certain embodiments, polypeptide comprising a Fc variant of the invention comprise at least one or more of the following properties: reduced or ablated effector (ADCC and/or CDC and/or ADCP) function, reduced or ablated binding to Fc receptors, reduced or ablated binding to C1q or reduced or ablated toxicities. More specifically, embodiments of the invention provide anti-CD20 (same as GA101 or GA), anti-CD9 (same as TA) and anti-Selectin (pSel) antibodies with reduced affinity for Fc receptors (e.g. FcγRI, FcγRII, FcγRIIIA) and/or the complement protein C1q.

In one embodiment, antibodies of the invention comprise an Fc region comprising at least one addition, substitution, or deletion of an amino acid residue at position P329, wherein the numbering system of the constant region is that of the EU index as set forth in Kabat, et al., NIH Publication 91 (1991) 3242, National Technical Information Service, Springfield, Va.

In a specific embodiment, polypeptides of the invention comprise an Fc variant of a wild-type human Fc polypeptide said variant comprising an amino acid substitution at position Pro329, where the numbering of the residues in the IgG Fc region is that of the EU index as in Kabat. In still another embodiment, said variant comprises at least one further amino acid substitution.

In still another embodiment the polypeptide comprising a Fc variant of a wild-type human Fc polypeptide has an amino acid substitution, deletion or addition which destroys or diminishes the function of the proline sandwich in the region and/or interface of the Fc polypeptide with the Fc Gamma receptor.

In another embodiment Pro329 is substituted with an amino acid which is either smaller or larger then proline. In still another embodiment the substituted amino acid is Gly, Ala or Arg. In a further aspect of the invention Pro329 of the Fc polypeptide is substituted with glycine.

In still another embodiment said polypeptide comprising a Fc variant has at least one further amino acid substitution, addition of deletion. In still another embodiment, said variants exhibit a reduced affinity to a human Fc receptor (FcγR) and/or a human complement receptor as compared to the polypeptide comprising the wildtype Fc polypeptide.

In another embodiment said polypeptide comprising a Fc variant exhibits a reduced affinity to a human Fc receptor (FcγR) and/or a human complement receptor as compared to the polypeptide comprising the wildtype human Fc region. In a further embodiment the affinity to at least one of the FcγRI, FcγRII, FcγRIIIA is reduced, in a still further embodiment the affinity to the FcγRI and FcγRIIIA is reduced, and in a still further embodiment the affinity to the FcγRI, FcγRII and FcγRIIIA is reduced, in still a further aspect of the invention the affinity to the FcγRI receptor, FcγRIIIA receptor and C1q is reduced, and in still a further aspect of the invention the affinity to the FcγRI, FcγRII, FcγRIIIA and C1q receptor is reduced.

In still a further embodiment the ADCC induced by said polypeptide comprising a Fc variant is reduced and in a preferred embodiment the ADCC is reduced to at least 20% of the ADCC induced by the polypeptide comprising the wildtype Fc polypeptide. In still a further aspect of the invention, the ADCC and CDC induced by the polypeptide comprising the wildtype Fc polypeptide is decreased or ablated and in a still further aspect the polypeptide comprising a Fc variant described above exhibit a decreased ADCC, CDC and ADCP compared to the polypeptide comprising the wildtype Fc polypeptide.

In one embodiment the at least one further amino acid substitution in the polypeptide comprising the Fc variant is selected from the group: S228P, E233P, L234A, L235A, L235E, N297A, N297D, or P331S.

In a certain aspect of the invention the polypeptide comprising a Fc variant comprises an antibody. In still another aspect of the invention the polypeptide comprising a Fc variant comprises a human IgG1 or IgG4 Fc region. In still a further aspect of the invention the variants are IgG1 or IgG4 antibodies.

In another embodiment of the invention, polypeptides comprising a Pro329 Fc variant variants further comprise at least one addition, substitution, or deletion of an amino acid residue in the Fc region that is correlated with increased stability of the antibody. In still a further aspect of the invention the affinity of the polypeptide comprising a Fc variant described above to the Fcn receptor is only slightly, and for example not more than 10-20% of the affinity of polypeptide comprising the wildtype Fc polypeptide altered.

In one embodiment, the addition, substitution, or deletion of an amino acid residue in a polypeptide comprising a Fc variant is at position 228 and/or 235 of the Fc region, wherein the numbering system of the constant region is that of the EU index as set forth in Kabat, et al.

In a specific embodiment serine at position 228 and/or leucine at position 235 in said polypeptide comprising a Fc variant is substituted by another amino acid.

In a specific embodiment, polypeptides comprising a Fc variant of the invention comprise an Fc region comprising an amino acid substitution at position 228, wherein the serine residue is substituted with proline.

In a specific embodiment, polypeptides comprising a Fc variant of the invention comprise an Fc region comprising an amino acid substitution at position 235, wherein the leucine residue is substituted with glutamic acid.

In a specific embodiment the polypeptide comprising a Fc variant comprises a triple mutation: an amino acid substitution at position P329, a S228P and a L235E mutation (P329/SPLE).

In a further specific embodiment the polypeptide comprising a Fc variant comprises a human IgG4 region.

In one embodiment, the addition, substitution, or deletion of an amino acid residue is at position 234 and/or 235 of the Fc region, wherein the numbering system of the constant region is that of the EU index as set forth in Kabat et al.

In a specific embodiment leucine at position 234 and/or leucine at position 235 in the polypeptide comprising a Fc variant is substituted by another amino acid.

In a specific embodiment, polypeptides comprising a Fc variant of the invention comprise an Fc region comprising an amino acid substitution at position 234, wherein the leucine residue is substituted with alanine.

In a specific embodiment, polypeptides comprising a Fc variant of the invention comprise an Fc region comprising an amino acid substitution at position 235, wherein the leucine residue is substituted with serine.

In a specific embodiment the polypeptide comprising an Fc variant of a wildtype human Fc polypeptide comprises a triple mutation: an amino acid substitution at position Pro329, a L234A and a L235A mutation (P329/LALA).

In a further specific embodiment the above mentioned polypeptides comprise a human IgG1 region.

While it is preferred to alter binding to a FcγR, Fc region variants with altered binding affinity for the neonatal receptor (FcRn) are also contemplated herein. Fc region variants with improved affinity for FcRn are anticipated to have longer serum half-lives, and such molecules will have useful applications in methods of treating mammals where long half-life of the administered polypeptide is desired, e.g., to treat a chronic disease or disorder. Fc region variants with decreased FcRn binding affinity, on the contrary, are expected to have shorter half-lives, and such molecules may, for example, be administered to a mammal where a shortened circulation time may be advantageous, e.g. for in vivo diagnostic imaging or for polypeptides which have toxic side effects when left circulating in the blood stream for extended periods, etc. Fc region variants with decreased FcRn binding affinity are anticipated to be less likely to cross the placenta, and thus may be utilized in the treatment of diseases or disorders in pregnant women.

Fc region variants with altered binding affinity for FcRn include those comprising an Fc region amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447. Those which display reduced binding to FcRn will generally comprise an Fc region amino acid modification at any one or more of amino acid positions 252, 253, 254, 255, 288, 309, 386, 388, 400, 415, 433, 435, 436, 439 or 447; and those with increased binding to FcRn will usually comprise an Fc region amino acid modification at any one or more of amino acid positions 238, 256, 265, 272, 286, 303, 305, 307, 311, 312, 317, 340, 356, 360, 362, 376, 378, 380, 382, 413, 424 or 434.

In another embodiment, antibodies of the invention may be any of any class (for example, but not limited to IgG, IgM, and IgE). In certain embodiments, antibodies of the invention are members of the IgG class of antibodies. In a specific embodiment, antibodies of the invention are of the IgG1, IgG2 or IgG4 subclass. In another specific embodiment, antibodies of the invention are of the IgG1 subclass and comprise the following amino acid substitutions: P329G and/or L234A and L235A of the Fc region. In alternate embodiments, antibodies of the invention are of the IgG4 subclass. In a specific embodiment, antibodies of the invention are of the IgG4 subclass and comprise the following amino acid substitutions: P329G and/or S228P and L235E of the Fc region. In certain embodiments, the modified antibodies of the present invention may be produced by combining a variable domain, or fragment thereof, with an Fc domain comprising one or more of the amino acid substitutions disclosed herein. In other embodiments modified antibodies of the invention may be produced by modifying an Fc domain-containing antibody by introducing one or more of the amino acid substitutions residues into the Fc domain.

Reduced Binding to Fc Ligands

One skilled in the art will understand that antibodies of the invention may have altered (relative to an unmodified antibody) FcγR and/or C1q binding properties (examples of binding properties include but are not limited to, binding specificity, equilibrium dissociation constant ($K_D$), dissociation and association rates ($k_{off}$ and $k_{on}$, respectively) binding affinity and/or avidity) and that certain alterations are more or less desirable. It is known in the art that the equilibrium dissociation constant ($K_D$) is defined as $k_{off}/k_{on}$. One skilled in the art can determine which kinetic parameter is most important for a given antibody application. For example, a modification that reduces binding to one or more positive regulator (e.g., FcγRIIIA) and/or enhanced binding to an inhibitory Fc receptor (e.g., FcγRIIB) would be suitable for reducing ADCC activity. Accordingly, the ratio of binding affinities (e.g., equilibrium dissociation constants ($K_D$)) can indicate if the ADCC activity of an antibody of the invention is enhanced or decreased. Additionally, a modification that reduces binding to C1q would be suitable for reducing or eliminating CDC activity. The affinities and binding properties of an Fc region for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immuno absorbent assay (ELISA) or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4$^{th}$ Ed., Lippincott-Raven, Philadelphia (1999).

In one aspect of the invention a polypeptide comprising an Fc variant of a wild-type human Fc region, said variant comprising an amino acid substitution at position Pro329 and at least one further amino acid substitution, exhibits a reduced affinity to a human Fc receptor (FcγR) and/or a human complement receptor as compared to the polypeptide comprising the wildtype Fc polypeptide. In one aspect polypeptides comprising an Fc variant of the invention exhibit affinities for a Fc receptor that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than for a wildtype Fc polypeptide.

In one aspect polypeptides comprising an Fc variant of the invention exhibit reduced binding affinity for one or more Fc receptors including, but not limited to FcγRI (CD64) including isoforms FcγRIA, FcγRII and FcγRIII (CD 16, including isoforms FcγRIIIA) as compared to an unmodified antibody.

In one aspect polypeptides comprising an Fc variant of the invention exhibit reduced binding affinity for FcγRI (CD64) FcγRIIA and FcγRIIIA as compared to an unmodified antibody.

In one aspect polypeptides comprising an Fc variant of the invention exhibit reduced binding affinity for FcγRIIA and FcγRIIIA as compared to an unmodified antibody.

In one aspect polypeptides comprising an Fc variant of the invention exhibit reduced binding affinity for FcγRI (CD64) and FcγRIIIA as compared to an unmodified antibody.

In one aspect of the invention polypeptides comprising an Fc variant of the invention exhibiting a reduced binding affinity for the Fc receptors also exhibit a reduced affinity to the C1q receptor.

In certain aspect polypeptides comprising an Fc variant of the invention do not comprise a concomitant increase in binding to the FcγRIIB receptor as compared to a wildtype polypeptide. In certain aspects of the invention the polypeptides comprising an Fc variant have a reduced affinity to the human receptor FcγIIIA, and to at least one further receptor of the group comprising the human receptors FcγIIA, FcγIIIB, and C1q compared to the polypeptide comprising the wildtype Fc polypeptide. In further aspects of the invention polypeptides comprising an Fc variant have a reduced affinity to the human receptor FcγIIIA, and to at two further receptors of the group comprising the human receptors FcγIIA, FcγIIIB, and C1q compared to the polypeptide comprising the wildtype Fc polypeptide. In further aspect of the invention the polypeptides comprising an Fc variant have a reduced affinity to the human FcγRIA, FcγIIIA, FcγIIA, FcγIIIB, and C1q compared to the polypeptide comprising the wildtype Fc polypeptide. In still another aspect of the invention polypeptides comprising an Fc variant have a reduced affinity to the human receptor FcγRIA, FcγIIIA, FcγIIA, FcγIIIB, and C1q compared to the polypeptide comprising the wildtype Fc polypeptide.

In one aspect of the invention polypeptides comprising an Fc variant of the invention exhibit decreased affinities to FcγRI or FcγRIIA relative to an unmodified antibody. In one aspect of the invention polypeptides comprising an Fc variant exhibit affinities for FcγRI or FcγRIA that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a wildtype polypeptide. In one aspect of the invention polypeptides comprising an Fc variant exhibit affinity for the FcγRI or FcγRIIA that are at least 90%, at least 80%, at least 70%, at least 60%, at least 50%, at least 40%, at least 30%, at least 20%, at least 10%, or at least 5% less than a than that of a wildtype polypeptide.

In one aspect of the invention polypeptides comprising an Fc variant of the invention exhibit decreased affinity for the FcγRIIIA relative to an unmodified antibody. In one aspect polypeptides comprising an Fc variant of the invention exhibit affinities for FcγRIIIA that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a wildtype polypeptide.

In one aspect of the invention polypeptides comprising an Fc variant of the invention exhibit affinities for FcγRIIIA that are at least 90%, at least 80%, at least 70%, at least 60%, at least 50%, at least 40%, at least 30%, at least 20%, at least 10%, or at least 5% less than that of a wildtype polypeptide.

It is understood in the art that the F1-58V allelic variant of the FcγRIIIA has altered binding characteristics to antibodies. In one embodiment, polypeptides comprising an Fc variant of the invention bind with decreased affinities to FcγRIIIA receptors relative to a wildtype polypeptide. In one aspect polypeptides comprising an Fc variant of the invention exhibit affinities for FcγRIIIA (Fl 58V) that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a wildtype polypeptide.

In one aspect of the invention polypeptides comprising an Fc variant of the invention exhibit decreased affinity for the C1q receptor relative to an unmodified antibody. In one aspect polypeptides comprising an Fc variant of the invention exhibit affinities for C1q receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a wildtype polypeptide.

In one aspect of the invention polypeptides comprising an Fc variant of the invention exhibit affinities for C1q that are at least 90%, at least 80%, at least 70%, at least 60%, at least 50%, at least 40%, at least 30%, at least 20%, at least 10%, or at least 5% less than that of a wildtype polypeptide.

In one aspect of the invention polypeptides comprising an Fc variant of the invention exhibit affinities for the human FcγRI, FcγRIIA, FcγRIIIA, FcγRIIIA (Fl 58V) or C1q receptors that are at least 90%, at least 80%, at least 70%, at least 60%, at least 50%, at least 40%, at least 30%, at least 20%, at least 10%, or at least 5% less than a wildtype polypeptide.

In another aspect of the invention polypeptides comprising an Fc variant of the invention exhibit affinities for the FcγRI, FcγRIIA, FcγRIIIA, FcγRIIIA (Fl 58V) and/or C1q receptors, respectively, that are between about 10 nM to 100 nM, 10 nM to 1 µM, 100 nM to about 100 µM, or about 100 nM to about 10 µM, or about 100 nM to about 1 µM, or about 1 nM to about 100 µM, or about 10 nM to about 100 µM, or about 1 µM to about 100 µM, or about 10 µM to about 100 µM. In certain embodiments, polypeptides comprising an Fc variant of the invention exhibit affinities for the FcγRI, FcγRIIA, FcγRIIIA, FcγRIIIA (Fl-58V) or C1q receptors that are greater than 100 nM, 500 nM, 1 µM, greater than 5 µM, greater than 10 µM, greater than 25 µM, greater than 50 µM, or greater than 100 µM.

In another aspect of the invention polypeptides comprising an Fc variant of the invention exhibit increased affinities for the FcγRIIB as compared to a wildtype polypeptide. In another aspect of polypeptides comprising an Fc variant of the invention exhibit affinities for the FcγRIIB that are unchanged or increased by at least at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold than that of an unmodified antibody. In another aspect polypeptides comprising an Fc variant of the invention exhibit affinities for the FcγRIIB receptor that are increased by at least 5%, at least 10%, at least 20%, at least 30%, at least 40%, at least 50%, at least 60%, at least 70%, at least 80%, at least 90%, or at least 95% than a wildtype polypeptide.

In another aspect of the invention variants of the invention exhibit affinities for the FcγRI, FcγRIIA FcγRIIIA, or FcγRIIIA (Fl 58V) or C1q receptors that are less than 100 µM, less than 50 µM, less than 10 µM, less than 5 µM, less than 2.5 µM, less than 1 µM, or less than 100 nM, or less than 10 nM.

Reduced Effector Function

In a certain aspects of the invention polypeptides comprising an Fc variant according to the invention modulate an effector function as compared to the polypeptide comprising the wildtype Fc polypeptide.

In still another aspect of the invention this modulation is a modulation of ADCC and/or ADCP and/or CDC. In a further aspect of the invention this modulation is down-modulation or reduction in effect. In still another aspect of the invention this is a modulation of ADCC and still in another aspect of the invention this modulation is a down-modulation of ADCC. In still another aspect this modulation is a down-modulation of ADCC and CDC, still in another embodiment this is a down-modulation is ADCC only, in still another embodiment this is a down-modulation of ADCC and CDC and/or ADCP. In still another aspect of the invention the polypeptides comprising an Fc variant according to the invention down-modulate or reduce ADCC/CDC and ADCP.

In a further aspect of the invention the reduction or down-modulation of ADCC or CDC or ADCP induced by the polypeptide comprising the Fc variant, is a reduction to 0, 2.5, 5, 10, 20, 50 or 75% of the value observed for induction of ADCC, or CDC or ADCP, respectively, by the polypeptide comprising the wildtype Fc region.

In still further aspects of the invention the modulation of ADCC induced by the polypeptides comprising an Fc variant according to the invention is a decrease in potency such that the EC50 of said Fc variant is approximately >10-fold reduced compared to the polypeptide comprising the wildtype Fc polypeptide.

In still another aspect the variant according to the invention is devoid of any substantial ADCC and/or CDC and/or ADCP in the presence of human effector cells as compared to the polypeptide comprising the wildtype Fc polypeptide.

In still another aspect of the invention the polypeptides comprising an Fc variant of the invention exhibit a reduced, for example reduction by at least 20%, or strongly reduced, for example reduction by at least 50%, effector function, which could be a reduction in ADCC (down-modulation), CDC and/or ADCP.

Reduced ADCC Activity

In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, RII and RIII. FcR expression on hematopoietic cells is summarized in Table 3 on page 464 of Ravetch, and Kinet, Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I., et al., Proc. Nat'l Acad. Sci. USA 83 (1986) 7059-7063) and Hellstrom, I., et al., Proc. Nat'l Acad. Sci. USA 82 (1985) 1499-1502; U.S. Pat. No. 5,821,337 (see Bruggemann, M., et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes, et al., Proc. Nat'l Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, et al., J. Immunol. Methods 202 (1996) 163; Cragg, M. S., et al., Blood 101 (2003) 1045-1052; and Cragg, M. S., and Glennie, M. J., Blood 103 (2004) 2738-2743). FcRn binding and in vivo clearance/half life determinations can also be performed using methods known in the art (see, e.g., Petkova, S. B., et al., Int'l. Immunol. 18(12) (2006) 1759-1769).

It is contemplated that polypeptides comprising a Fc variant of the invention are characterized by in vitro functional assays for determining one or more FcγR mediated effector cell functions. In certain embodiments, antibodies of the invention have similar binding properties and effector cell functions in in vivo models (such as those described and disclosed herein) as those in in vitro based assays. However, the present invention does not exclude variants of the invention that do not exhibit the desired phenotype in in vitro based assays but do exhibit the desired phenotype in vivo. In one embodiment, polypeptides comprising a Fc variant of the invention exhibit decreased ADCC activities as compared to an unmodified wildtype Fc polypeptides. In another aspect polypeptides comprising an Fc variant of the invention exhibit ADCC activities that are at least 2 fold, or at least 3 fold, or at least 5 fold or at least 10 fold or at least 50 fold or at least 100 fold less than that of an unmodified antibody. In still another embodiment, antibodies of the invention exhibit ADCC activities that are reduced by at least 10%, or at least 20%, or by at least 30%, or by at least 40%, or by at least 50%, or by at least 60%, or by at least 70%, or by at least 80%, or by at least 90%, or by at least 100%, relative to an unmodified antibody. In a further aspect of the invention the reduction or down-modulation of ADCC induced by the polypeptide comprising the Fc variant, is a reduction to 0, 2.5, 5, 10, 20, 50 or 75% of the value observed for induction of ADCC, or CDC or ADCP, respectively, by the polypeptide comprising the wildtype Fc region. In certain embodiments, polypeptides comprising an Fc variant of the invention have no detectable ADCC activity. In specific embodiments, the reduction and/or ablation of ADCC activity may be attributed to the reduced affinity of the polypeptides comprising a Fc variant of the invention for Fc ligands and/or receptors. In a specific embodiment of the invention the down-modulation of ADCC is a decrease in potency such that the EC50 of said polypeptide comprising an Fc variant is approximately 10-fold or more reduced compared to the wildtype Fc polypeptide.

In still another aspect the polypeptides comprising an Fc variant according to the invention modulate ADCC and/or CDC and/or ADCP. In a specific aspect the variants according to the inventions show a reduced CDC and ADCC and/or ADCP activity.

Reduced CDC Activity

The complement activation pathway is initiated by the binding of the first component of the complement system (C1q) to a molecule, an antibody for example, complexed with a cognate antigen. To assess complement activation, a CDC assay, e.g. as described in Gazzano-Santoro, et al, J. Immunol. Methods 202 (1996) 163, may be performed.

The binding properties of the different variants to C1q can be analyzed by an ELISA sandwich type immunoassay. The antibody concentration at the half maximum response determines the $EC_{50}$ value. This read-out is reported as relative difference to the reference standard measured on the same plate together with the coefficient of variation of sample and reference.

In one embodiment, polypeptides comprising an Fc variant according to the invention exhibit decreased affinities to C1q relative to a wildtype polypeptide. In another embodiment, of the polypeptides comprising a Fc variant according to the invention exhibit affinities for C1q receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than the wildtype polypeptide.

In another embodiment, polypeptides comprising a Fc variant according to the invention exhibit affinities for C1q that are at least 90%, at least 80%, at least 70%, at least 60%, at least 50%, at least 40%, at least 30%, at least 20%, at least 10%, or at least 5% less than that of the wildtype polypeptide. In another embodiment, variants according to the invention exhibit affinities for C1q that are between about 100 nM to about 100 µM, or about 100 nM to about 10 µM, or about 100 nM to about 1 µM, or about 1 nM to about 100 µM, or about 10 nM to about 100 µM, or about 1 µM to about 100 µM, or about 10 µM to about 100 µM. In certain embodiments, polypeptides comprising an Fc variant of the invention exhibit affinities for CIq that are greater than 1 µM, greater than 5 µM, greater than 10 µM, greater than 25 µM, greater than 50 µM, or greater than 100 µM.

In one embodiment polypeptide comprising an Fc variant of the invention exhibit decreased CDC activities as compared to the wildtype Fc polypeptide In another embodiment, polypeptide comprising an Fc variant of the invention exhibit CDC activities that are at least 2 fold, or at least 3 fold, or at least 5 fold or at least 10 fold or at least 50 fold or at least 100 fold less than that of a wildtype polypeptide. In still another embodiment polypeptide comprising an Fc variant of the invention exhibit CDC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the wildtype polypeptide. In certain aspects polypeptide comprising an Fc variant of the invention exhibit no detectable CDC activities. In specific embodiments, the reduction and/or ablation of CDC activity may be attributed to the reduced affinity of the polypeptides comprising an Fc variant for Fc ligands and/or receptors.

Reduced Antibody Related Toxicity

It is understood in the art that biological therapies may have adverse toxicity issues associated with the complex nature of directing the immune system to recognize and attack unwanted cells and/or targets. When the recognition and/or the targeting for attack do not take place where the treatment is required, consequences such as adverse toxicity may occur. For example, antibody staining of non-targeted tissues may be indicative of potential toxicity issues.

In one aspect, polypeptide comprising an Fc variant of the invention exhibit reduced staining of non-targeted tissues as compared to the wildtype polypeptide. In another aspect, the polypeptide comprising an Fc variant of the invention exhibit reduced staining of non-targeted tissues that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of to a wildtype Fc polypeptide. In another embodiment, variants of the invention exhibit reduced staining of non-targeted tissues that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the wildtype Fc polypeptide.

In one embodiment, polypeptides comprising an Fc variant of the invention exhibit a reduced antibody related toxicity as compared to a wildtype polypeptide. In another embodiment, polypeptide comprising an Fc variant of the invention exhibit toxicities that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a wildtype polypeptide. In another aspect, polypeptides comprising an Fc variant of the invention exhibit toxicities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the wildtype polypeptide.

Thrombocyte Aggregation

In one aspect of the invention the wildtype polypeptide induces platelet activation and/or platelet aggregation, and the variants thereof, i.e. polypeptides, comprising Fc variants, show a decreased or even ablated thrombocyte activation and/or aggregation. In still another aspect of the invention these wildtype polypeptides are antibodies targeting a platelet protein. In yet another aspect the antibody is a CD9 antibody. In still another embodiment this CD9 antibody has a mutation at position P329G and/or at position L234A/L235A or S228P/L235E (P329G/LALA, P329G/SPLE). In a further specific embodiment the antibody is characterized by the SEQ ID NOs: 8-14.

It is understood in the art that biological therapies may have as adverse effect thrombocyte aggregation. In vitro and in vivo assays could be used for measuring thrombocyte aggregation. It is assumed that the in vitro assay reflects the in vivo situation.

In one aspect, polypeptides comprising an Fc variant of the invention exhibit reduced thrombocyte aggregation in an in vitro assay compared to the wildtype polypeptide. In another aspect, polypeptides comprising an Fc variant of the invention exhibit reduced thrombocyte aggregation in an in vitro assay that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of the wildtype polypeptide. In another embodiment, polypeptides comprising an Fc variant of the invention exhibit reduced thrombocyte aggregation in an in vitro assay that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the wildtype polypeptide.

In still another aspect, polypeptides comprising an Fc variant of the inventions exhibit a reduced in vivo thrombocyte aggregation compared to the wildtype polypeptide. In another aspect, variants of the invention exhibit reduced thrombocyte aggregation in an in vivo assay that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of the wildtype Fc polypeptide. In another embodiment, polypeptides comprising an Fc variant of the invention exhibit reduced thrombocyte aggregation in an in vivo assay that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the wildtype polypeptide.

Internalizing Antibodies

Variants of the invention may bind to cell-surface antigens that may internalize, further carrying the antibodies into the cell. Once inside the cell, the variants may be released into the cytoplasm, targeted to a specific compartment, or recycled to the cell surface. In some embodiments, the variants of the invention bind to a cell-surface antigen that internalizes. In other embodiments, antibodies of the invention may be targeted to specific organelles or compartments of the cell. In yet other embodiments, the variants of the invention may be recycled to the cell surface or periphery after internalization.

In a specific embodiment, the antibody of the invention is specific for p-Selectin, CD9, CD19, CD81, CCR5 or CXCR5, IL17a or Il-33.

Antibody Preparation

In the preferred embodiment of the invention, the Fc region-containing polypeptide which is modified according to the teachings herein is an antibody. Techniques for producing antibodies follow:

Antigen Selection and Preparation

Where the polypeptide is an antibody, it is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred molecular targets for antibodies encompassed by the present invention include CD proteins such as CD4, CD8, CD19, CD20 and CD34; members of the ErbB receptor family such as the EGF receptor, HER2, HER3 or HER4 receptor; cell adhesion molecules such as LFA-1, Mac1, p150.95, VLA-4, ICAM-1, VCAM, $\alpha 4/\beta 7$ integrin, and $\alpha v/\beta 3$ integrin including either $\alpha$ or $\beta$ subunits thereof (e.g. anti-CD11a, anti-CD18 or anti-CD11b antibodies); growth factors such as VEGF; tissue factor (TF); alpha interferon ($\alpha$-IFN); an interleukin, such as IL-8; IgE; blood group antigens; flk2/flt3 receptor; obesity (OB) receptor; mpl receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or carbodiimide where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with for example 1/10 of the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler, et al., Nature, 256 (1975) 495, or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, Academic Press (1986) pp. 59-103).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J., Immunol. 133 (1984) 3001; Brodeur, et al., Monoclonal Antibody Production Techniques and Applications, Marcel Dekker, Inc., New York (1987) pp. 51-63).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, Academic Press (1986) pp. 59-103). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty, J., et al., Nature 348 (1990) 552-554. Clackson, et al., Nature 352 (1991) 624-628 and Marks, et al., J. Mol. Biol. 222 (1991) 581-597 describe the isolation of murine and human antibodies, respectively, using phage libraries. Subsequent publications describe the production of high affinity (nM range) human antibodies by chain shuffling (Marks, et al., Bio/Technology 10 (1992) 779-783), as well as combinatorial infection and in vivo recombination as a strategy for constructing very large phage libraries (Waterhouse, et al., Nuc. Acids. Res. 21 (1993) 2265-2266). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81 (1984) 6851-6855), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$ M to $10^{-13}$M, e.g., from $10^{-9}$ M to $10^{-13}$ M).

In one embodiment, Kd is measured by a radiolabeled antigen or Fc receptor binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., J. Mol. Biol. 293 (1999) 865-881). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen or Fc receptor CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensograms. The equilibrium dissociation constant (Kd) is calculated as the ratio $k_{off}/k_{on}$. See, e.g., Chen, et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, et al., Nat. Med. 9 (2003) 129-134. For a review of scFv fragments, see, e.g., Plückthün, in The Pharmacology of Monoclonal Antibodies, vol. 113, Rosenburg and Moore eds., (Springer-Verlag, New York), pp. 269-315 (1994); see also WO 93/16185; and U.S.

Pat. No. 5,571,894 and U.S. Pat. No. 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, et al., Nat. Med. 9 (2003) 129-134; and Hollinger, et al., Proc. Natl. Acad. Sci. USA 90 (1993) 6444-6448. Triabodies and tetrabodies are also described in Hudson, et al., Nat. Med. 9 (2003) 129-134.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

Chimeric and Humanized Antibodies

In certain embodiments, an antibody provided herein is a chimeric antibody. Certain chimeric antibodies are described, e.g., in U.S. Pat. No. 4,816,567; and Morrison, et al., Proc. Natl. Acad. Sci. USA, 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, and Fransson, Front. Biosci. 13 (2008) 1619-1633, and are further described, e.g., in Riechmann, et al., Nature 332 (1988) 323-329; Queen, et al., Proc. Nat'l Acad. Sci. USA 86 (1989) 10029-10033; U.S. Pat. Nos. 5,821,337, 7,527,791, 6,982,321, and 7,087,409; Kashmiri, et al., Methods 36 (2005) 25-34 (describing SDR (a-CDR) grafting); Padlan, Mol. Immunol. 28 (1991) 489-498 (describing "resurfacing"); Dall'Acqua, et al., Methods 36 (2005) 43-60 (describing "FR shuffling"); and Osbourn, et al., Methods 36 (2005) 61-68 and Klimka, et al., Br. J. Cancer, 83 (2000) 252-260 (describing the "guided selection" approach to FR shuffling).

Human framework regions that may be used for humanization include but are not limited to: framework regions selected using the "best-fit" method (see, e.g., Sims, et al., J. Immunol. 151 (1993) 2296); framework regions derived from the consensus sequence of human antibodies of a particular subgroup of light or heavy chain variable regions (see, e.g., Carter, et al., Proc. Natl. Acad. Sci. USA, 89 (1992) 4285; and Presta, et al., J. Immunol., 151 (1993) 2623); human mature (somatically mutated) framework regions or human germline framework regions (see, e.g., Almagro, and Fransson, Front. Biosci. 13 (2008) 1619-1633); and framework regions derived from screening FR libraries (see, e.g., Baca, et al., J. Biol. Chem. 272 (1997) 10678-10684 and Rosok, et al., J. Biol. Chem. 271 (1996) 22611-22618).

Human Antibodies

In certain embodiments, an antibody provided herein is a human antibody. Human antibodies can be produced using various techniques known in the art. Human antibodies are described generally in van Dijk, and van de Winkel, Curr. Opin. Pharmacol. 5 (2001) 368-74 and Lonberg, Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing V<small>ELOCI</small>M<small>OUSE</small>® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, J. Immunol., 133 (1984) 3001; Brodeur, et al., Monoclonal Antibody Production Techniques and Applications, Marcel Dekker, Inc., New York, (1987) pp. 51-63; and Boerner, et al., J. Immunol., 147 (1991) 86.) Human antibodies generated via human B-cell hybridoma technology are also described in L1, et al., Proc. Natl. Acad. Sci. USA, 103 (2006) 3557-3562. Additional methods include those described, for example, in U.S. Pat. No. 7,189,826 (describing production of monoclonal human IgM antibodies from hybridoma cell lines) and Ni, Xiandai Mianyixue, 26(4) (2006) 265-268 (describing human-human hybridomas). Human hybridoma technology (Trioma technology) is also described in Vollmers, and Brandlein, Histology and Histopathology 20(3) (2005) 927-937 and Vollmers, and Brandlein, Methods and Findings in Experimental and Clinical Pharmacology 27(3) (2005) 185-91.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R., et al., in Methods in Molecular Biology 178 (2002) 1-37 (O'Brien et al., ed., Human Press, Totowa, N.J., 2001) and further described, e.g., in the McCafferty, J., et al., Nature 348 (1990) 552-554; Clackson, et al., Nature 352 (1991) 624-628; Marks, et al., J. Mol. Biol. 222 (1992) 581-597; Marks, and Bradbury, in Methods in Molecular Biology 248 161-175 (Lo, ed., Human Press, Totowa, N.J., 2003); Sidhu, et al., J. Mol. Biol. 338(2) (2004) 299-310; Lee, et al., J. Mol. Biol. 340(5) (2004) 1073-1093; Fellouse, Proc. Natl. Acad. Sci. USA 101(34) (2004) 12467-12472; and Lee, et al., J. Immunol. Methods 284(1-2) (2004) 119-132.

In certain phage display methods, repertoires of VH and VL genes are separately cloned by polymerase chain reaction (PCR) and recombined randomly in phage libraries, which can then be screened for antigen-binding phage as described in Winter, et al., Ann. Rev. Immunol., 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths, et al., EMBO J, 12 (1993) 725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom, and Winter, J. Mol. Biol., 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for a specific antigen and the other is for any other antigen. In certain embodiments, bispecific antibodies may bind to two different epitopes of the antigen. Bispecific antibodies may also be used to localize cytotoxic agents to cells which express the antigen to which the antibody binds. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, and Cuello, Nature 305 (1983) 537, WO 93/08829, and Traunecker, et al., EMBO J. 10 (1991) 3655), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004 A1); cross-linking two or more antibodies or fragments (see, e.g., U.S. Pat. No. 4,676,980, and Brennan, et al., Science, 229 (1985) 81); using leucine zippers to produce bi-specific antibodies (see, e.g., Kostelny, et al., J. Immunol., 148(5) (1992) 1547-1553); using "diabody" technology for making bispecific antibody fragments (see, e.g., Hollinger, et al., Proc. Natl. Acad. Sci. USA, 90 (1993) 6444-6448); and using single-chain Fv (sFv) dimers (see, e.g. Gruber, et al., J. Immunol., 152 (1994) 5368); and preparing trispecific antibodies as described, e.g., in Tutt, et al., J. Immunol. 147 (1991) 60.

Engineered antibodies with three or more functional antigen binding sites, including "Octopus antibodies," are also included herein (see, e.g. US 2006/0025576 A1).

The antibody or fragment herein also includes a "Dual Acting FAb" or "DAF" comprising an antigen binding site that binds to a specific antigen as well as another, different antigen (see, US 2008/0069820, for example).

Antibody Variants with Altered Binding Affinity to the Antigen

In certain embodiments, it may be desirable to improve the binding affinity to the antigen and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, polypeptides comprising Fc variants additionally have one or more amino acid substitutions at other parts than the Fc part, are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, or decreased immunogenicity.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu | grouped according to common side-chain properties:
  (1) hydrophobic: Ile, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, et al., in Methods in Molecular Biology 178 (2002) 1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, and Wells, Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, et al., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

Polypeptides comprising Fc variants are further provided with sialylated oligosaccharides, e.g., in which a differential sialylation of the Fc core oligosaccharide attached to the Fc region of the antibody is provided. Such polypeptides may have increased sialylation and/or decreased ADCC function. Examples of such antibody variants are described e.g. by Kaneko, et al., Science 313 (2006) 670-673.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam, et al., Proc. Natl. Acad. Sci. USA 102 (2005) 11600-11605). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an antibody variant described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody variant is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody variant, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology 248 (2003) 245-254 (B. K. C. Lo, ed., Humana Press, Totowa, N.J.), describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22 (2004) 1409-1414, and L1, et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or kidney cells (BHK); mouse sertoli cells (TM4 cells as described, e.g., in Mather, Biol. Reprod. 23 (1980) 243-251); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, et al., Proc. Natl. Acad. Sci. USA 77 (1980) 4216); and myeloma cell lines such as Y0, NS0 and Sp2/0. For a review of certain mammalian host cell lines suitable for antibody production, see, e.g., Yazaki, and Wu, Methods in Molecular Biology 248 (2003) 255-268 (B. K. C. Lo, ed., Humana Press, Totowa, N.J.).

Assays

Antibodies provided herein may be identified, screened for, or characterized for their physical/chemical properties and/or biological activities by various assays known in the art.

Binding Assays and Other Assays

In one aspect, an antibody of the invention is tested for its antigen binding activity, e.g., by known methods such as ELISA, Western blot, etc.

In an exemplary competition assay, immobilized antigen is incubated in a solution comprising a first labeled antibody that binds to the antigen (e.g.) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen (See Harlow, and Lane (1988) Antibodies: A Laboratory Manual ch.14 (Cold Spring Harbor Laboratory, Cold Spring Harbor, N.Y.).

Immunoconjugates

The invention also provides immunoconjugates comprising an antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, et al., Cancer Res. 53 (1993) 3336-3342; and Lode, et al., Cancer Res. 58 (1998) 2925-2928); an anthracycline such as daunomycin or doxorubicin (see Kratz, et al., Current Med. Chem. 13 (2006) 477-523; Jeffrey, et al., Bioorganic & Med. Chem. Letters 16 (2006) 358-362; Torgov, et al., Bioconj. Chem. 16 (2005) 717-721; Nagy, et al., Proc. Natl. Acad. Sci. USA 97 (2000) 829-834; Dubowchik, et al., Bioorg. & Med. Chem. Letters 12 (2002) 1529-1532; King, et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, et al., Science 238 (1987) 1098. Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, et al., Cancer Res. 52 (1992) 127-131; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SLAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Methods and Compositions for Diagnostics and Detection

In certain embodiments, any of the antibody variants provided herein is useful for detecting the presence of the antigen binding to that antibody in a biological sample. The term "detecting" as used herein encompasses quantitative or qualitative detection. In certain embodiments, a biological sample comprises a cell or tissue.

In one embodiment, an antibody variant for use in a method of diagnosis or detection is provided. In a further aspect, a method of detecting the presence of the antigen to which said antibody variant binds in a biological sample is provided. In certain embodiments, the method comprises contacting the biological sample with an antibody as described herein under conditions permissive for binding of the antibody to the antigen, and detecting whether a complex is formed between the antibody and the antigen. Such method may be an in vitro or in vivo method. In one embodiment, an antibody variant is used to select subjects eligible for therapy with an antibody, e.g. where the antigen to which said antibody binds is a biomarker for selection of patients.

Exemplary disorders that may be diagnosed using an antibody of the invention include cancer, cardiovascular diseases, neuronal disorders and diabetes.

In certain embodiments, labeled antibody variants are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Formulations

Pharmaceutical formulations of an antibody variant as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Compositions

Any of the polypeptides provided herein may be used in therapeutic methods.

In a specific aspect of the invention the polypeptide according to the invention are used for treating a disease. In a more specific aspect, the disease is such, that it is favorable that the effector function of the variant is strongly, at least by 50%, reduced compared to the polypeptide comprising the wildtype Fc polypeptide.

In a specific aspect the polypeptide according to the invention is used in the manufacture of a medicament for the treatment of a disease, wherein it is favorable that the effector function of the polypeptide is strongly reduced compared to a wildtype Fc polypeptide. In a further specific aspect the polypeptide according to the invention is used in the manufacture of a medicament for the treatment of a disease, wherein it is favorable that the effector function of the polypeptide is reduced compared to a wildtype Fc polypeptide, by at least 20%.

A further aspect is a method of treating an individual having a disease, wherein it is favorable that the effector function of the variant is strongly reduced compared to a wildtype Fc polypeptide, comprising administering to the individual an effective amount of the polypeptide according to the invention.

A strong reduction of effector function is a reduction of effector function by at least 50% of the effector function induced by the wildtype polypeptide. Such diseases are for example all diseases where the targeted cell should not be destroyed by for example ADCC, ADCP or CDC. Moreover, this is true for those antibodies that are designed to deliver a drug (e.g., toxins and isotopes) to the target cell where the Fc/FcγR mediated effector functions bring healthy immune cells into the proximity of the deadly payload, resulting in depletion of normal lymphoid tissue along with the target cells (Hutchins, et al, PNAS USA 92 (1995) 11980-11984; White, et al, Annu Rev Med 52 (2001) 125-145). In these cases the use of antibodies that poorly recruit complement or effector cells would be of tremendous benefit (see for example, Wu, et al., Cell Immunol 200 (2000) 16-26; Shields, et al., J. Biol Chem 276(9) (2001) 6591-6604; U.S. Pat. No. 6,194,551; U.S. Pat. No. 5,885,573 and PCT publication WO 04/029207).

In other instances, for example, where blocking the interaction of a widely expressed receptor with its cognate ligand is the objective, it would be advantageous to decrease or eliminate all antibody effector function to reduce unwanted toxicity. Also, in the instance where a therapeutic antibody exhibited promiscuous binding across a number of human tissues it would be prudent to limit the targeting of effector function to a diverse set of tissues to limit toxicity.

Also for agonist antibodies it would be very helpful if these antibodies exhibit reduced effector function.

The conditions which can be treated with the polypeptide variant are many and include cancer (e.g. where the antibody variant binds the HER2 receptor, angiopoietin receptor or vascular endothelial growth factor (VEGF)); allergic conditions such as asthma (with an anti-IgE antibody); and LFA-1-mediated disorders (e.g. where the polypeptide variant is an anti-LFA-1 or anti-ICAM-1 antibody), neurological and metabolic disorders.

Where the antibody binds the HER2 receptor, the disorder preferably is HER2-expressing cancer, e.g. a benign or malignant tumor characterized by overexpression of the HER2 receptor. Such cancers include, but are not limited to, breast cancer, squamous cell cancer, small-cell lung cancer, non-small cell lung cancer, gastrointestinal cancer, pancreatic cancer, glioblastoma, cervical cancer, ovarian cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

The polypeptide or antibody variant is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody variant is suitably administered by pulse infusion, particularly with declining doses of the polypeptide variant. Preferably the dosing is given by injections, most preferably intravenous or subcutaneous injections, depending in part on whether the administration is brief or chronic.

For the prevention or treatment of disease, the appropriate dosage of polypeptide or antibody variant will depend on the type of disease to be treated, the severity and course of the disease, whether the polypeptide variant is administered for preventive or therapeutic purposes, previous therapy, the patient's clinical history and response to the polypeptide variant, and the discretion of the attending physician. The polypeptide variant is suitably administered to the patient at one time or over a series of treatments.

Depending on the type and severity of the disease, about 1 µg/kg to 15 mg/kg (e.g., 0.1-20 mg/kg) of polypeptide or antibody variant is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

In certain embodiments, the invention provides an antibody variant or polypeptide for use in a method of treating an individual having cancer comprising administering to the individual an effective amount of the antibody variant. In one such embodiment, the method further comprises administering to the individual an effective amount of at least one additional therapeutic agent, e.g., as described below. In further embodiments, the invention provides an antibody variant for use in inhibiting angiogenesis, inhibiting cell proliferation or depleting B-cells in an individual comprising administering to the individual an effective of the antibody variant to inhibit angiogenesis, inhibit cell proliferation or deplete B-cells in an "individual" according to any of the above embodiments is preferably a human.

In a further aspect, the invention provides for the use of an antibody variant or polypeptide in the manufacture or preparation of a medicament. In one embodiment, the medicament is for treatment of cancer or inflammatory diseases. In a further embodiment, the medicament is for use in a method of treating cancer, diabetes, neuronal disorders or inflammatory comprising administering to an individual having cancer, diabetes, neuronal disorders or inflammatory an effective amount of the medicament. In one such embodiment, the method further comprises administering to the individual an effective amount of at least one additional therapeutic agent, e.g., as described below. In a further embodiment, the medicament is for inhibiting angiogenesis, inhibiting cell proliferation or depleting B-cells.

In a further embodiment, the medicament is for use in a method of inhibiting angiogenesis, inhibiting cell proliferation or depleting B-cells in an individual comprising administering to the individual an amount effective of the medicament to inhibit angiogenesis, inhibit cell proliferation or deplete B-cells. An "individual" according to any of the above embodiments may be a human.

In a further aspect, the invention provides pharmaceutical formulations comprising any of the antibody variants provided herein, e.g., for use in any of the above therapeutic methods. In one embodiment, a pharmaceutical formulation comprises any of the antibody variants provided herein and a pharmaceutically acceptable carrier. In another embodiment, a pharmaceutical formulation comprises any of the antibody variants provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an antibody according to the invention.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an antibody variant.

Non-Therapeutic Uses for the Polypeptide

The antibody variant of the invention may be used as an affinity purification agent. In this process, the antibody variant is immobilized on a solid phase such a Sephadex resin or filter paper, using methods well known in the art. The immobilized polypeptide variant is contacted with a sample containing the antigen to be purified, and thereafter the support is washed with a suitable solvent that will remove substantially all the material in the sample except the antigen to be purified, which is bound to the immobilized antibody variant. Finally, the support is washed with another suitable solvent, such as glycine buffer, pH 5.0, that will release the antigen from the polypeptide variant.

The antibody variant may also be useful in diagnostic assays, e.g., for detecting expression of an antigen of interest in specific cells, tissues, or serum.

For diagnostic applications, the antibody variant typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The polypeptide variant can be labeled with the radioisotope using the techniques described in Coligen, et al., Current Protocols in Immunology, Volumes 1 and 2, Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the polypeptide variant using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as unease and xanthine oxidase), lactoperoxidase, microperoxidase, and the like. Techniques for conjugating enzymes to antibodies are described in O'Sullivan, et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the polypeptide variant. The skilled artisan will be aware of various techniques for achieving this. For example, the polypeptide variant can be conjugated with biotin and any of the three broad categories of labels mentioned above can be conjugated with avidin, or vice versa. Biotin binds selectively to avidin and thus, the label can be conjugated with the polypeptide variant in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved.

In another embodiment of the invention, the antibody variant need not be labeled, and the presence thereof can be detected using a labeled antibody which binds to the polypeptide variant.

The antibody variant of the present invention may be employed in any known assay method, such as competitive binding assays, direct and indirect sandwich assays, and immunoprecipitation assays. Zola, Monoclonal Antibodies: A Manual of Techniques, (1987) pp. 147-158, CRC Press, Inc.

The antibody variant may also be used for in vivo diagnostic assays. Generally, the polypeptide variant is labeled with a radionuclide (such as $^{111}$In, $^{99}$Tc, $^{14}$C, $^{131}$I, $^{125}$I, $^{3}$H, $^{32}$P or $^{35}$S) so that the antigen or cells expressing it can be localized using immunoscintiography. Although the foregoing invention has been described in some detail by way of illustration and example for purposes of clarity of understanding, the descriptions and examples should not be construed as limiting the scope of the invention.

Description of the Sequence Listing:
SEQ ID NO:1 Human kappa light chain
SEQ ID NO:2 Human lambda light chain
SEQ ID NO:3 Human IgG1 (Caucasian Allotype)
SEQ ID NO:4 Human IgG1 (Afroamerican Allotype
SEQ ID NO:5 Human IgG1 LALA-Mutant (Caucasian Allotype)
SEQ ID NO:6 Human IgG4
SEQ ID NO:7 Human IgG4 SPLE-Mutant which represent exemplary human sequences for the kappa light chain, lambda light chain, IgG1 and IgG4 which could serve as basis for generating the variants according to the invention.
  In sequence Id Nos 3-5, the sequence of human IgG1 allotypes, the P329 region according to Kabat EU index is located at position 212, whereas said P329 region in sequence Id Nos 6 and 7 can be find at position 209.
SEQ ID NO:8 Kappa light chain of mAb 40A746.2.3
SEQ ID NO:9 Heavy chain of wildtype IgG1 of mAb 40A746.2.3
SEQ ID NO:10 Heavy chain of IgG1 P329G of mAb 40A746.2.3
SEQ ID NO:11 Heavy chain of IgG1 LALA/P329G of mAb 40A746.2.3
SEQ ID NO:12 Heavy chain of IgG4 SPLE of mAb 40A746.2.3
SEQ ID NO:13 Heavy chain of IgG4 SPLE/P329G of mAb 40A746.2.3
SEQ ID NO:14 Heavy chain of IgG1 LALA of mAb 40A746.2.3

EXAMPLES

The following seven examples are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1

Antibodies

For the experiments described below antibodies against CD9 (see SEQ IDs 8-14), P-selectin (sequences described in WO 2005/100402) and CD20 (synonym: GA101, sequences described in EP 1 692 182) were used.

All variants described herein, e.g. P329G, P329A, P329R SPLE, LALA, P329G/LALA, P329G/SPLE variants of the selectin, CD9, CD20 (GA101) and CD20 (GA101)-glycoengineered binding antibody (numbering according to EU nomenclature) were generated using PCR based mutagenesis. IgG molecules were expressed in the HEK-EBNA or HEK293 (CD9 Fc variants) system, and purified using protein A and size exclusion chromatography.

Example 2

Determination of the Binding Affinities of Different Fcγ Receptors to Immunoglobulins Binding affinities of different FcγRs towards immunoglobulins were measured by Surface Plasmon Resonance (SPR) using a Biacore T100 instrument (GE Healthcare) at 25° C.

The BIAcore® system is well established for the study of molecule interactions. It allows a continuous real-time monitoring of ligand/analyte bindings and thus the determination of association rate constants ($k_a$), dissociation rate constants ($k_d$), and equilibrium constants ($K_D$). Changes in the refractive index indicate mass changes on the surface caused by the interaction of immobilized ligand with analyte injected in solution. If molecules bind immobilized ligands on the surface the mass increases, in case of dissociation the mass decreases.

For a 1:1 interaction no difference in the results should be seen if a binding molecule is either injected over the surface or immobilized onto a surface. Therefore different settings were used (with Fcγ receptor as ligand or analyte respectively), depending on solubility and availability of ligand or corresponding analyte.

For FcγRI 10000 resonance units (RU) of a capturing system recognizing a polyhistidine sequence (pentaHis monoclonal antibody, Qiagen Hilden, cat. no. 34660) was immobilized by the use of an amine coupling kit supplied by the GE Healthcare and a CM5 chip at pH 4.5. FcγRI was captured at a concentration of 5 μg/ml by with a pulse of 60 sec at a flow of 5 μl/min. Different concentrations of antibodies ranging from 0 to 100 nM were passed with a flow rate of 30 μl/min through the flow cells at 298 K for 120 sec to record the association phase. The dissociation phase was monitored for up to 240 sec and triggered by switching from the sample solution to running buffer. The surface was regenerated by 2 min washing with a glycine pH 2 solution at a flow rate of 30 ml/min. For all experiments HBS-P+ buffer supplied by GE Healthcare was chosen (10 mM HEPES, pH 7.4, 150 mM NaCl, 0.05% (v/v) Surfactant P20). Bulk refractive index differences were corrected for by subtracting the response obtained from a surface without captured FcγRI. Blank injections are also subtracted (=double referencing).

The equilibrium dissociation constant ($K_D$), defined as $k_a/k_d$, was determined by analyzing the sensogram curves obtained with several different concentrations, using BIAevaluation software package. The fitting of the data followed a suitable binding model.

For FcγRIIA and FcγRIIIAV158 10000 resonance units (RU) of a monoclonal antibody to be tested was immobilized onto a CM5 chip by the use of an amine coupling kit supplied by the GE (pH 4.5 at a concentration of 10 µg/ml).

Different concentrations of FcγRIIA and 111A ranging from 0 to 12800 nM were passed with a flow rate of 5 µl/min through the flow cells at 298 K for 120 sec to record the association phase. The dissociation phase was monitored for up to 240 sec and triggered by switching from the sample solution to running buffer. The surface was regenerated by 0.5 min washing with a 3 mM NaOH/1M NaCl solution at a flow rate of 30 ml/min. For all experiments HBS-P+ buffer supplied by GE Healthcare was chosen (10 mM HEPES, pH 7.4, 150 mM NaCl, 0.05% (v/v) Surfactant P20).

Bulk refractive index differences were corrected for by subtracting the response obtained from a surface without captured antibody. Blank injections are also subtracted (=double referencing).

The equilibrium dissociation constant ($K_D$), was determined by analyzing the sensogram curves obtained with several different concentrations, using BIA evaluation software package. The fitting of the data followed a suitable binding model using steady state fitting For FcγRIIB 10000 resonance units (RU) of a capturing system recognizing a polyhistidine sequence (pentaHis monoclonal antibody, Qiagen Hilden, cat. no. 34660) was immobilized by the use of an amine coupling kit supplied by the GE Healthcare and a CM5 chip at pH 4.5. FcγRIIB was captured at a concentration of 5 µg/ml by with a pulse of 120 sec at a flow of 5 µl/min. Different antibodies were passed at a concentration of 1340 nM with a flow rate of 5 µl/min through the flow cells at 298 K for 60 sec to record the association phase. The dissociation phase was monitored for up to 120 sec and triggered by switching from the sample solution to running buffer. The surface was regenerated by 0.5 min washing with a glycine pH2.5 solution at a flow rate of 30 ml/min. For all experiments HBS-P+ buffer supplied by GE Healthcare was chosen (10 mM HEPES, pH 7.4, 150 mM NaCl, 0.05% (v/v) Surfactant P20).

Bulk refractive index differences were corrected for by subtracting the response obtained from a surface without captured FcγRIIB. Blank injections are also subtracted (=double referencing).

Due to the very low intrinsic affinity of FcγRIIB to wild-type IgG1 no affinity was calculated rather a qualitative binding was assessed.

The following tables summarize the effects of introducing a mutation into the Fc part on binding to FcγRI, FcγRIIA, FcγRIIB, and FcγRIIIAV1-58 (A) as well as the effect on ADCC (measured without (BLT) and with target cells (ADCC)) and on C1q binding (B)

TABLE 2A

|  | FcγRI | FcγRIIaR131 | FcγRIIIAV158 | FcγRIIB |
|---|---|---|---|---|
| WT IgG1 | ++ (5 nM) | ++ (2 µM) | + (0.7 µM) | ++ |
| IgG4 SPLE | - | +/- (10 µM) | - (>20 µM) | + |
| IgG1 P329G | ++ (6 nM) | - (>20 µM) | - (>20 µM) | - |
| IgG1 P329A ge | ++ (8 nM) | + (4.4 µM) | + (1.8 µM) | + |
| IgG1 P329G LALA | - | - (>20 µM) | - (>20 µM) | - |
| IgG1 P329G ge | ++ (10 nM) | - (>20 µM) | - (>10 µM) *++ for ge IgG1 30 nM | - |

TABLE 2B

| Mutant | FcγRI | FcγRII | FcγRIII | C1q Assay | | ADCC without target cells | ADCC with target cells |
|---|---|---|---|---|---|---|---|
|  | Biacore | Biacore | Biacore | CDC | C1q | BLT | ADCC |
| P329G | + | -- | -- | -- | -- | -- | -- |
| P329R | n.d. | n.d. | n.d. | n.d. | n.d. | -- | -- |
| LALA | - | n.d. | - | - | n.d. | n.d. | -- |
| IgG1_P329G/LALA | -- | -- | -- | n.d. | n.d. | n.d. | n.d. |
| IgG4_SPLE | -- | - | -- | -- | -- | n.d. | n.d. |

Figure 1B:
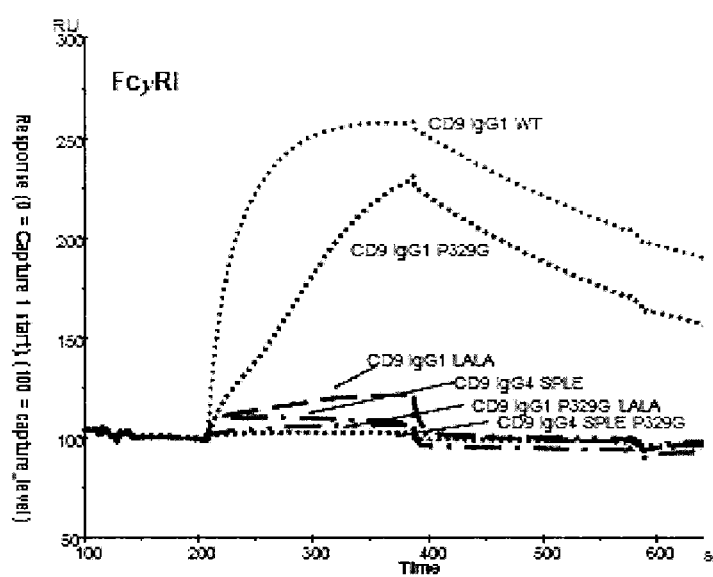

-- strongly reduced/inactive in contrast to wt,
- reduced in contrast to wt,
+ comparable to wt interaction,
n.d. not determined, /no result In more detail the following results have been obtained:
Affinity to the FcγRI Receptor P329G, P329A, SPLE and LALA mutations have been introduced into the Fc polypeptide of a P-selectin, CD20 and CD9 antibody, and the binding affinity to FcγRI was measured with the Biacore system. Whereas the antibody with the P329G mutation still binds to FcγR1 (FIGS. 1a and 1b), introduction of triple mutations P329G/LALA and P329G/SPLE, respectively, resulted in antibodies for which nearly no binding could be detected (FIG. 1b). The LALA or SPLE mutations decreased binding to the receptor more than P329G alone but less than in combination with P329G (FIGS. 1a and 1b). Thus, the combination of P329G with either LALA or SPLE mutations is much more effective than the P329G mutation or the double mutations LALA or SPLE alone. The kd value for the CD20 IgG1 wildtype antibody was 4.6 nM and for the P329G mutant of the same antibody 5.7 nM, but for the triple mutant P329G/LALA no kd value could be determined due to the nearly undetectable binding of the antibody to the FcγRI receptor. The antibody itself, i.e. whether a CD9 or CD20 or P-selectin was tested, has a minor effect on the binding affinities.

Affinity to the FcγRIIA Receptor

Figure 1C:
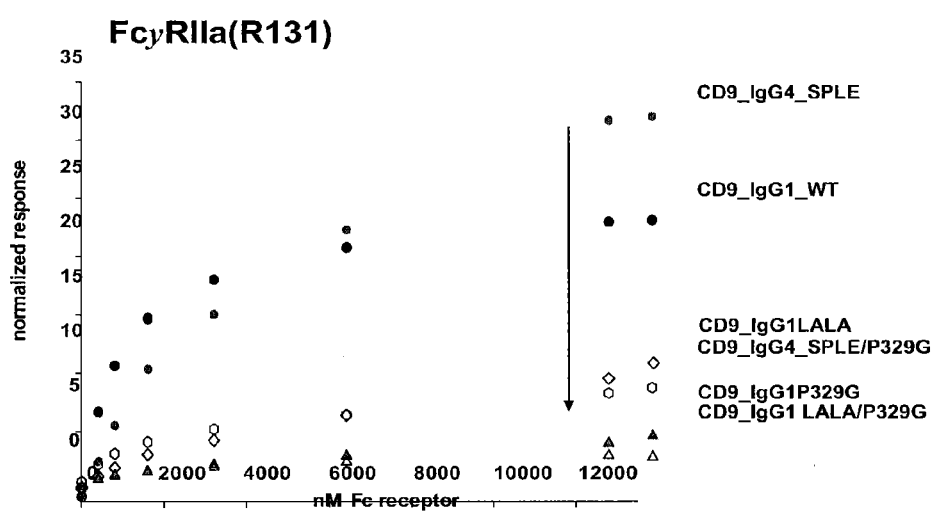

P329G, SPLE and LALA mutations, respectively, have been introduced into the Fc polypeptide of the CD9 antibody and the binding affinity to the FcγRIIA-R131 receptor was measured with the Biacore system. Binding level is normalized such as captured mAb represents 100 RU. So not more than approximately 20 RU is expected for a 1:1 stoichiometry. FIG. 1c shows that the binding to the FcγRIIA receptor is strongly reduced by introducing the LALA, SPLE/P329G, P329G and LALA/P329G mutation into the Fc variant. In contrast to binding to the FcγR1 receptor, the introduction of the P329G mutation alone is able to very strongly block the binding to said receptor, more or less to a similar extent as the triple mutation P329G/LALA (FIG. 1c).

Affinity to the FcγRIIB Receptor

Figure 1D:
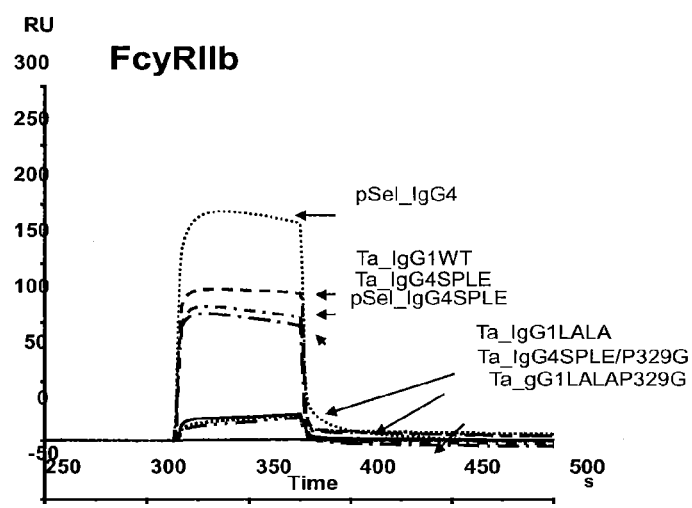
Figure 1E:
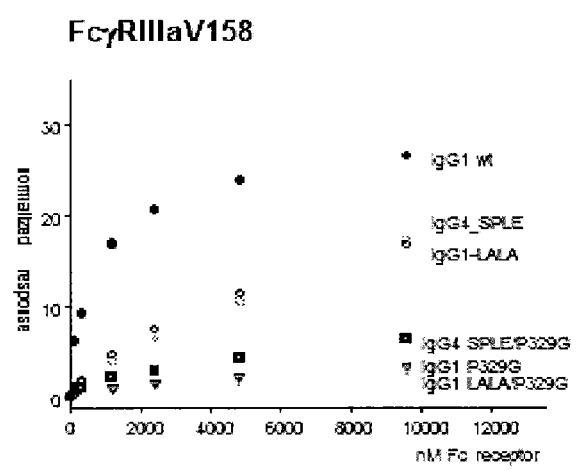

SPLE, LALA, SPLE/P329G and LALA/P329G mutations, respectively, have been introduced into the Fc polypeptide of the CD9 and P-selectin antibody and the binding affinity to FcγRIIB receptor was measured with the Biacore system. FIG. 1d shows that the binding to the FcγRIIB receptor is strongly reduced in the LALA and triple mutants P329G/LALA, P329G/SPLE Affinity to the FcγRIIIA Receptor P329G, LALA, SPLE, P329G/LALA, and SPLE/P329G mutations have been introduced into the Fc polypeptide of the CD9 and the binding affinity to FcγRIIIA-V158 receptor was measured with the Biacore system. The P329G mutation and the triple mutation P329G/LALA reduced binding to the FcγRIIIA receptor most strongly, to nearly undetectable levels. The P329G/SPLE also lead to a strongly reduced binding affinity, the mutations SPLE and LALA, respectively, only slightly decreased the binding affinity to the FcγRIIIA receptor (FIG. 1e).

Example 3

C1Q ELISA

The binding properties of the different polypeptides comprising Fc variants to C1q were analyzed by an ELISA sandwich type immunoassay. Each variant is coupled to a hydrophobic Maxisorp 96 well plate at 8 concentrations between 10 µg/ml and 0 µg/ml. This coupling simulates complexes of antibodies, which is a prerequisite for high affinity binding of the C1q molecule. After washing, the samples are incubated to allow C1q binding. After further washing the bound C1q molecule is detected by a polyclonal rabbit anti-hC1q antibody. Following the next washing step, an enzyme labelled anti-rabbit-Fcγ specific antibody is added. Immunological reaction is made visible by addition of a substrate that is converted to a coloured product by the enzyme. The resulting absorbance, measured photometrically, is proportional to the amount of C1q bound to the antibody to be investigated. $EC_{50}$ values of the variant-C1q interaction were calculated. The absorption units resulting from the coloring reaction are plotted against the concentration of the antibody. The antibody concentration at the half maximum response determines the $EC_{50}$ value. This read-out is reported as relative difference to the reference standard measured on the same plate together with the coefficient of variation of sample and reference.

Figure 2:
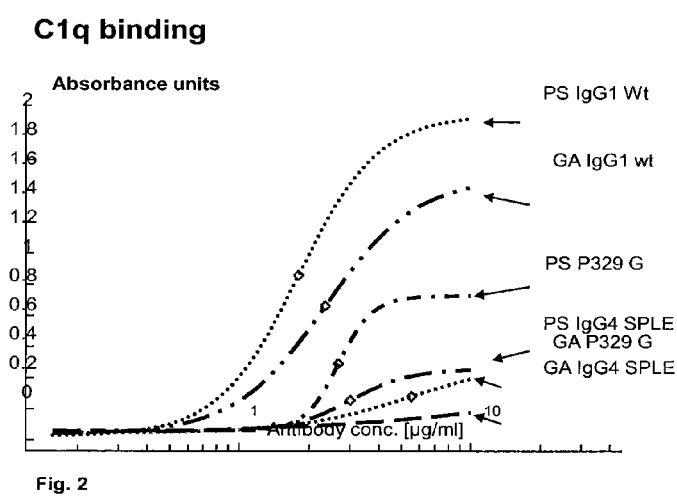

The P329G mutation introduced into the P-selectin or CD20 antibody strongly reduced binding to C1q, similar to the SPLE mutation (FIG. 2). Table 3 summarizes the calculated EC 50 values for binding of the variants to the C1q receptor. C1q belongs to the complement activation proteins and plays a major role in the activation of the classical pathway of the complement, which leads to the formation of the membrane attack complex. C1q is also involved in other immunological processes such as enhancement of phagocytosis, clearance of apoptotic cells or neutralization of virus. Thus, it can be expected that the mutants shown here to reduce binding to C1q, e.g. P329G and SPLE, as well as very likely also the triple mutations comprising the aforementioned single mutations, strongly reduces the above mentioned functions of C1q.

TABLE 3

| Antibody | EC50 value |
| --- | --- |
| P-Selectin IgG1wt | 1.8 |
| GA101 IgG1 wt | 2.4 |
| P-Selectin IgG1_P329G | 2.7 |
| P-Selectin IgG4 SPLE | 3.0 |
| GA101 IgG1 P329G | 5.5 |
| GA101 IgG4 SPLE | >10 |

Example 4

ADCC without Target Cells, BLT Assay

The antibodies to be tested (CD20 (GA101) and CD9) were coated in PBS over night at 4° C. in suitable 96-flat bottom well plates. After washing the plate with PBS, the remaining binding sites were blocked with PBS/1% BSA solution for 1 h at RT. In the meantime, the effector cells (NK-92 cell line transfected to express low or high affine human FcγRIII) were harvested and 200 000 living cells/well were seeded in 100 µl/well AIM V medium into the wells after discarding the blocking buffer. 100 µl/well saponin buffer (0.5% saponin+1% BSA in PBS) was used to determine the maximal esterase release by the effector cells. The cells were incubated for 3 h at 37° C., 5% CO2 in a incubator. After 3 h, 20 µl/well of the supernatants were mixed with 180 µl/well BLT substrate (0.2 mM BLT+0.11 mM DTNB in 0.1 M Tris-HCL, pH 8.0) and incubated for 30 min at 37° C. before reading the plate at 405 nm in a microplate reader. The percentage of esterase release was determined setting the maximal release (saponin-treated cells) to 100% and the unstimulated cells (no ab coated) to 0% release.

Figure 3A:
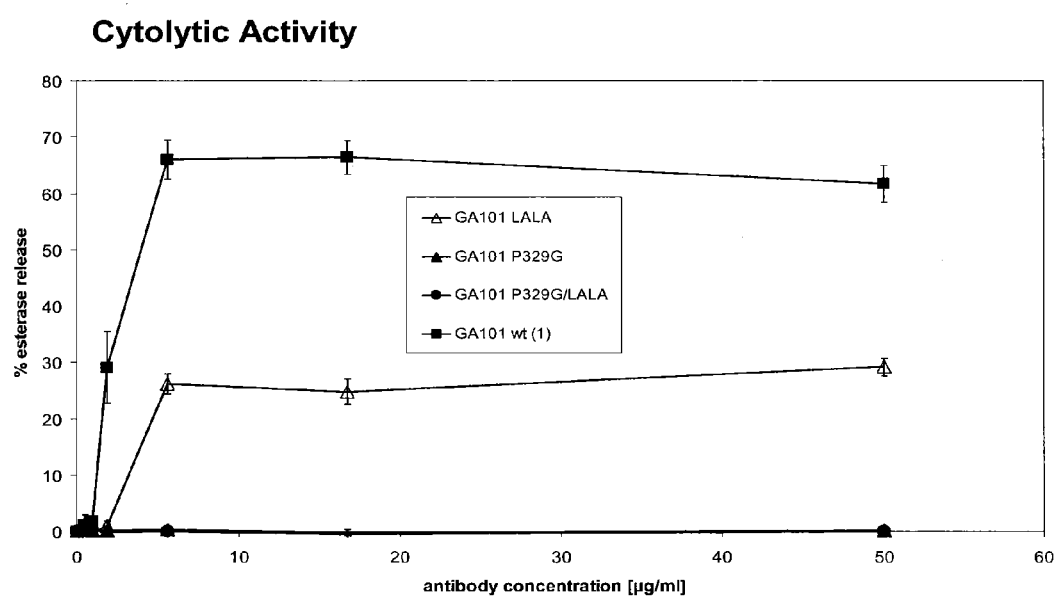
Figure 3B:
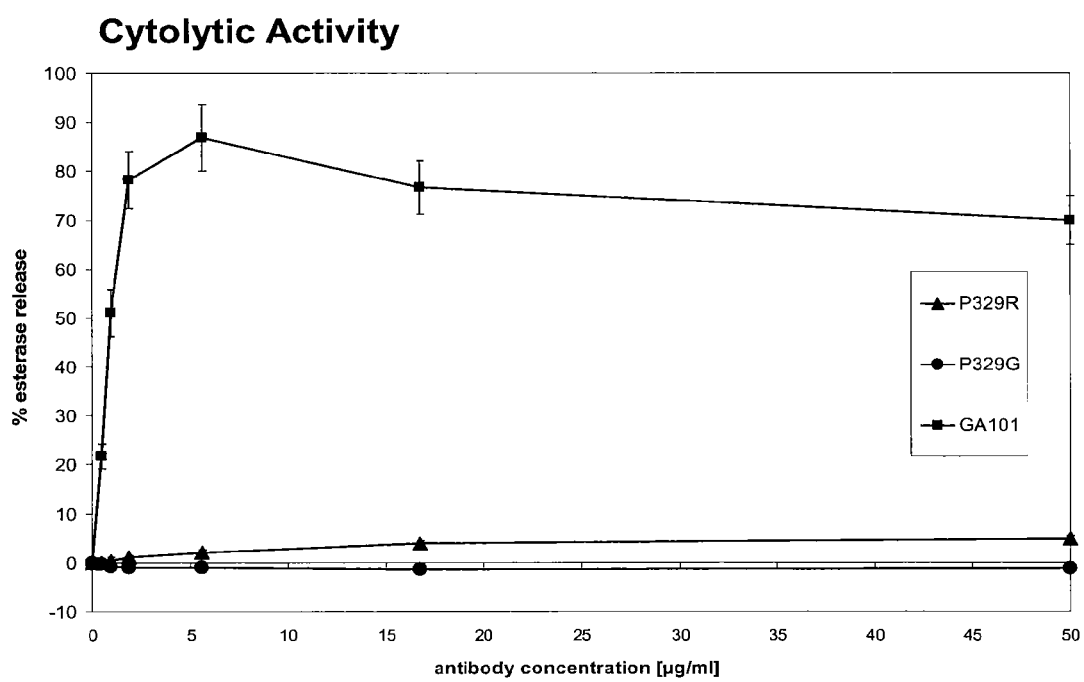

The wildtype CD20 antibody (GA101 wt (1)) shows strong induction of cytolytic activity. The LALA variant shows a marked reduction in esterase release, whereas the P329G and the P329G/LALA variant do not show any ADCC activity (FIG. 3a). FIG. 3b shows that not only an exchange of G at position P329 leads to markedly reduced cytosolic activity but also an exchange of P329 to R329 (CD20 antibody). Thus arginine appears to destroy the function of the proline sandwich in the antibody, similar to glycine. The strongly reduced ADCC observed here for the P329G mutant most likely resulted from the strongly reduced binding to the FcγRIIA and FcγRIIIA receptor (see FIG. 1c and FIG. 1e).

Example 5

ADCC with Target Cells

Human peripheral blood mononuclear cells (PBMC) were used as effector cells and were prepared using Histopaque-1077 (Sigma Diagnostics Inc., St. Louis, Mo. 63178 USA) and following essentially the manufacturer's instructions. In brief, venous blood was taken with heparinized syringes from volunteers. The blood was diluted 1:0.75-1.3 with PBS (not containing Ca++ or Mg++) and layered on Histopaque-1077. The gradient was centrifuged at 400×g for 30 min at room temperature (RT) without breaks. The interphase containing the PBMC was collected and washed with PBS (50 ml per cells from two gradients) and harvested by centrifugation at 300×g for 10 minutes at RT. After resuspension of the pellet with PBS, the PBMC were counted and washed a second time by centrifugation at 200×g for 10 minutes at RT. The cells were then resuspended in the appropriate medium for the subsequent procedures. The effector to target ratio used for the ADCC assays was 25:1 and 10:1 for PBMC and NK cells, respectively. The effector cells were prepared in AIM-V medium at the appropriate concentration in order to add 50 ml per well of round bottom 96 well plates. Target cells were human B lymphoma cells (e.g., Raji cells) grown in DMEM containing 10% FCS. Target cells were washed in PBS, counted and resuspended in AIM-V at 0.3 million per ml in order to add 30'000 cells in 100 ml per microwell. Antibodies were diluted in AIM-V, added in 50 ml to the pre-plated target cells and allowed to bind to the targets for 10 minutes at RT. Then the effector cells were added and the plate was incubated for 4 hours at 37° C. in a humified atmosphere containing 5% $CO_2$. Killing of target cells was assessed by measurement of lactate dehydrogenase (LDH) release from damaged cells using the Cytotoxicity Detection kit (Roche Diagnostics, Rotkreuz, Switzerland). After the 4-hour incubation the plates were centrifuged at 800×g. 100 ml supernatant from each well was transferred to a new transparent flat bottom 96 well plate. 100 ml color substrate buffer from the kit were added per well. The $V_{max}$ values of the color reaction were determined in an ELISA reader at 490 nm for at least 10 min using SOFTmax PRO software (Molecular Devices, Sunnyvale, Calif. 94089, USA). Spontaneous LDH release was measured from wells containing only target and effector cells but no antibodies. Maximal release was determined from wells containing only target cells and 1% Triton X-100. Percentage of specific antibody-mediated killing was calculated as follows: $((x-SR)/(MR-SR))*100$, where x is the mean of Vmax at a specific antibody concentration, SR is the mean of Vmax of the spontaneous release and MR is the mean of $V_{max}$ of the maximal release.

Figure 4A:
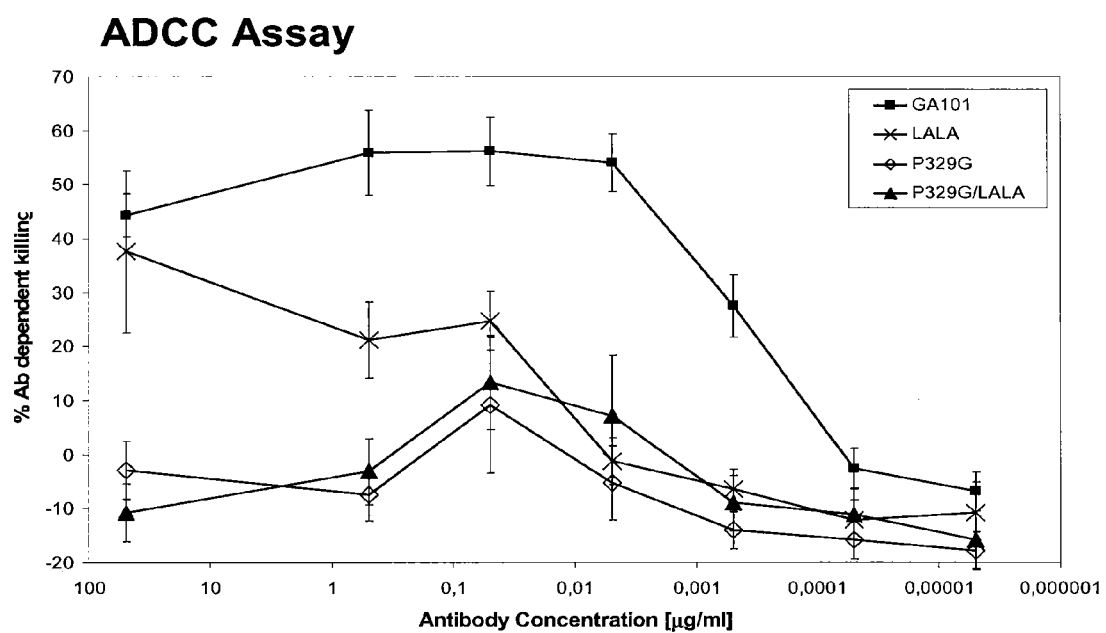
Figure 4B:
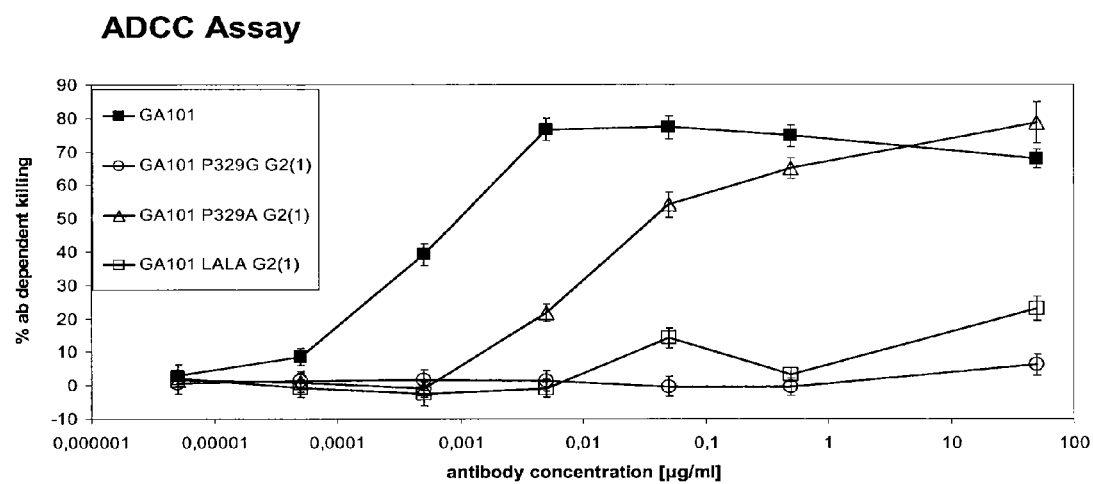

The potency to recruit immune-effector cells depends on type of Fc variant as measured by classical ADCC assay. Here, human NK92 cell-line transfected with human FcgRIIIA was used as effector and CD20 positive Raji cells were used as target cells. As can be seen in FIG. 4a the ADCC is strongly reduced in GA101 (CD20) Fc variants wherein glycine replaces proline (P329G) and also, to a similar extent, in the double mutant P329G/LALA. In contrast the ADCC decrease was less strong with the LALA mutation. In order to better distinguish between the different variants, the variants were also produced in the glycoengineered version to enhance the ADCC potential. It can be observed that the parental molecule (GA101 (CD20)) shows strong ADCC as expected. The LALA version is strongly impaired in its ADCC potential. The P329G mutant very strongly decreased the ADCC; much more than a P329A variant of the GA101 (CD20) antibody (FIG. 4b).

Example 6

Complement Activity

Target cells were counted, washed with PBS, resuspended in AIM-V (Invitrogen) at 1 million cells per ml. 50 ml cells were plated per well in a flat bottom 96 well plate. Antibody dilutions were prepared in AIM-V and added in 50 ml to the cells. Antibodies were allowed to bind to the cells for 10 minutes at room temperature. Human serum complement (Quidel) was freshly thawed, diluted 3-fold with AIM-V and added in 50 ml to the wells. Rabbit complement (Cedarlane Laboratories) was prepared as described by the manufacturer, diluted 3-fold with AIM-V and added in 50 ml to the wells. As a control, complement sources were heated for 30 min at 56° C. before addition to the assay. The assay plates were incubated for 2 h at 37° C. Killing of cells was determined by measuring LDH release. Briefly, the plates were centrifuged at 300×g for 3 min. 50 ml supernatant per well were transferred to a new 96 well plate and 50 ml of the assay reagent from the Cytotoxicity Kit (Roche) were added. A kinetic measurement with the ELISA reader determined the Vmax corresponding with LDH concentration in the supernatant. Maximal release was determined by incubating the cells in presence of 1% Triton X-100.

Figure 5A:
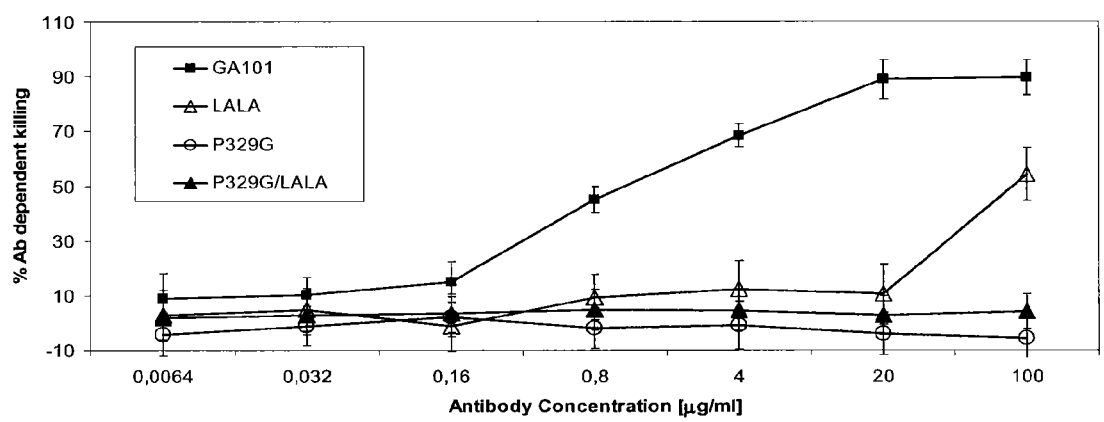
Figure 5B:
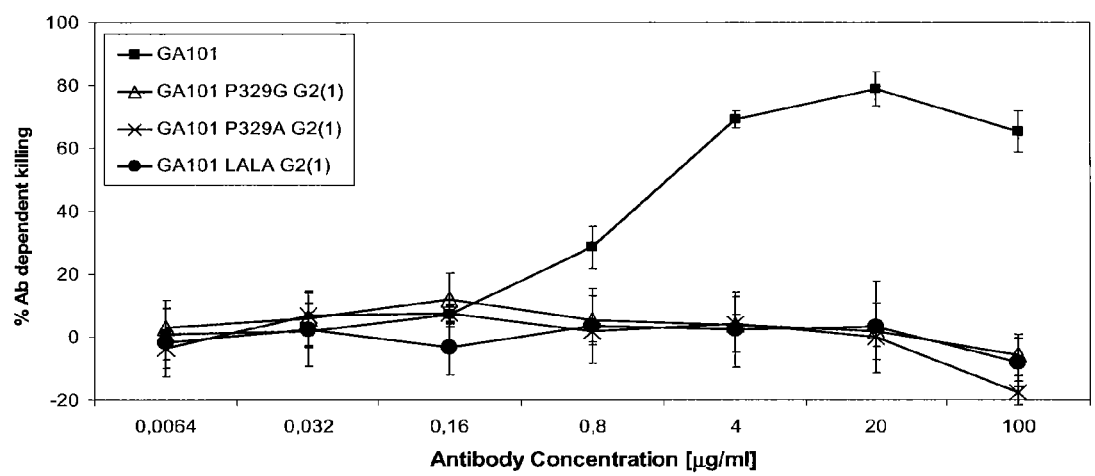

The different Fc variants were analyzed to mediate CDC on SUDH-L4 target cells. The non-glycoengineered GA101 molecule shows clear induction of CDC. The LALA variant shows activity only at the highest concentration, whereas and the P329G and P329G/LALA variants do not show any CDC activity (FIG. 5a). Moreover, the LALA variant as well as the P329G and P329A variants of a glycoengineered GA101 molecule do not show any CDC activity (FIG. 5b).

Example 7

Carbohydrate Profile of Human IgG1

The carbohydrate profiles of human IgG1 antibodies containing mutations within the Fc, aimed at abrogating the binding to Fcγ receptors, were analyzed by MALDI/TOF-MS in positive ion mode (neutral oligosaccharides).

Human (h) IgG1 variants were treated with sialidase (QA-Bio) following the manufacturer's instructions to remove terminal sialic acid. The neutral oligosaccharides of hIgG1 were subsequently released by PNGase F (QA-Bio) digestion as previously described (Ferrara, C. et al., Biotech. Bioeng. 93 (2006) 851-861). The carbohydrate profiles were analyzed by mass spectrometry (Autoflex, Bruker Daltonics GmbH) in positive ion mode as previously described (Ferrara, C. et al., Biotech. Bioeng. 93 (2006) 851-861).

The carbohydrate profile of the neutral Fc-associated glycans of human IgG1 is characterized by three major m/z peaks, which can be assigned to fucosylated complex oligosaccharide with none (G0), one (G1) or two (G2) terminal galactose residues.

The carbohydrate profiles of hIgG1 containing mutations within the Fc, aimed at abrogating binding to Fc receptors, were analyzed and compared to that obtained for the wild type antibody. The IgG variants containing one of the mutations within the Fc (P329G, LALA, P329A, P329G/LALA) show similar carbohydrate profiles to the wild type antibody, with the Fc-associated glycans being fucosylated complex oligosaccharides (data not shown). Mutation within the Fc can affect the level of terminal galactosylation and terminal sialylation, as observed by replacing amino acid at positions 241, 243, 263, 265, or 301 by alanine (Lund, J. et al., J. Immunol. 157 (1996) 4963-4969).

Figure 6A:
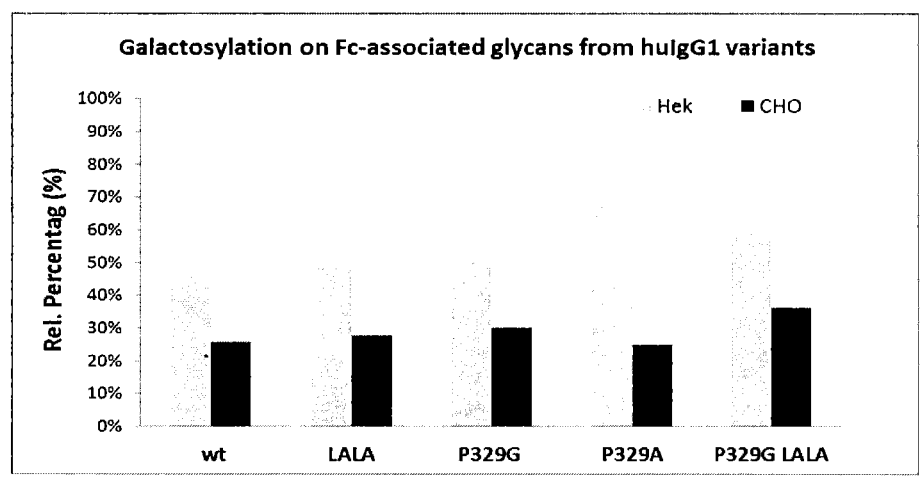

FIG. 6a shows the relative percentage of galactosylation for the different hIgG1 Fc-variants described here. Slight variations can be observed when the antibodies are expressed in a different host, but no significant difference in terminal galactosylation could be observed.

Figure 6B:
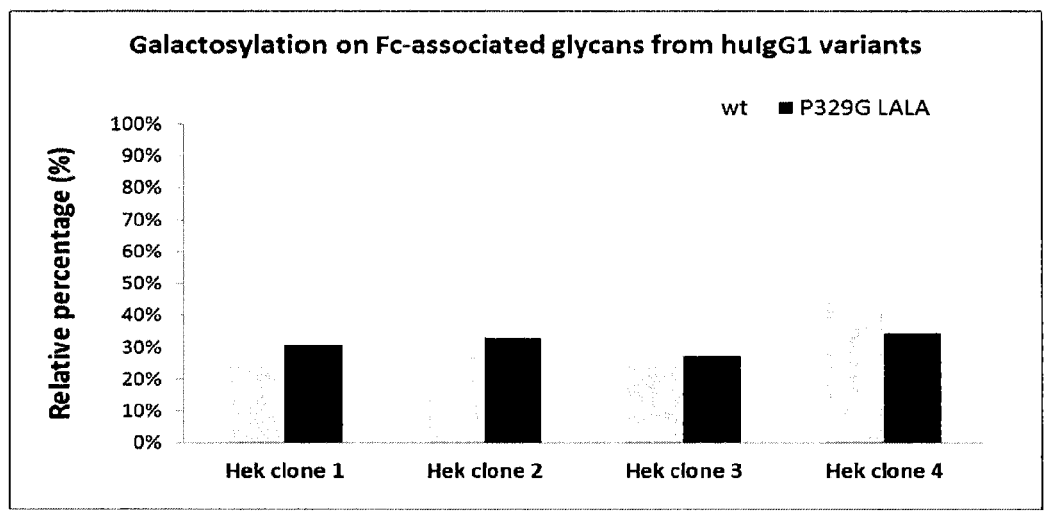

FIG. 6b indicates the variability in galactosylation content for wild type and IgG1-P329G/LALA for 4 different antibodies, where four different V-domains were compared for their amount of galactosylation when expressed in Hek293 EBNA cells.

Example 8

Antibody-Induced Platelet Aggregation in Whole Blood Assay

Whole blood platelet aggregation analysis using the Multiplate instrument from Dynabyte. First, 20 ml blood from normal human donors are withdrawn and transferred into hiruidin tubes (Dynabyte Medical, # MP0601). Plug minicell impedance device (Dynabead #MP0021) into the Multiplate instrument was used for the assay. Then, 175 µl 0.9% NaCl were added to the minicell. Antibody was added to minicell to obtain the final test concentration. Then, 175 µl human blood were added and incubated for 3 min at 37° C. Automated start of impedance analysis for additional 6 min at 37° C. The data were analyzed by quantification of area-under-the-curve as a measure of platelet aggregation.

The CD9 antibody has been shown to induce platelet activation and platelet aggregation (Worthington, et al., Br. J. Hematol. 74(2) (1990) 216-222). Platelet aggregation induced by antibodies binding to platelets previously has been shown to involve binding to FcγRIIA (de Reys, et al., Blood 81 (1993) 1792-1800). As shown above the mutations LALA, P329G, P329G/LALA and P329G/SPLE introduced into the CD9 antibody strongly reduced binding of the CD9 antibody to the FcγRIIA receptor (FIG. 1c).

Figure 7A:
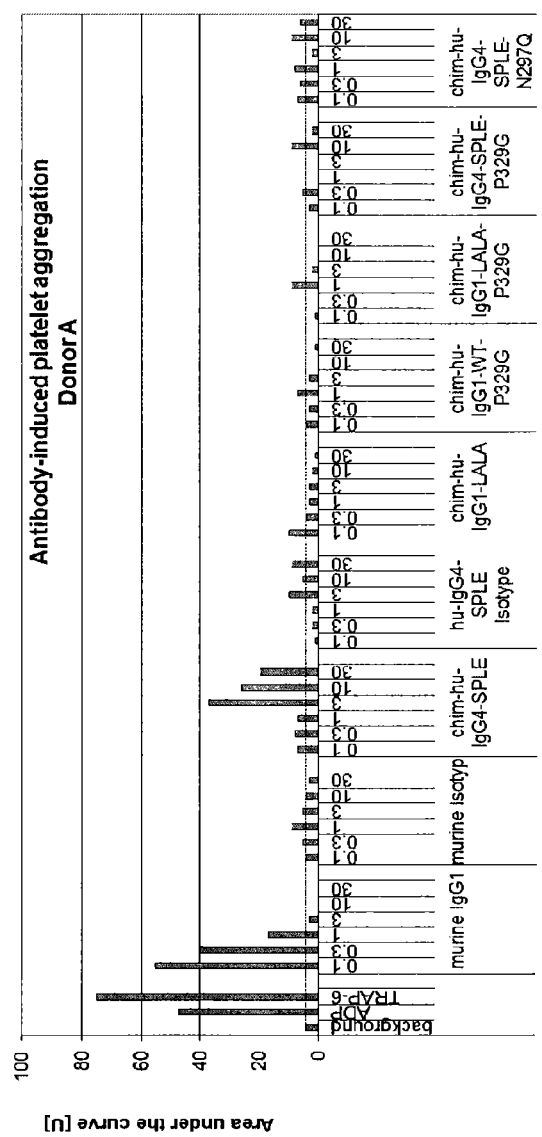

The activation (measured by Ca efflux, data not shown) as well as platelet aggregation induced by a CD9 antibody was eliminated by introducing the P329G and LALA triple mutation into the antibody such that the Fcγ/RITA binding is strongly reduced compared to the wildtype antibody (see FIGS. 7a and 7b). Murine IgG1 induced platelet aggregation at low antibody concentrations (0.1-1 µ/ml). At higher concentrations overstimulation of platelets leads to silencing of the aggregation response (3-30 µg/ml). Donor variability was observed with chim-hu-IgG4-SPLE. In FIG. 6a data for a chim-hu-IgG4-SPLE responder at higher antibody concentrations and in FIG. 6b data for a chim-hu-IgG4-SPLE non-responder is shown. None of the blood samples showed any aggregation response with the antibody variants chim-hu-IgG1-LALA, chim-hu-IgG-WT-P329G, chim-hu-IgG1-LALA-P329G, chim-hu-IgG4-SPLE-P329G, chim-hu-IgG4-SPLE-N297Q. Controls: spontaneous aggregation in untreated blood sample (background); ADP-induced (ADP) and Thrombin analogon-induced (TRAP6) platelet aggregation. Isotype controls: Murine IgG1 (murine Isotype) and human IgG4-SPLE (hu-IgG4-SPLE Isotype).

One possible interpretation of these data is that the decreased binding of the CD9 antibody with the triple mutations to the FcγRIIA receptor is the reason for the diminished platelet aggregation observed with these kind of mutant antibodies. In principle, prevention of thrombocyte aggregation, as a toxic side-effect of an antibody treatment, might thus be possible by introducing the above mentioned mutations, capable of reducing binding to the FcγRIIA receptor, into the Fc part of an antibody.

The invention claimed is:

1. An isolated polypeptide comprising an Fc variant of a wild-type human IgG1 Fc region or a wild-type human IgG4 Fc region, said Fc variant comprising an amino acid substitution at position Pro329 with glycine or arginine and at least one further amino acid substitution, wherein said at least one further amino acid substitution is L234A and L235A of the human IgG1 Fc region or S228P and L235E of the human IgG4 Fc region wherein the residues are numbered according to the EU index of Kabat, and wherein said polypeptide exhibits a reduced affinity to human FcγRIIIA, and FcγRIIA, and FcγRI compared to the polypeptide comprising the wild-type IgG Fc region, wherein the affinity to each of human FcγRIIIA, and FcγRIIA, and FcγRI is reduced by 1.15 fold to 100 fold compared to the polypeptide comprising the wild-type IgG Fc region, and wherein the antibody-dependent cell-mediated cytotoxicity (ADCC) induced by said polypeptide is 0-20% of the ADCC induced by the polypeptide comprising the wild-type human IgG Fc region.

2. The polypeptide according to claim 1, wherein the affinity to at least one further human receptor is reduced by 1.15 fold to 100 fold compared to the polypeptide comprising the wild-type human IgG Fc region, wherein the further human receptor is C1q.

3. The polypeptide according to claim 1, wherein the polypeptide is an antibody or an Fc fusion protein.

4. The polypeptide according to claim 1, wherein thrombocyte aggregation induced by the polypeptide is reduced by at least 10% compared to the thrombocyte aggregation induced by the polypeptide comprising the wild-type human IgG Fc region.

5. The polypeptide according to claim 1, wherein CDC induced by the polypeptide is reduced by at least 50% compared to the CDC induced by the polypeptide comprising the wild-type human IgG Fc region.

6. The polypeptide according to any one of claims 1, 2, or 3-5, wherein the polypeptide is an anti-CD9 antibody comprising the heavy chain variable region of SEQ ID NO:9 and the variable light chain region of SEQ ID NO:8.

7. A pharmaceutical formulation comprising the polypeptide according to claim 6.

8. An article of manufacture comprising the polypeptide according to claim 6.

* * * * *

SEQUENCE LISTING

```
<160> NUMBER OF SEQ ID NOS: 14

<210> SEQ ID NO 1
<211> LENGTH: 107
<212> TYPE: PRT
<213> ORGANISM: Homo Sapiens

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 2
<211> LENGTH: 105
<212> TYPE: PRT
<213> ORGANISM: Homo sapiens

<400> SEQUENCE: 2
```

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr

Gln Lys Ser Leu Ser Leu Ser Pro Gly Lys
            325             330

<210> SEQ ID NO 5
<211> LENGTH: 330
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 327

```
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 7
<211> LENGTH: 327
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 8
<211> LENGTH: 214
<212> TYPE: PRT
<213> ORGANISM: Artificial Sequence
<220> FEATURE:
<223> OTHER INFORMATION: LC_1_1-PEP

<400> SEQUENCE: 8

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Asn Val Lys Leu Leu Ile
        35                  40                  45

```
Tyr Tyr Thr Ser Ser Leu His Ser Gly Val Pro Ser Arg Phe Ser Gly
         50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Tyr
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 9
<211> LENGTH: 449
<212> TYPE: PRT
<213> ORGANISM: Artificial Sequence
<220> FEATURE:
<223> OTHER INFORMATION: 8201_HC_IGG1-PEP

<400> SEQUENCE: 9

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Tyr Ser Gly Phe Thr Asn Tyr Asn Pro Ser Leu
         50                  55                  60

Lys Ser Arg Ile Ser Ile Thr Arg Asp Thr Ser Lys Asn Gln Phe Phe
 65                  70                  75                  80

Leu Gln Leu Ser Ser Val Thr Thr Glu Asp Thr Ala Thr Tyr Phe Cys
                 85                  90                  95

Glu Gly Gly Asn Tyr Arg Tyr Ser Trp Phe Pro Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 10
<211> LENGTH: 449
<212> TYPE: PRT
<213> ORGANISM: Artificial Sequence
<220> FEATURE:
<223> OTHER INFORMATION: 8206_HC_IGG1-P329G-PEP

<400> SEQUENCE: 10

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Phe Thr Asn Tyr Asn Pro Ser Leu
    50                  55                  60

Lys Ser Arg Ile Ser Ile Thr Arg Asp Thr Lys Asn Gln Phe Phe
65                  70                  75                  80

Leu Gln Leu Ser Ser Val Thr Thr Glu Asp Thr Ala Thr Tyr Phe Cys
                85                  90                  95

Glu Gly Gly Asn Tyr Arg Tyr Ser Trp Phe Pro Tyr Trp Gly Gln Gly
```

```
            100                 105                 110
Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 11
<211> LENGTH: 449
<212> TYPE: PRT
<213> ORGANISM: Artificial Sequence
<220> FEATURE:
<223> OTHER INFORMATION: 8207_HC_IGG1-LALA-P329G-PEP

<400> SEQUENCE: 11

Asp Val Gln Leu Gln Glu Ser Gly Pro Gly Leu Val Lys Pro Ser Gln
1               5                   10                  15
```

```
Ser Leu Ser Leu Thr Cys Thr Val Thr Gly Tyr Ser Ile Thr Ser Asp
         20                  25                  30

Tyr Ala Trp Asn Trp Ile Arg Gln Phe Pro Gly Asn Lys Leu Glu Trp
         35                  40                  45

Met Gly Tyr Ile Ser Tyr Ser Gly Phe Thr Asn Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Ser Ser Val Thr Thr Glu Asp Thr Ala Thr Tyr Phe Cys
             85                  90                  95

Glu Gly Gly Asn Tyr Arg Tyr Ser Trp Phe Pro Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
            435                 440                 445

Lys

<210> SEQ ID NO 12
<211> LENGTH: 446
<212> TYPE: PRT
<213> ORGANISM: Artificial Sequence
<220> FEATURE:
<223> OTHER INFORMATION: 8202_HC_IGG4-SPLE-PEP

<400> SEQUENCE: 12

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Phe Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Phe Cys
                85                  90                  95

Glu Gly Gly Asn Tyr Arg Tyr Ser Trp Phe Pro Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro

```
                    340                 345                 350
Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 13
<211> LENGTH: 446
<212> TYPE: PRT
<213> ORGANISM: Artificial Sequence
<220> FEATURE:
<223> OTHER INFORMATION: 8208_HC_IGG4-SPLE-P329G-PEP

<400> SEQUENCE: 13

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Phe Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Phe Cys
                85                  90                  95

Glu Gly Gly Asn Tyr Arg Tyr Ser Trp Phe Pro Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
```

```
            260                 265                 270
Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Gly Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 14
<211> LENGTH: 449
<212> TYPE: PRT
<213> ORGANISM: Artificial Sequence
<220> FEATURE:
<223> OTHER INFORMATION: 8205_HC_IGG1_LALA-PEP

<400> SEQUENCE: 14

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Phe Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Phe Cys
            85                  90                  95

Glu Gly Gly Asn Tyr Arg Tyr Ser Trp Phe Pro Tyr Trp Gly Gln Gly
            100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
```

-continued

```
                180                 185                 190
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```